US011760773B2

(12) United States Patent
Everett et al.

(10) Patent No.: US 11,760,773 B2
(45) Date of Patent: Sep. 19, 2023

(54) SMALL MOLECULE DRUG CONJUGATES OF GEMCITABINE MONOPHOSPHATE

(71) Applicant: MaveriX Oncology, Inc., Palo Alto, CA (US)

(72) Inventors: Steven Albert Everett, Menlo Park, CA (US); Craig Alan Coburn, Novato, CA (US)

(73) Assignee: MaveriX Oncology, Inc., Palo Alto, CA (US)

( * ) Notice: Subject to any disclaimer, the term of this patent is extended or adjusted under 35 U.S.C. 154(b) by 0 days.

(21) Appl. No.: 16/967,049

(22) PCT Filed: Feb. 4, 2019

(86) PCT No.: PCT/US2019/016557
§ 371 (c)(1),
(2) Date: Aug. 3, 2020

(87) PCT Pub. No.: WO2019/152955
PCT Pub. Date: Aug. 8, 2019

(65) Prior Publication Data
US 2021/0040136 A1 Feb. 11, 2021

Related U.S. Application Data

(60) Provisional application No. 62/625,820, filed on Feb. 2, 2018.

(51) Int. Cl.
C07H 19/10 (2006.01)
A61K 47/54 (2017.01)

(52) U.S. Cl.
CPC ........... *C07H 19/10* (2013.01); *A61K 47/545* (2017.08)

(58) Field of Classification Search
CPC .................... C07H 19/10; A61K 47/545
See application file for complete search history.

(56) References Cited

U.S. PATENT DOCUMENTS

| | | |
|---|---|---|
| 4,526,988 A | 7/1985 | Hertel |
| 5,047,521 A | 9/1991 | Fujii et al. |
| 5,061,793 A | 10/1991 | Grindey et al. |
| 5,073,563 A | 12/1991 | Friekel et al. |
| 5,100,914 A | 3/1992 | Rendenbach-Mueller et al. |
| 5,229,272 A | 7/1993 | Paul et al. |
| 5,401,838 A | 3/1995 | Chou |
| 5,464,826 A | 11/1995 | Grindey et al. |
| 6,060,592 A | 5/2000 | Acevedo et al. |
| 6,114,520 A | 9/2000 | Hattori et al. |
| 6,121,308 A | 9/2000 | Hauel et al. |
| 6,175,001 B1 | 1/2001 | Barbas et al. |
| 6,211,166 B1 | 4/2001 | Hattori et al. |
| 6,258,360 B1 | 7/2001 | von Borstel et al. |
| 6,384,019 B1 | 5/2002 | Myhren et al. |
| 6,512,107 B2 | 1/2003 | Chu et al. |
| 6,702,705 B1 | 3/2004 | von Borstel et al. |
| 6,780,859 B2 | 8/2004 | Ladouceur et al. |
| 7,265,096 B2 | 9/2007 | Gallop et al. |
| 7,365,188 B2 | 4/2008 | Roberts et al. |
| 7,585,851 B2 | 9/2009 | Bryant et al. |
| 7,589,078 B2 | 9/2009 | Cheng et al. |
| 7,608,602 B2 | 10/2009 | Gallop et al. |
| 7,691,827 B2 | 4/2010 | Bender et al. |
| 7,803,785 B2 | 9/2010 | Gallop et al. |
| 7,919,628 B2 | 4/2011 | Hachtel et al. |
| 7,989,188 B2 | 8/2011 | Gengrinovitch et al. |
| 8,193,339 B2 | 6/2012 | Chu et al. |
| 8,268,800 B2 | 9/2012 | Hamilton et al. |

(Continued)

FOREIGN PATENT DOCUMENTS

| | | |
|---|---|---|
| CN | 105001291 | 10/2015 |
| EP | 0247381 | 12/1987 |

(Continued)

OTHER PUBLICATIONS

Bankovic et al., "Identification of genes associated with non-small-cell lung cancer promotion and progression," *Lung Cancer*, 67(2):151-159, Epub May 26, 2009.
Baraniak et al., "N-Acyl-phosphoramidates as potential novel form of gemcitabine prodrugs," Bioorgaaic & Medicinal Chemistry, 2014, 2133-2140.
Barnett et al., "Cytochrome P450 1B1 expression in glial cell tumors: an immunotherapeutic target," *Clin Cancer Res.*, 13(12):3559-3567, Jun. 15, 2007.
Berge et al., "Pharmaceutical Salts," Journal of Pharmaceutical Sciences, 1977, 1-19.
Berkow. Ed., *The Merck Manual of Diagnosis and Therapy*, 1992, pp. 1274 and 1292.
Boger et al., "Critical Role of the Linking Amide in CC-1065 and the Duocarmycins: Implications on the Source of DNA Alkylation Catalysis," *J. Am. Chem. Soc.*, 120(45):11554-11557, Epub Nov. 3, 1998.

(Continued)

*Primary Examiner* — Layla D Berry
(74) *Attorney, Agent, or Firm* — Fish & Richardson P.C.

(57) ABSTRACT

Disclosed are compounds having formula (1):

(I)

or a pharmaceutically acceptable salt, ester, amide, solvate, or stereoisomer thereof, wherein L, $Y^1$, $Y^2$, $Y^3$, $Y^4$, $Y^5$, $Z^1$, $Z^2$, $Z^3$, $Z^4$, $Z^5$, $Z^6$ are each as defined in the specification; compositions thereof; uses thereof; and methods of use thereof.

5 Claims, 21 Drawing Sheets

(56) References Cited

U.S. PATENT DOCUMENTS

| | | | |
|---|---|---|---|
| 8,283,340 B2* | 10/2012 | Everett | A61K 31/343 514/100 |
| 8,283,479 B2 | 10/2012 | Hachtel et al. | |
| 8,324,373 B2 | 12/2012 | Xu et al. | |
| 9,919,060 B2* | 3/2018 | Everett | C07D 407/12 |
| 2003/0000088 A1 | 1/2003 | Yerxa et al. | |
| 2005/0130973 A1 | 6/2005 | Xiang et al. | |
| 2006/0258656 A1 | 11/2006 | Matteucci et al. | |
| 2007/0225248 A1 | 9/2007 | Myhren et al. | |
| 2008/0004237 A1 | 1/2008 | Tam et al. | |
| 2008/0085871 A1 | 4/2008 | Tam et al. | |
| 2008/0280851 A1 | 11/2008 | Myhren et al. | |
| 2009/0069557 A1 | 3/2009 | Palle et al. | |
| 2010/0016252 A1 | 1/2010 | Keana et al. | |
| 2010/0016254 A1 | 1/2010 | Gallop et al. | |
| 2010/0305070 A1 | 12/2010 | Everett et al. | |
| 2011/0275590 A1 | 11/2011 | Gengrinovitch et al. | |
| 2012/0190639 A1 | 7/2012 | Everett et al. | |
| 2012/0302748 A1 | 11/2012 | Everett et al. | |
| 2013/0131008 A1 | 5/2013 | Zhengrong et al. | |
| 2015/0011512 A1 | 1/2015 | Everett et al. | |
| 2016/0354399 A1 | 12/2016 | Suo | |
| 2017/0368188 A1 | 2/2017 | Everett et al. | |
| 2019/0060472 A1 | 2/2019 | Everett et al. | |
| 2021/0040136 A1* | 2/2021 | Everett | C07H 19/10 |
| 2021/0380626 A1* | 12/2021 | Everett | A61K 47/545 |

FOREIGN PATENT DOCUMENTS

| | | |
|---|---|---|
| EP | 0363796 | 4/1990 |
| EP | 1300403 | 4/2003 |
| EP | 1676834 | 7/2006 |
| EP | 2857018 | 4/2015 |
| JP | 02-157273 | 6/1990 |
| JP | 04-501253 | 3/1992 |
| JP | 08-511773 | 12/1996 |
| JP | 2002-149579 | 5/2002 |
| JP | 2005-526046 | 9/2005 |
| JP | 2005-526696 | 9/2005 |
| JP | 2006-528162 | 12/2006 |
| JP | 2008-526695 | 7/2008 |
| JP | 2012-525364 | 10/2012 |
| RU | 2191021 | 10/2002 |
| SU | 389090 | 7/1973 |
| WO | WO 1994/029312 | 12/1994 |
| WO | WO 1998/011484 | 3/1998 |
| WO | WO 1999/040056 | 8/1999 |
| WO | WO 1999/040944 | 8/1999 |
| WO | WO 2000/008014 | 2/2000 |
| WO | WO 2001/068591 | 9/2001 |
| WO | WO 2001/072680 | 10/2001 |
| WO | WO 2002/046193 | 6/2002 |
| WO | WO 2002/070500 | 9/2002 |
| WO | WO 2003/024948 | 3/2003 |
| WO | WO 2003/028713 | 4/2003 |
| WO | WO 2003/029176 | 4/2003 |
| WO | WO 2005/012327 | 2/2005 |
| WO | WO 2006/009826 | 1/2006 |
| WO | WO 2006/032921 | 3/2006 |
| WO | WO 2006/069656 | 7/2006 |
| WO | WO 2007/039171 | 4/2007 |
| WO | WO 2008/110793 | 9/2008 |
| WO | WO 2010/125350 | 11/2010 |
| WO | WO 2011/017297 | 2/2011 |
| WO | WO 2015/134334 | 9/2015 |

OTHER PUBLICATIONS

Cali et al., "Luminogenic cytochrome P450 assays", *Expert. Opin. Drug Metabolism Toxicol.*, 2(4):629-645, Aug. 2006.

Carnell et al., "Target validation of cytochrome P450 CYP1B1 in prostate carcinoma with protein expression in associated hyperplastic and premalignant tissue," *Int J Radiat Oncol Biol Phys.*, 58(2):500-509, Feb. 1, 2004.

Chang and Waxman, "Enzymatic analysis of cDNA-expressed human CYP1A1, CYP1A2, and CYP1B1 with 7-ethoxyresorufin as substrate", *Methods Mol. Biol.*, 320:85-90, 2006.

Chang et al., "Real-time polymerase chain reaction analysis of CYP1B1 gene expression in human liver," *Toxicol. Sci.*, 71(1):11-19, Jan. 2003.

Chemical encyclopedia, Moscow, "Soviet encyclopedia", 1983, pp. 130-131.

Chun et al., "A new selective and potent inhibitor of human cytochrome P450 1B1 and its application to antimutagenesis", *Cancer Res.*, 61(22):8164-8170, Nov. 15, 2001.

Dann et al., "[Trypanocidal diamidines with three rings in two isolated ring systems]," *Justus Liebigs Ann Chem.*, 760(761):37-87, Jun.-Jul. 1972, [Article in German].

De Montellano, (ed.), "Cytochrome P450: structure, mechanism, and biochemistry", Kluwer Academic/Plenum Publishers, New York, 2005. [Title page and Table of Contents only.].

Ding et al., "High levels of recombinant CYP3A4 expression in Chinese hamster ovary cells are modulated by coexpressed human P450 reductase and hemin supplementation," *Arch Biochem Biophys.*, 348(2):403-410, Dec. 15, 1997.

Ding et al., "Human NADPH-P450 oxidoreductase modulates the level of cytochrome P450 CYP2D6 holoprotein via haem oxygenase-dependent and -independent pathways," *Biochem J.*, 356(Pt 2):613-619, Jun. 1, 2001.

Downie et al., "Profiling cytochrome P450 expression in ovarian cancer: identification of prognostic markers," *Clin Cancer Res.*, 11(20):7369-7375, Oct. 15, 2005.

Duan et al., "Potent and highly selective hypoxia-activated achiral phosphoramidate mustards as anticancer drugs," *J Med Chem.*, 51(8):2412-2420, Epub Feb. 8, 2008.

Dumont et al., "For knowledge of the coumarone group," European Chemical Societies Publishing, 1909, 911-915 (with Machine translation).

Edler et al., "The expression of the novel CYP2W1 enzyme is an independent prognostic factor in colorectal cancer—a pilot study," *Eur J Cancer.*, 45(4):705-712, Epub Dec. 30, 2008.

Ellingboe et al., "Antihyperglycemic activity of novel substituted 3H-1,2,3,5-oxathiadiazole 2-oxides," *J Med Chem.*, 35(7):1176-1183, Apr. 3, 1992.

Everett et al., "Modifying rates of reductive elimination of leaving groups from indolequinone prodrugs: a key factor in controlling hypoxia-selective drug release," *Biochem Pharmacol.*, 63(9):1629-1639, May 1, 2002.

Everett et al., "Profiling cytochrome P450 CYPI enzyme expression in primary melanoma and disseminated disease utilizing spectral imaging microscopy (SIM)", *J Clin Oncol.*, 25(18s):486s, Abstract No. 8556, 2007.

Flader et al., "Development of novel quinone phosphorodiamidate prodrugs targeted to DT-diaphorase," *J Med Chem.*, 43(16):3157-3167, Aug. 10, 2000.

Gibson et al., "Cytochrome P450 1B1 (CYP1B1) is overexpressed in human colon adenocarcinomas relative to normal colon: implications for drug development," *Mol Cancer Ther.*, 2(6):527-534, Jun. 2003.

Greer et al., "Cytochrome P450 1B1 (CYP1B1) is expressed during the malignant progression of head and neck squamous cell carcinoma (HNSCC)," *Proc Amer Assoc Cancer Res*, vol. 45 Abstract No. 3701, 2 pages, 2004.

Grinev et al., "Synthesis and biological activity of 3-arylbenzofuran derivatives," *Pharmaceutical Chemistry Journal*, 13(8):814-819, Aug. 1, 1979.

Gura, "Systems for identifying new drugs are often faulty," *Science*, 278(5340): 1041-1042, Nov. 7, 1997.

Haas et al., "Expression of xenobiotic and steroid hormone metabolizing enzymes in human breast carcinomas," *Int J Cancer.*, 119(8):1785-1791, Oct. 15, 2006.

Hernick et al., "Design, synthesis, and biological evaluation of indolequinone phosphoramidate prodrugs targeted to DT-diaphorase," *J Med Chem.*, 45(16):3540-3548, Aug. 1, 2002.

Hessel et al., "Differentiation status of human squamous cell carcinoma xenografts does not appear to correlate with the repopula-

(56) References Cited

OTHER PUBLICATIONS tion capacity of clonogenic tumour cells during fractionated irradiation," *Int J Radiat Biol.*, 80(10):719-727, Oct. 2004.
Horwell et al., "Quantitative structure-activity relationships (QSARs) of N-terminus fragments of NK1 tachykinin antagonists: a comparison of classical QSARs and three-dimensional QSARs from similarity matrices," *J Med Chem.*, 38(22):4454-4462, Oct. 27, 1995.
Hu et al., "Potent, selective, and orally bioavailable matrix metalloproteinase-13 inhibitors for the treatment of osteoarthritis," *Bioorg Med Chem.*, 13(24):6629-6644, Epub Oct. 10, 2005.
Ingehnan-Sundberg, "The human genome project and novel aspects of cytochrome P450 research," *Toxicol Appl Pharmacol.*, 207(2 Suppl):52-56, Sep. 1, 2005.
Jensen et al., "In silico prediction of cytochrome P450 2D6 and 3A4 inhibition using Gaussian kernel weighted k-nearest neighbor and extended connectivity fingerprints, including structural fragment analysis of inhibitors versus noninhibitors" *J Med Chem.*, 50(3):501-511, Feb. 8, 2007.
Kumarakulasingham et al., "Cytochrome p450 profile of colorectal cancer: identification of markers of prognosis," *Clin Cancer Res.*, 11(10):3758-3765, May 15, 2005.
Lau et al., "Development of 2,3-dihydro-6-(3-phenoxypropyl)-2-(2-phenylethyl)-5-benzofuranol (L-670,630) as a potent and orally active inhibitor of 5-lipoxygenase," *J Med Chem.*, 35(7):1299-1318, Apr. 3, 1992.
McFadyen and Murray, "Cytochrome P450 1B1: a novel anticancer therapeutic target," *Future Oncol.*, 1(2):259-263, Apr. 2005.
McFadyen et al., "Cytochrome P450 1B1: a novel anticancer therapeutic target," Future Medicine, 2005, 259-263.
McFadyen et al., "Cytochrome P450 CYP1B1 activity in renal cell carcinoma," *Br J Cancer.*, 91(5):966-971, Aug. 31, 2004.
McFadyen et al., "Cytochrome P450 CYP1B1 activity in renal cell carcinoma," British Journal of Cancer, 2004, 966-971.
McFadyen et al., "Cytochrome P450 CYP1B1 over-expression in primary and metastatic ovarian cancer," *Br J Cancer.*, 85(2):242-246, Jul. 20, 2001.
McFadyen et al., "Cytochrome P450 CYP1B1 protein expression: a novel mechanism of anticancer drug resistance," *Biochem Pharmacol.*, 62(2):207-212, Jul. 15, 2001.
McFadyen et al., "Cytochrome P450 CYP1B1 protein expression: a novel mechanism of anticancer drug resistance," *Biochemical Pharmacology.*, 2001, 207-212.
McFadyen et al., "Cytochrome P450 enzymes: novel options for cancer therapeutics," *Mol Cancer Ther.*, 3(3):363-371, Mar. 2004.
McGuigan et al., "Phosphorodiamidates as a Promising New Phosphate Prodrug Motif for Antiviral Drug Discovery: Application to Anti-HCV Agents," Journal of Medicinal Chemistry, 2011, 8632-8645.
McKay et al., "Differential expression of CYP1A1 and CYP1B1 in human breast cancer," *Biochem Soc Trans.*, 24(2):327S, May 1996.
Mikata et al., "Methoxy-substituted TQEN family of fluorescent zinc sensors," *Inorg Chem.*, 45(23):9262-9268, Nov. 13, 2006.
Mukhanova et al., "A study of the Claisen—Eschenmoser reaction for hydroxymethylbenzofurans and-indoles," *Russian Chemical Bulletin*, 56(2):325-329, Feb. 2007.
Munray et al., "Tumor-specific expression of cvtochrome P450 CYP1B1," *Cancer Res.*, 57(14):3026-3031, Jul. 15, 1997.
Paine et al., "Functional high level expression of cytochrome P450 CYP2D6 using baculoviral expression systems," *Arch Biochem Biophys.*, 328(1):143-150, Apr. 1, 1996.

Patterson and Murray, "Tumour cytochrome P450 and drug activation," *Curr Pharm Des.*, 8(15):1335-1347, 2002.
PCT International Preliminary Report on Patentability in International Appln. No. PCT/US2019/016477, dated Aug. 4, 2020, 11 pages.
PCT International Preliminary Report on Patentability in International Appln. No. PCT/US2019/0165577, dated Aug. 4, 2020, 12 pages.
PCT International Search Report in International Application No. PCT/GB2010/000860, dated Nov. 4, 2010, 8 pages.
PCT International Search Report in International Application No. PCT/US2019/016477, dated May 17, 2019, 8 pages.
PCT International Search Report in International Application No. PCT/US2019/016557, dated May 17, 2019, 8 pages.
Rendic, "Summary of information on human CYP enzymes: human P450 metabolism data," *Drug Metab Rev.*, 34(1-2):83-448, Feb.-May 2002.
Rieger et al., "Identification of a novel mammary-restricted cytochrome P450, CYP4Z1, with overexpression in breast carcinoma," *Cancer Res.*, 64(7):2357-2364, Apr. 1, 2004.
Sissung et al., "Association of the CYP1B1*3 allele with survival in patients with prostate cancer receiving docetaxel," *Mol Cancer Ther.*, 7(1):19-26, Epub Jan. 9, 2008.
Sissung et al., "Pharmacogenetics and regulation of human cytochrome P450 1B1: implications in hormone-mediated tumor metabolism and a novel target for therapeutic intervention," *Mol Cancer Res.*, 4(3):135-150, Mar. 2006.
Slusarczyk et al., "Application of ProTide Technology to Gemcitabine: A Successful Approach to Overcome the Key Cancer Resistance Mechanisms Leads to a New Agent (NUC-1031) in Clinical Development," Journal of Medicinal Chemistry, 2014, 1531-1542.
Stark and Guenerieh, "Characterization of orphan human cytochromes P450," Drug Metab Rev., 39(2-3):627-637, 2007.
Su et al., "Overexpression of cytochrome P450 1B1 in advanced non-small cell lung cancer: a potential therapeutic target," *Anticancer Res.*, 29(2):509-515, Feb. 2009.
Sutter et al.. "Complete cDNA sequence of a human dioxin-inducible mRNA identifies a new gene subfamily of cytochrome P450 that maps to chromosome 2," *J Biol Chem.*, 269(18):13092-13099, May 6, 1994.
Veith et al., "Comprehensive characterization of cytochrome P450 isozyme selectivity across chemical libraries," *Nat Biotechnol.*, 27(11):1050-1055. Epub Oct. 25, 2009.
Waxman and Chang, "Use of 7-ethoxycoumarin to monitor multiple enzymes in the human CYP1, CYP2, and CYP3 families," *Methods Mol Biol.*, 320:153-156, 2006.
Wickremsinhe et al., Preclinical Absorption, Distribution, Metabolism, and Excretion of an Oral Amide Prodrug of Gemcitabine Designed to Deliver Prolonged Systemic Exposure, Pharmaceutics, 2013, 5(4):261-276.
Yaromina et al., "Pre-ireatment number of clonogenic cells and their radiosensitivity are major determinants of local tumour control after fractionated irradiation," *Radiother Oncol.*, 83(3):304-310, Epub May 22, 2007.
Mini et al., "Cellular pharmacology of gemcitabine," Annals of oncology, May 1, 2006, 17:v7-12.
Rautio et al., "Prodrugs: design and clinical applications," Nature reviews Drug discovery, Mar. 2008, 7(3):255-270.
Shaheed "Design and synthesis of diclofenac and indomethacin-conjugates with gemcitabine as a possible mutual prodrugs," World Journal of Pharmaceutical Research, Nov. 19, 2014, (2): 8-17.

\* cited by examiner

Compound 1 (IV, F1, 10.0 mg/kg) - ND
Compound 1 (IV, F2, 10.0 mg/kg) - ND
■ Int 1-4 (IV, F1, 10.0 mg/kg)
● Int 1-4 (IV, F2, 10.0 mg/kg
▨ gemcitabine (IV, F1,10.0 mg/kg)
● gemcitabine (IV, F2, 10.0 mg/kg)
▨ dFdU (IV, F1, 10.0 mg/kg)
● dFdU (IV, F2, 10.0 mg/kg)
gemcitabine mono-phosphate (IV, F1,10.0 mg/kg) - ND
gemcitabine mono-phosphate (IV, F2, 10.0 mg/kg) - ND

SMALL MOLECULE DRUG CONJUGATES OF GEMCITABINE MONOPHOSPHATE

PRIORITY CLAIM

This application is a National Stage Application under 35 U.S.C. § 371 and claims the benefit of International Application No. PCT/US2019/016557, filed Feb. 4, 2019, which claims the benefit of U.S. Provisional Application No. 62/625,820, filed on Feb. 2, 2018, which are incorporated herein by reference in their entireties.

FIELD OF THE INVENTION

The present invention relates to novel small molecule drug conjugates (SMDCs) for use in the treatment or prophylaxis of cancers and other proliferative conditions that are, for example, characterized by cells that express cytochrome P450 1B1 (CYP1B1) and allelic variants thereof. The present invention also provides pharmaceutical compositions comprising one or more such compounds for use in medical therapy, for example in the treatment or prophylaxis of cancers or other proliferative conditions, as well as methods for treating cancers or other conditions in human or non-human animal patients. Other aspects of the invention are further disclosed in the specification.

BACKGROUND OF THE INVENTION

CYP1B1 is a member of the dioxin-inducible CYP1 gene family which also includes CYP1A1 and CYP1A2 as described by Sutter et al. (*J Biol. Chem.*, May 6; 269(18): 13092-9, 1994). CYP1B1 is a hemethiolate mono-oxygenase enzyme that is capable of metabolizing and activating a variety of substrates including steroids, xenobiotics, drugs and/or SMDCs.

CYP1B1 protein is expressed to a high frequency in a wide range of primary and metastatic human cancers of different histogenic types and is not expressed or at negligible levels in normal tissue. (e.g. McFadyen M C, Melvin W T and Murray G I, "Cytochrome P450 Enzymes: Novel Options for Cancer Therapeutics", *Mol Cancer Ther.*, 3(3): 363-71, 2004; McFadyen M C and Murray G I, "Cytochrome P450 1B1: a Novel Anticancer Therapeutic Target", *Future Oncol.*, 1(2): 259-63, 2005.

More specifically, CYP1B1 has been shown to be expressed in bladder, brain, breast, colon, head and neck, kidney, lung, liver, ovarian, prostate and skin cancers, without being expressed in the corresponding normal tissue. For example, Barnett, et al. in *Clin. Cancer Res.*, 13(12): 3559-67, 2007, reported that CYP1B1 was over-expressed in glial tumors, including glioblastomas, anaplastic astrocytomas, oligodendrogliomas and anaplastic oligodendrogliomas, but not unaffected brain tissue; Carnell, et al., in *Int. J. Radiat. Oncol. Biol. Phys.*, 58(2): 500-9, 2004, reported that CYP1B1 was over-expressed in prostate adenonocarcinomas, but not in matched normal prostate tissue; Carnell, et al., 2004 (ibid.) also showed that CYP1B1 is expressed in (n=22, 100%) of bladder carcinomas; Downie, et al., in *Clin. Cancer Res.*, 11(20): 7369-75, 2005 and McFadyen, et al., in *Br. J. Cancer*, 85(2): 242-6, 2001, reported increased expression of CYP1B1 in primary and metastatic ovarian cancer, but not in normal ovary tissue; and Gibson, et al., in *Mol. Cancer Ther.*, 2(6): 527-34, 2003, and Kumarakulasingham, et al., in *Clin. Cancer Res.*, 11(10): 3758-65, 2005, reported that CYP1B1 was over-expressed in colon adenocarcionomas as compared to matched normal tissue.

Several studies have shown that CYP1B1 is over-expressed in breast cancer as compared to matched normal tissue (see, e.g.: Murray G I, Taylor M C, McFadyen M C, McKay J A, Greenlee W F, Burke M D and Melvin W T, "Tumor-Specific Expression of Cytochrome P450 CYP1E1", *Cancer Res.*, 57(14): 3026-31, 1997; Haas S, Pierl C, Harth V, Pesch B, Rabstein S, Bruning T, Ko Y, Hamann U, Justenhoven C, Brauch H and Fischer H P, "Expression of Xenobiotic and Steroid Hormone Metabolizing Enzymes in Human Breast Carcinomas". *Int. J. Cancer*, 119(8): 1785-91, 2006; McKay J A, Murray G I, Ah-See A K, Greenlee W F, Marcus C B, Burke M D and Melvin W T, "Differential Expression of CYP1A1 and CYP1B1 in Human Breast Cancer", *Biochem. Soc. Trans.*, 24(2): 327S, 1996).

Everett, et al., in *J. Clin. Oncology*, 25: 18S, 2007, reported that CYP1B1 was over-expressed in malignant melanoma and disseminated disease but not in normal skin. Chang, et al., in *Toxicol. Sci.*, 71(1): 11-9, 2003, reported that CYP1B1 protein is not present in normal liver but Everett, et al., 2007 (ibid.) confirmed CYP1B1 over-expression in melanoma stage IV metastasis to the liver but not in the adjacent normal liver tissue.

Greer, et al., in *Proc. Am. Assoc. Cancer Res.*, 45: 3701, 2004, reported that CYP1B1 was over-expressed during the malignant progression of head and neck squamous cell carcinoma but not in normal epithelium.

McFadyen, et al., in *Br. J. Cancer*, 91(5): 966-71, 2004, detected CYP1B1 in renal carcinomas but not in corresponding normal tissue.

Murray, et al., 2004 (ibid.) used immunohistochemistry to show over-expression of CYP1B1 in lung cancer cells as compared to normal lung tissue. Su, et al., in *Anti-Cancer Res.*, 2, 509-15, 2009, used immunohistochemistry to show over-expression of CYP1B1 in advanced stage IV non-small cell lung cancer compared to earlier stages of the disease.

It is evident from the numerous disclosures cited above that CYP1B1 expression is characteristic of a range of different cancers and other proliferative conditions, and that CYP1B1 expression may be used to define such a range of cancers and other conditions. As normal (non-cancerous) cells do not express significant levels of CYP1B1, it may also be reasonably expected that compounds that exhibit cytotoxicity in cells expressing CYP1B1, but are substantially non-cytotoxic in normal cells, would have utility as targeted anti-cancer agents in cancers characterized by CYP1B1 expression. By "targeted" is meant that such compounds could be delivered systemically and would only be activated in the presence of cancerous cells expressing CYP1B1, remaining substantially non-toxic to the rest of the body.

Furthermore, a number of cytochrome P450 enzymes are known to metabolize and detoxify a variety of anticancer drugs. McFadyen, et al. (*Biochem Pharmacol.* 2001, Jul. 15; 62(2): 207-12) demonstrated a significant decrease in the sensitivity of docetaxel in cells expressing CYP1B1 as compared with non-CYP1B1 expressing cells. This finding indicates that the presence of CYP1B1 in cells may decrease their sensitivity to some cytotoxic drugs. CYP1B1-activated SMDCs may therefore be useful for the treatment of cancers whose drug resistance is mediated by CYP1B1.

Furthermore, the CYP1B1 gene is highly polymorphic in cancer and several single nucleotide polymorphisms contained within the CYP1B1 gene have been identified that alter the expression and/or activity of the encoded protein. Of these, the CYP1B1*3 (4326C>G; L432V) allele has been characterized by both increased expression and enzyme kinetics of CYP1B1 toward several substrates as described by Sissung, et al. in *Mol Cancer Ther.*, 7(1): 19-26, 2008 and references quoted therein. This finding indicates that not only CYP1B1, but the allelic variants of the enzyme may also contribute to SMDC activation and cancer targeting.

SMDCs have been investigated as a means to lower the unwanted toxicity or some other negative attribute of a drug without loss of efficacy. A SMDC is a drug that has been chemically modified to render it inactive but that, subsequent to administration, is metabolized or otherwise converted to an active form of the drug in the body. The over-expression of CYP1B1 in primary tumors and metastatic disease compared to normal tissue offers a tremendous opportunity for the development of CYP1B1-activated SMDCs for targeted cancer therapy as reviewed by McFadyen et al., *Mol Cancer Ther.*, 3(3), 363-71, 2004. Indeed, the discovery and development of CYP1B1-activated SMDCs for targeted cancer therapy is likely to offer significant pharmacological advantages over existing non-targeted cytochrome P450-activated SMDCs used clinically such as the SMDC alkylating agents cyclophosphamide, ifosfamide, dacarbazine, procarbazine which are activated by cytochrome P450s expressed in normal tissue as reviewed by Patterson L H and Murray G I in *Curr Pharm Des.*, 8(15): 1335-47, 2002.

Utilization of so-called 'trigger-linker-effector' chemistry in SMDC design requires the activation of the trigger to initiate the fragmentation of a linker to release an effector (typically an active drug), the biological activity of which is masked in the SMDC form. The modular design of selective SMDCs targeted at tumor-expressing cytochrome P450s such as CYP1B1 require (1) the identification of selective trigger moieties, (2) the use of bio-stable linkers which fragment efficiently following trigger activation (usually by aromatic hydroxylation), and (3) suitable effectors or drugs which do not interfere with the efficiency of the triggering process.

WO 99/40944 describes SMDCs that comprise a drug moiety bound to a carrier framework, the SMDC being described activated as through hydroxylation by CYP1B1 to release the drug moiety.

WO 2010/125350 also describes SMDCs activated as through hydroxylation by CYP1B1 to release a drug moiety.

Accordingly, there remains a strong need for novel SMDC's that are useful for patients in need thereof.

SUMMARY OF THE INVENTION

The present invention provides SMDCs described having novel structural and functional features, wherein these novel features have been developed to fulfill unmet needs of patients in need of these SMDCs.

According to a first aspect, the present invention relates to a compound of formula (I):

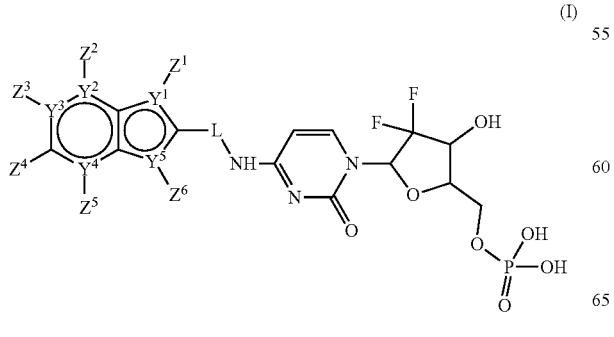

(I)

or a pharmaceutically acceptable salt, ester, solvate, or stereoisomer thereof, wherein:

-L- is defined as: —$(C_1$-$C_5)$alkylene-O—C(O)—, —$(C_3$-$C_5)$alkenylene-O—,

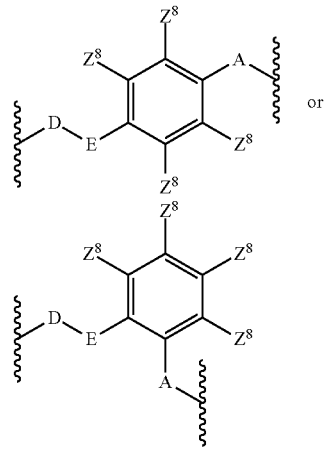

A is —$(C_1$-$C_5)$alkylene-O—C(O)—;
E is —O—, —O—C(O)N(H)—, —O—C(S)N(H)— or —S— or —S—C(O)N(H)—;
D is —$(C_1$-$C_5)$alkylene- or —$(C_3$-$C_5)$alkenylene-;
$Y^1$ is C=C, carbon or nitrogen, wherein if $Y^1$ is nitrogen, $Z^1$ is absent;
Each of $Y^4$ and $Y^5$ is independently carbon or nitrogen, wherein if $Y^3$ is nitrogen, $Z^3$ is absent and if $Y^4$ is nitrogen, $Z^5$ is absent;
$Y^2$ is C or N wherein if $Y^2$ is nitrogen, $Z^2$ is absent;
$Y^5$ is an oxygen, carbon, nitrogen or a sulfur atom, wherein $Z^6$ is absent when $Y^5$ is an oxygen, or a sulfur atom;
Each of $Z^1$, and $Z^2$, where present, are independently selected from hydrogen, alkyl, alkenyl, alkynyl, aryl, heteroaryl, aralkyl, alkyloxy, alkenyloxy, alkynyloxy, aryloxy, aralkyloxy, alkylthioxy, alkenylthioxy, alkynylthioxy, arylthioxy, aralkylthioxy, amino, hydroxy, thio, halo, carboxy, formyl, nitro and cyano, wherein each alkyl, alkenyl, alkynyl, alkoxy, and aryl moiety is independently optionally substituted with 1-3 halo;
$Z^3$, $Z^4$, and $Z^5$ are each independently selected from hydrogen, alkyl, deuterated alkyl, $C_{1-6}$alkoxy, deuterated $C_{1-6}$alkoxy, alkenyl, alkynyl, aryl, aralkyl, alkyloxy, alkenyloxy, alkynyloxy, aryloxy, aralkyloxy, alkylthioxy, alkenylthioxy, alkynylthioxy, arylthioxy, aralkylthioxy, amino, alkylamino, aralkylamino, arylamino, hydroxy, thio, halo, carboxy, formyl, nitro and cyano, wherein each alkyl, alkenyl, alkynyl, alkoxy, and aryl moiety is independently optionally substituted with 1-3 halo;
provided that at least one of $Z^1$, $Z^2$ or $Z^4$ is H;
$Z^6$ is selected from hydrogen, alkyl, alkenyl, alkynyl, aryl and aralkyl, wherein each alkyl, alkenyl, alkynyl, alkoxy, and aryl moiety is independently optionally substituted with 1-3 halo;
Each $Z^8$ is independently hydrogen, unsubstituted $C_1$-$C_6$ alkyl, substituted $C_1$-$C_6$ alkyl, unsubstituted $C_1$-$C_6$ alkoxy, unsubstituted deuterated $C_1$-$C_6$ alkoxy, substituted $C_1$-$C_6$ alkoxy, and substituted deuterated $C_1$-$C_6$ alkoxy where the substituted alkyl, alkoxy and deuterated alkoxy are substituted with one or more groups selected from amino, mono- or di-substituted amino, cyclic $C_1$-$C_5$ alkylamino, imidazolyl, $C_1$-$C_6$ alkylpiperazinyl, morpholino, thiol, thioether, tetrazole, carboxylic acid, ester, amido, mono- or di-substituted amido, N-connected amide, N-connected sulfonamide, sulfoxy, sulfonate, sulfonyl, sulfoxy, sulfinate, sulfinyl, phosphonooxy, phosphate or sulfonamide, wherein each alkyl, alkenyl, alkynyl, alkoxy, and aryl is optionally substituted with 1-3 halo.

Another aspect the invention relates to a compound of the invention as described in the specification, or a pharmaceutically acceptable salt, ester, amide or solvate thereof, for use as a medicament.

Another aspect of the invention relates to a compound of the invention as described in the specification, or a pharmaceutically acceptable salt, ester, amide or solvate thereof, for use in a method of treatment or prophylaxis of a proliferative condition.

Another aspect of the invention relates to method of treatment or prophylaxis comprising administering a therapeutically or prophylactically useful amount of a compound of the invention as described in the specification to a patient in need thereof.

Another aspect of the invention relates to method of treatment or prophylaxis comprising administering a therapeutically or prophylactically useful amount compound of the invention as described in the specification to a patient in need thereof, wherein the proliferative condition is a cancer selected from bladder, brain, breast, colon, head and neck, kidney, lung, liver, ovarian, pancreatic, prostate or skin cancer.

Another aspect of the invention relates to a method of treatment or prophylaxis of a proliferative condition, said method comprising administering a therapeutically or prophylactically useful amount of a compound of the invention as described in the specification, or pharmaceutically acceptable salt, ester, amide or solvate thereof, to a subject in need thereof.

Another aspect of the invention relates to the use of a compound of the invention as described in the specification, or a pharmaceutically acceptable salt, ester, amide or solvate thereof, for the preparation of medicament for use in a method of treatment or prophylaxis of a proliferative condition.

Another aspect of the invention relates to a method of diagnosis of a patient for the presence of tumor cells expressing the CYP1B1 enzyme comprising (a) administering to the patient a specific SMDC disclosed in any of the embodiments described herein; (b) determining the amount of corresponding hydroxylated metabolite which is subsequently produced; and, (c) correlating the amount with the presence or absence of the tumor cells in the patient.

Another aspect of the invention relates to a method of (1) identifying the presence of a tumor in a patient; and (2) treating the patient, identified as needing the treatment, by administering a therapeutically or prophylactically useful amount of a compound of the invention as described in the specification, or pharmaceutically acceptable salt, ester, amide or solvate thereof.

Another aspect of the invention relates to intermediate compounds that can be used to make certain compounds of formula (I), wherein the intermediate is as defined in formula (I), or a pharmaceutically acceptable salt, ester, amide, solvate, or stereoisomer thereof.

Further aspects and embodiment of the invention will follow from the discussion that follows below.

DETAILED DESCRIPTION OF THE INVENTION

Figure 1A:
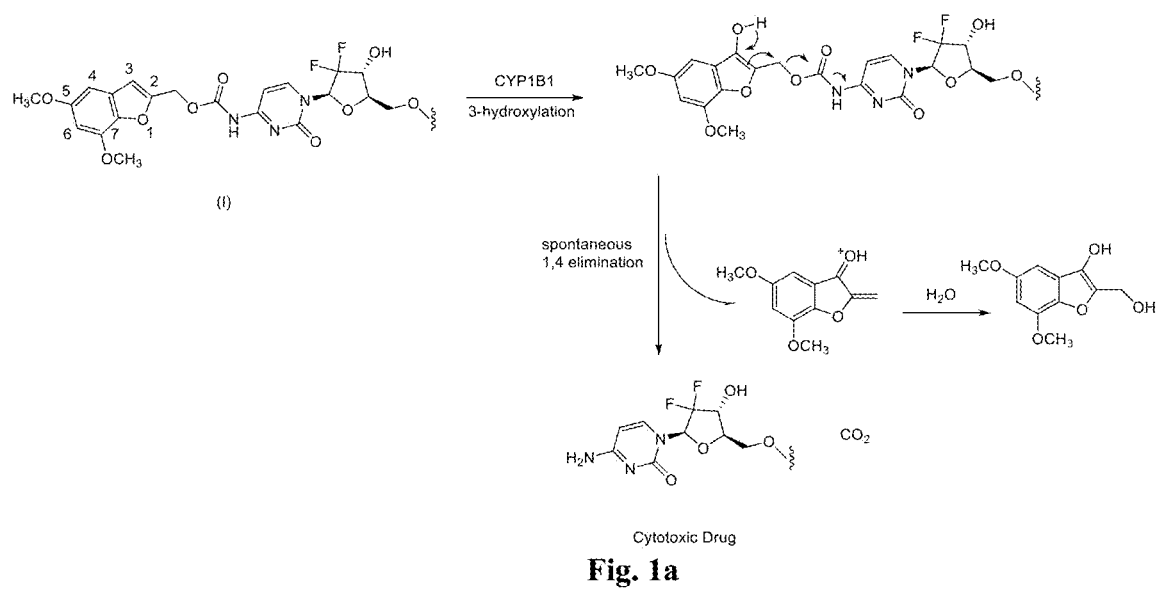
FIG. 1a shows a mechanism for CYP1B1-induced 3-hydroxylation of (5,7-di(methoxy)benzofuran-2-yl)methyl (1-((2R,4R,5R)-3,3-difluoro-4-hydroxy-5-(hydroxymethyl)tetrahydrofuran-2-yl)-2-oxo-1,2-dihydropyrimidin-4-yl) carbamate (1) followed by spontaneous release of the cytotoxic Effector molecule by 1,4 elimination.
Figure 1B:
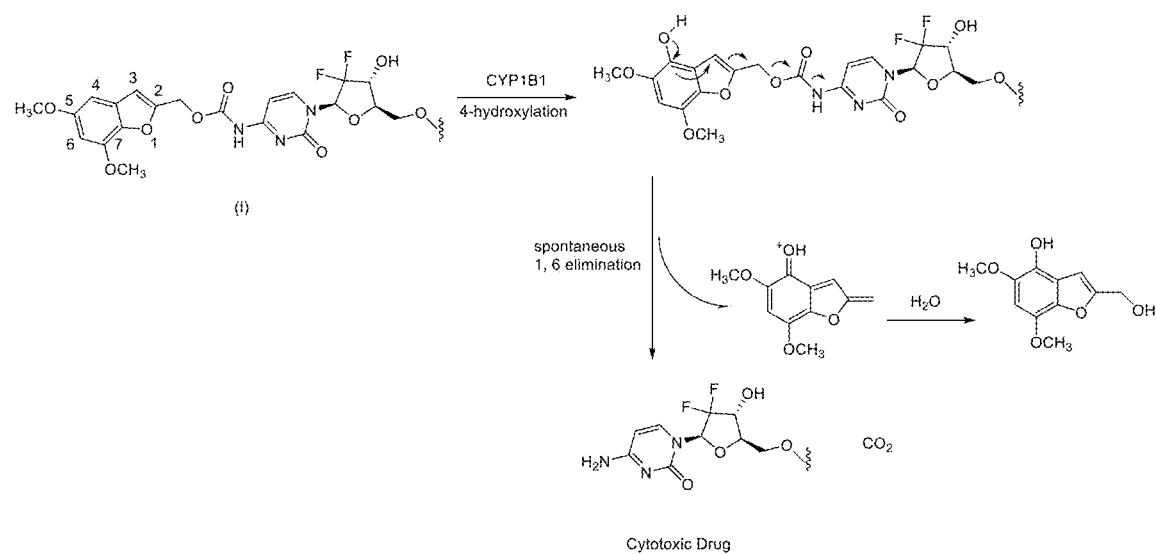
FIG. 1b shows a mechanism for CYP1B1-induced 4-hydroxylation of (5,7-di(methoxy)benzofuran-2-yl)methyl(1-((2R,4R,5R)-3,3-difluoro-4-hydroxy-5-(hydroxyl-methyl) tetrahydrofuran-2-yl)-2-oxo-1,2-dihydropyrimidin-4-yl) carbamate (1) followed by spontaneous release of the cytotoxic Effector molecule by 1,6 elimination.
Figure 1C:
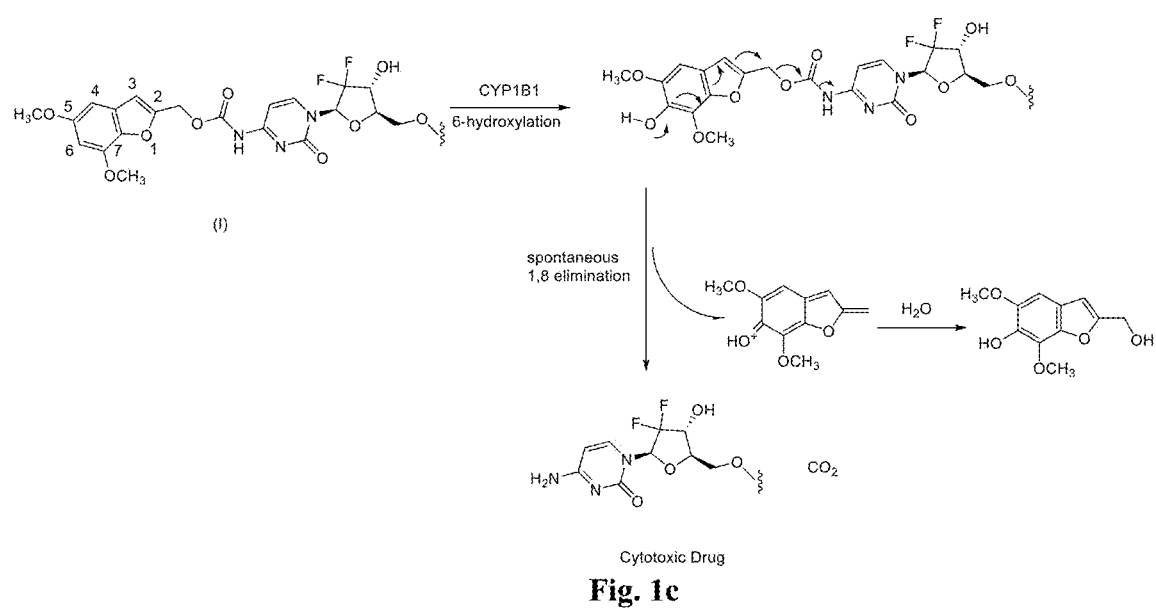
FIG. 1c shows a mechanism for CYP1B1-induced 6-hydroxylation of (5,7-di(methoxy)benzofuran-2-yl)methyl (1-((2R,4R,5R)-3,3-difluoro-4-hydroxy-5-(hydroxyl-methyl) tetrahydrofuran-2-yl)-2-oxo-1,2-dihydropyrimidin-4-yl) carbamate (1) followed by spontaneous release of the cytotoxic Effector molecule by 1,8 elimination.
Figure 1D:
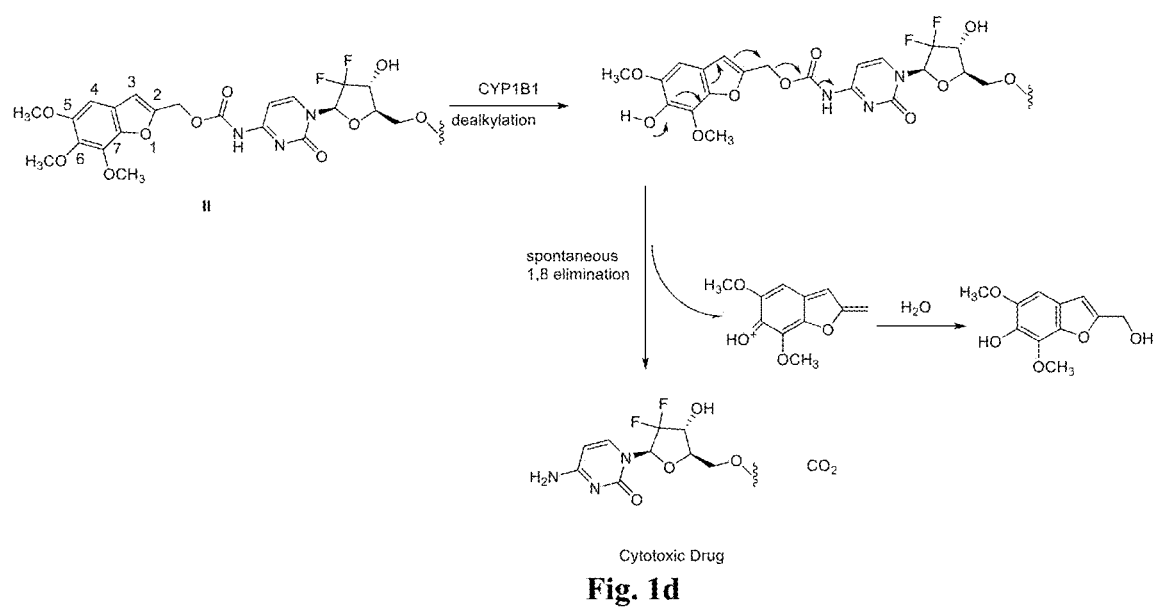
FIG. 1d shows a mechanism for CYP1B1-induced C-6 dealkylation of (5,6,7-tri(methoxy)benzofuran-2-yl)methyl (1-((2R,4R,5R)-3,3-difluoro-4-hydroxy-5-(hydroxyl-methyl)tetrahydrofuran-2-yl)-2-oxo-1,2-dihydro-pyrimidin-4-yl)carbamate (II) followed by spontaneous release of the cytotoxic Effector molecule by 1,6 elimination.

Disclosed are SMDCs in which the Effector molecule is a gemcitabine analog having a pharmacological function.

These Effector molecules are chemically modified by reacting it whereby to form a compound of formula (I). Hydroxylation of compounds of formula (I), such as CYP1B1-induced hydroxylation, allows release of the gemcitabine molecules by a collapse of the compounds of formula (I) which happens as a result of hydroxylation or hydroxylation via epoxide formation. Alternatively, dealkylation of compounds of formula (II), such as CYP1B1-induced dealkylation, allows release of the gemcitabine molecule by a collapse of the compounds of formula (II).

In overview, the structure of the compounds of formula (I) may be considered to comprise three parts: a trigger region, a linker and a monophosphorylated gemcitabine molecule. The trigger serves as a substrate for the typically CYP1B1-induced hydroxylation and may be generally understood to comprise the bicyclic moiety depicted on the left hand side of formula (I) and the substituents thereof, i.e. comprising that part of the compounds containing $Y^1$, $Y^2$, $Y^3$, $Y^4$, $Y^5$, $Z^1$, $Z^2$, $Z^3$, $Z^4$, $Z^5$, $Z^6$ and the remaining carbon atoms to which some of these moieties are attached.

The trigger region of the compounds is attached through a linker region comprising L, and the linker region is attached to the Effector molecule which is labeled as such. In the discussion that follows, reference is made to a number of terms, which are to be understood to have the meaning provided, below, unless the context dictates to the contrary.

When chemical structures are depicted or described, unless explicitly stated otherwise, all carbons are assumed to have hydrogen substitution to conform to a valence of four. For example, for the chemical moiety —C(C)$_3$, there are nine hydrogens implied so that the structure is —C(CH$_3$)$_3$. Sometimes a particular atom in a structure is described in textual Formula as having a hydrogen or hydrogens as substitution (expressly defined hydrogen), for example, —CH$_2$CH$_2$—. It is understood by one of ordinary skill in the art that the aforementioned descriptive techniques are common in the chemical arts to provide brevity and simplicity to description of otherwise complex structures.

Unless a point of attachment indicates otherwise, the chemical moieties listed in the definitions of the variables of formula (I), and all the embodiments thereof, are to be read from left to right, wherein the right hand side is directly attached to the parent structure as defined. However, if a point of attachment is shown on the left hand side of the chemical moiety (e.g., -alkyloxy-(C$_1$-C$_{25}$)alkyl), then the left hand side of this chemical moiety is attached directly to the parent moiety as defined.

It is assumed that when considering generic descriptions of compounds of the disclosed herein for the purpose of constructing a compound, such construction results in the creation of a stable structure. That is, one of ordinary skill in the art would recognize that theoretically some constructs which would not normally be considered as stable compounds (that is, sterically practical and/or synthetically feasible)

The compounds described herein, as well as their pharmaceutically acceptable salts or other derivatives thereof, can optionally exist in isotopically-labeled form, in which one or more atoms of the compounds are replaced by an atom having the same atomic number but an atomic mass different from the atomic mass usually found in nature. Examples of isotopes that can be incorporated into compounds described herein include isotopes of hydrogen, carbon, nitrogen, oxygen, phosphorous, sulfur, fluorine and chloride, such as $^2$H (deuterium), $^3$H (tritium), $^{13}$C $^{14}$C, $^{15}$N, $^{18}$O, $^{17}$O, $^{31}$P, $^{32}$P, $^{35}$S, $^{18}$F and $^{36}$Cl, respectively. Isotopically labeled compounds described herein, as well as pharmaceutically acceptable salts, esters, SMDCs, solvates, hydrates or other derivatives thereof, generally can be prepared by carrying out the procedures disclosed in the Schemes and/or in the Examples below, by substituting a readily available isotopically labeled reagent for a non-isotopically labeled reagent. When a particular hydrogen position is replaced with a "D" or "deuterium", it is to be understood that the abundance of deuterium at that position is substantially greater than the natural abundance of deuterium, which is 0.015%, and typically has at least 50% deuterium incorporation at that position. In one embodiment, one or more hydrogens attached to one or more sp$^3$ carbons in the compounds disclosed herein are replaced with deuterium. In another embodiment, one or more hydrogens attached to one or more sp$^2$ carbons in the compounds disclosed herein are replaced with deuterium.

Optional" or "optionally" means that the subsequently described event or circumstance can or cannot occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" means substituted or unsubstituted and refers to all subsequent modifiers in a term unless otherwise specified. So, for example, in the term "optionally substituted arylalkyl," both the "alkyl" portion and the "aryl" portion of the molecule can be substituted or unsubstituted.

Unless otherwise specified, the term "optionally substituted" applies to the chemical moiety immediately preceding it. For instance, if a variable group (such as R) is defined as aryl, optionally substituted alkyl, or cycloalkyl, then only the alkyl group is optionally substituted.

A "pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in Remington's Pharmaceutical Sciences, 17.sup.th ed., Mack Publishing Company, Easton, Pa., 1985, which is incorporated herein by reference or S. M. Berge, et al., "Pharmaceutical Salts," *J. Pharm. Sci.,* 1977; 66:1-19 both of which are incorporated herein by reference.

Non-limiting examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and salicylic acid and the like.

Non-limiting examples of a pharmaceutically acceptable base addition salts include those formed when an acidic proton present in the parent compound is replaced by an ionic form of sodium, potassium, lithium, ammonium, calcium, magnesium, iron, zinc, copper, manganese, aluminum salts and the like. Preferable salts are the ammonium, potassium, sodium, calcium, and magnesium salts. The aforementioned salts can be substituted, where possible. Non-limiting examples of substituted salts include alkylated ammonium salts, such as triethylammonium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins. Examples of organic bases include isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, polyamine resins, and the like. Exemplary organic bases are isopropylamine, diethylamine, ethanolamine, trimethylamine, dicyclohexylamine, choline, and caffeine.

All of the compounds disclosed herein include either their free base form or their pharmaceutically acceptable salts whether it is stated in the specification that these compounds can exist as their pharmaceutically acceptable salt or not.

The term "SMDC" refers to a small molecule drug conjugate. SMDCs are drugs that are covalently attached to another chemical moiety for specific applications.

"Treating" or "treatment" of a disease, disorder or syndrome, as used herein, includes (i) preventing the disease, disorder or syndrome from occurring in a human, i.e. causing the clinical symptoms of the disease, disorder or syndrome not to develop in an animal that can be exposed to or predisposed to the disease, disorder or syndrome but does not yet experience or display symptoms of the disease, disorder or syndrome; (ii) inhibiting the disease, disorder or syndrome, i.e., arresting its development; and (iii) relieving the disease, disorder or syndrome, i.e., causing regression of the disease, disorder or syndrome. As is known in the art, adjustments for systemic versus localized delivery, age, body weight, general health, sex, diet, time of administration, drug interaction and the severity of the condition can be necessary, and will be ascertainable with routine experimentation by one of ordinary skill in the art.

All of the compounds disclosed herein can exist as single stereoisomers (including single enantiomers and single diastereomers), racemates, mixtures of enantiomers and diastereomers and polymorphs. Stereoisomers of the compounds in this disclosure include geometric isomers and optical isomers, such as atropisomers. The compounds disclosed herein can also exist as geometric isomers. All such single stereoisomers, racemates and mixtures thereof, and geometric isomers are intended to be within the scope of the compounds disclosed herein.

In addition, the compounds of this disclosure can exist in unsolvated as well as solvated forms with pharmaceutically acceptable solvents such as water, ethanol, and the like. In general, the solvated forms are considered equivalent to the unsolvated forms for the purposes of the compounds of this disclosure.

By alkyl is meant herein a saturated hydrocarbyl radical, which may be straight-chain, cyclic or branched (typically straight-chain unless the context dictates to the contrary). Where an alkyl group has one or more sites of unsaturation, these may be constituted by carbon-carbon double bonds or carbon-carbon triple bonds. Where an alkyl group comprises a carbon-carbon double bond this provides an alkenyl group; the presence of a carbon-carbon triple bond provides an alkynyl group. In one example, alkyl, alkenyl and alkynyl groups will comprise from 1 to 25 carbon atoms. In another example, alkyl, alkenyl and alkynyl groups will comprise from 1 to 10 carbon atoms. In another example, alkyl, alkenyl and alkynyl groups will comprise from 1 to 6 carbon atoms. In another example, alkyl, alkenyl and alkynyl groups will comprise from 1 to 4 carbon atoms. In another example, alkyl, alkenyl and alkynyl groups will comprise from 1 to 3 carbon atoms. In another example, alkyl, alkenyl and alkynyl groups will comprise from 1 to 2 carbon atoms. In another example, alkyl groups will comprise 1 carbon atom. It is understood that the lower limit in alkenyl and alkynyl groups is 2 carbon atoms and in cycloalkyl groups 3 carbon atoms.

Alkyl, alkenyl or alkynyl groups may be substituted, for example once, twice, or three times, e.g. once, i.e. formally replacing one or more hydrogen atoms of the alkyl group. Examples of such substituents are halo (e.g. fluoro, chloro, bromo and iodo), aryl, hydroxy, nitro, amino, alkoxy, alkylthio, carboxy, cyano, thio, formyl, ester, acyl, thioacyl, amido, sulfonamido, carbamate and the like.

—($C_3$-$C_5$)alkenylene-, is meant to be a bivalent alkene group from 3 to 5 carbons in length, which may be attached to another atom such as in —($C_3$-$C_5$)alkenylene-O— or —($C_3$-$C_5$)alkenylene-O—C(O)N(H)—. —($C_3$-$C_5$)alkenylene- may be optionally substituted with one to four $C_1$-$C_6$ alkyl groups.

By carboxy is meant herein the functional group $CO_2H$, which may be in deprotonated form ($CO_2^-$).

Halo or halogen are each fluoro, bromo, chloro or iodo.

By acyl and thioacyl are meant the functional groups of formulae —C(O)-alkyl or —C(S)-alkyl respectively, where alkyl is as defined hereinbefore.

By ester is meant a functional group comprising the moiety —OC(=O)—.

By amido is meant a functional group comprising the moiety —N(H)C(=O)—, in which Each hydrogen atom depicted may be replaced with alkyl or aryl.

By carbamate is meant a functional group comprising the moiety —N(H)C(=O)O—, in which each hydrogen atom depicted may be replaced with alkyl or aryl.

By sulfonamido is meant a functional group comprising the moiety —SO$_2$N(H)$_2$—, in which each hydrogen atom depicted may be replaced independently with alkyl or aryl.

Alkyloxy (synonymous with alkoxy) and alkylthio moieties are of the formulae —O-alkyl and —S-alkyl respectively, where alkyl is as defined hereinbefore.

Et$_3$NH$^+$ refers to the structure

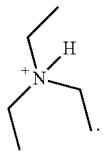

Alkenyloxy, alkynyloxy, alkenylthio and alkynylthio are of the formulae —O-alkenyl, —O-alkynyl, —S-alkenyl and S-alkynyl, where alkenyl and alkynyl are as defined hereinbefore.

Deuterated alkyl is meant herein as an alkyl group as defined herein, wherein one or more hydrogen atoms of the alkyl group is replaced with deuterium. When more than one deuterated alkyl group exists in a molecule disclosed herein, each deuterated C$_1$-C$_6$ alky group can be the same or different.

Deuterated C$_1$-C$_6$ alkyl is meant herein as a —C$_1$-C$_6$ alkyl group wherein one or more hydrogen atoms of the C$_1$-C$_6$ alkyl group is replaced with deuterium. When more than one deuterated C$_1$-C$_6$ alkyl group exists in a molecule disclosed herein, each deuterated C$_1$-C$_6$ alkyl group can be the same or different.

Deuterated alkoxy is meant herein as an —O-alkyl group, wherein one or more hydrogen atoms of the alkyl group is replaced with deuterium. When more than one deuterated alkyl group exists in a molecule disclosed herein, each deuterated C$_1$-C$_6$ alkyl group can be the same or different.

Deuterated C$_1$-C$_6$ alkoxy is meant herein as O—C$_1$-C$_6$ alkyl group wherein one or more hydrogen atoms of the C$_1$-C$_6$ alkyl group is replaced with deuterium. When more than one deuterated C$_1$-C$_6$ alkyl group exists in a molecule disclosed herein, Each deuterated C$_1$-C$_6$ alkyl group can be the same or different.

Deuterated methoxy is meant herein as —OCD$_{1-3}$. It is to be understood that —OCD$_{1-3}$ is meant to include either —OCH$_2$D, —OCHD$_2$, or —OCD$_3$. When more than one deuterated methoxy group exists in a molecule disclosed herein, each deuterated methoxy group can be the same or different.

By amino group is meant herein a group of the formula —N(R)$_2$ in which each R is independently hydrogen, alkyl or aryl. For example, R can be an unsaturated, unsubstituted C$_{1-6}$ alkyl such as methyl or ethyl. In another example, the two R groups attached to the nitrogen atom N are connected to form a ring. One example where the two Rs attached to nitrogen atom N are connected is whereby —R—R— forms an alkylene diradical, derived formally from an alkane from which two hydrogen atoms have been abstracted, typically from terminal carbon atoms, whereby to form a ring together with the nitrogen atom of the amine. As is known the diradical in cyclic amines need not necessarily be alkylene: morpholine (in which —R—R— is —(CH$_2$)$_2$O(CH$_2$)$_2$—) is one such example from which a cyclic amino substituent may be prepared.

References to amino herein are also to be understood as embracing within their ambit quaternised or protonated derivatives of the amines resultant from compounds comprising such amino groups. Examples of the latter may be understood to be salts such as hydrochloride salts.

By aryl is meant herein a radical formed formally by abstraction of a hydrogen atom from an aromatic compound.

Arylene diradicals are derived from aromatic moieties, formally, by abstraction of two hydrogen atoms, and may be, unless the context specifically dictates to the contrary, monocyclic, for example, phenylene. As known to those skilled in the art, heteroaromatic moieties are a subset of aromatic moieties that comprise one or more heteroatoms, typically O, N or S, in place of one or more carbon atoms and any hydrogen atoms attached thereto.

Exemplary heteroaromatic moieties include pyridine, furan, pyrrole, thiophene and pyrimidine. Further examples of heteroaromatic rings include pyridyl; pyridazine (in which 2 nitrogen atoms are adjacent in an aromatic 6-membered ring); pyrazine (in which 2 nitrogens are 1,4-disposed in a 6-membered aromatic ring); pyrimidine (in which 2 nitrogen atoms are 1,3-disposed in a 6-membered aromatic ring); and 1,3,5-triazine (in which 3 nitrogen atoms are 1,3,5-disposed in a 6-membered aromatic ring).

Aryl or arylene radicals may be substituted one or more times with an electron-withdrawing group.

A phosphoric acid derivative of gemcitabine includes compounds having the following structures:

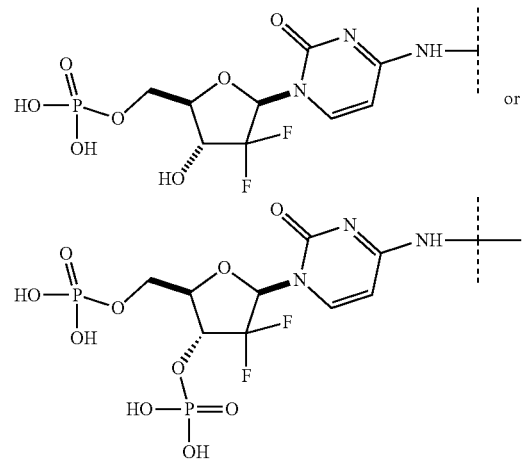

Non-limiting examples of salt forms of phosphoric acid derivative of gemcitabine include sodium salts, potassium salts, calcium salts, triethylamine salts, and ammonium salts.

Non-limiting examples of electron withdrawing groups include cyano (—CN), haloalkyl, amide, nitro, keto (—COR), alkenyl, alkynyl, quaternary amino (—N$^+$R$_3$), ester, amido (—C(O)NR$_2$), N-connected amido (—NR—C(=O)—R), N-connected sulfonamido (—NR—S(=O)$_2$R), sulfoxy (—S(=O)$_2$OH), sulfonate (S(=O)$_2$OR), sulfonyl (S(=O)$_2$R) and sulfonamide (—S(=O)$_2$—NR$_2$), where Each R is independently selected from a C$_1$-C$_6$ alkyl group, a C$_3$-C$_{20}$ heterocyclic group, or a C$_3$-C$_{20}$ aryl group, wherein the C$_1$-C$_6$ alkyl group can be substituted with one or more groups selected from ether, amino, mono- or di-substituted amino, cyclic C$_1$-C$_5$ alkylamino, imidazolyl, C$_1$-C$_6$ alkylpiperazinyl, morpholino, thiol, thioether, tetrazole, carboxylic acid, ester, amide, mono- or di-substituted amide, N-connected amide (—NR—C(=O)—R), N-connected sulfonamide (—NR—S(=O)$_2$—R), sulfoxy (—S(=O)$_2$OH), sulfonate (S(=O)$_2$OR), sulfonyl (S(=O)$_2$R), sulfoxy (S(=O)OH), sulfinate (S(=O)OR), sulfinyl (S(=O)R), phosphonooxy(-OP(=O)(OH)$_2$), phosphate (OP(=O)(OR)$_2$), and sulfonamide (—S(=O)$_2$—NR$_2$), wherein each R is independently selected from a $C_1$-$C_6$ alkyl group, a $C_3$-$C_{20}$ heterocyclic group, or a $C_3$-$C_{20}$ aryl group. In another example, Each R is a $C_1$-$C_6$ alkyl group (based on the definition of alkyl hereinabove $C_1$-$C_6$ alkyl group includes unsubstituted $C_1$-$C_6$ alkoxy and substituted $C_1$-$C_6$ alkoxy groups). In another example, Each R is a $C_1$-$C_6$ alkyl, unsubstituted $C_1$-$C_6$ alkoxy or substituted $C_1$-$C_6$ alkoxy, wherein the substituted alkyl or substituted alkoxy are substituted with one or more groups selected from ether, —OH amino, mono- or di-substituted amino, cyclic $C_1$-$C_5$ alkylamino, imidazolyl, $C_1$-$C_6$ alkylpiperazinyl, morpholino, thiol, thioether, tetrazole, carboxylic acid, ester, amide, mono- or di-substituted amide, N-connected amide (—NR—C(=O)—R), N-connected sulfonamide (—NR—S(=O)$_2$—R), sulfoxy (—S(=O)$_2$OH), sulfonate (S(=O)$_2$OR), sulfonyl (S(=O)$_2$R), sulfoxy (S(=O)OH), sulfinate (S(=O)OR), sulfinyl (S(=O)R), phosphonooxy(-OP(=O)(OH)$_2$), phosphate (OP(=O)(OR)$_2$), and sulfonamide (—S(=O)$_2$—NR$_2$), wherein each R is independently selected from a $C_1$-$C_6$ alkyl group, a $C_3$-$C_{20}$ heterocyclic group, or a $C_3$-$C_{20}$ aryl group.

The make-up and variability of these three regions: the trigger, linker and Effector regions—of the compounds of formula (I) are now described.

The trigger region of the compounds of formula (I) generally comprises a conjugated bicyclic moiety comprising a six membered ring fused to a five membered ring.

Without being bound by theory, it is believed that the activity of the compounds of formula (I) as substrates for hydroxylation, e.g. effected by CYP1B1, is achieved in part by the structure of the trigger moiety being susceptible to hydroxylation leading to spontaneous collapse of the compound by an elimination process, either a 1,4-, a 1,6- or a 1,8-elimination, depending upon at which position hydroxylation takes place as shown in FIGS. 1$a$-1$d$. In addition, —OCH$_3$ would normally be metabolized via hydroxylation and subsequent O-dealkylation. However, deuterated methoxy may confer enhanced stability to CYP based hydroxylation and O-dealkylation via the kinetic isotope effect. Adjacent aromatic C—H bonds hence become sites for CYP based hydroxylation, which lead to spontaneous collapse of the compound via 1,4-, 1,6- or 1,8-elimination.

It will be noted from the structure of the compounds of formula (I) that, by virtue of the conjugation of carbon atoms, that any of the three mechanisms for spontaneous breakdown of the compound may take place independently of the nature of the substituents on the trigger region. Thus a wide variety to the nature of this region of the compounds of formula (I) may be tolerated as discussed below.

In one embodiment of the compound of formula (I), $Y^2$ is C and $Y^3$ is C(H). In another embodiment of the compound of formula (I), Each of $Y^3$ and $Y^4$ are C(H). In another embodiment of the compound of formula (I), $Y^2$ is C, and $Y^3$ and $Y^4$ are C(H). In another embodiment of the compound of formula (I), $Y^2$ is C, and $Y^1$, $Y^3$ and $Y^4$ are C(H).

In another embodiment of the compound of formula (I), $Y^1$ is N, $Y^2$ is C, $Y^3$ is C(H), $Y^4$ is C(H), and $Y^5$ is S. In another embodiment of the compound of formula (I), $Y^1$ is N, $Y^2$ is N, $Y^3$ is C(H), $Y^4$ is C(H), and $Y^5$ is C(H). In another embodiment of the compound of formula (I), $Y^1$ is C(H), $Y^2$ is C, $Y^3$ is C(H), $Y^4$ is C(H), and $Y^5$ is N(CH$_3$). In another embodiment of the compound of formula (I), $Y^1$ is C(H), $Y^2$ is N, $Y^3$ is C(H), $Y^4$ is C(H), and $Y^5$ is N. In another embodiment of the compound of formula (I), $Y^1$ is N, $Y^2$ is N, $Y^3$ is C(H), $Y^4$ is C(H), and $Y^5$ is N. In another embodiment of the compound of formula (I), $Y^1$ is C, $Y^2$ is C, $Y^3$ is C(H), $Y^4$ is C(H), and $Y^5$ is S. In another embodiment of the compound of formula (I), $Y^1$ is N, $Y^2$ is C, $Y^3$ is C(H), $Y^4$ is C(H), and $Y^5$ is O. In another embodiment of the compound of formula (I), $Y^1$ is C(H), $Y^2$ is C, $Y^3$ is C(H), $Y^4$ is C(H), and $Y^5$ is O.

The substituents $Z^1$, $Z^2$ and $Z^4$ may be generally as described herein. However, at least one of these moieties is a hydrogen atom so as to allow a site for hydroxylation of the compound. In some embodiments of the compound of formula (I), either $Z^2$ or $Z^4$ is hydrogen.

In other embodiments $Z^2$ and $Z^4$ is hydrogen. In either of these embodiments, that in which $Z^2$ or $Z^4$ is a hydrogen atom or in which both $Z^2$ and $Z^4$ are hydrogen atoms or in which neither $Z^2$ or $Z^4$ is a hydrogen atom, $Z^1$ may be hydrogen. In certain embodiments of the compound of formula (I), Each of $Z^1$, $Z^2$ and $Z^4$ is a hydrogen atom.

In another embodiment of formula (I), $Z^3$ is selected from hydrogen alkyl, deuterated alkyl, $C_{1-6}$ alkoxy, deuterated $C_{1-6}$ alkoxy, halo, alkenyl, alkynyl, aryl, aralkyl, alkyloxy, alkenyloxy, alkynyloxy, aryloxy, aralkyloxy, alkylthioxy, alkenylthioxy, alkynylthioxy, arylthioxy, aralkylthioxy, amino, hydroxy, thio, carboxy, formyl, nitro and cyano, wherein each alkyl, alkenyl, alkynyl, alkoxy and aryl moiety are independently optionally substituted with 1-3 halo. In another embodiment of formula (I), $Z^3$ is halo. In another embodiment of formula (I), $Z^3$ is methyl. In another embodiment of formula (I), $Z^3$ is methoxy. In another embodiment of formula (I), $Z^3$ is bromo.

In another embodiment of formula (I), $Z^5$ is selected from hydrogen alkyl, deuterated alkyl, $C_{1-6}$ alkoxy, deuterated $C_{1-6}$ alkoxy, halo, alkenyl, alkynyl, aryl, aralkyl, alkyloxy, alkenyloxy, alkynyloxy, aryloxy, aralkyloxy, alkylthioxy, alkenylthioxy, alkynylthioxy, arylthioxy, aralkylthioxy, amino, hydroxy, thio, carboxy, formyl, nitro and cyano. In another embodiment of formula (I), $Z^5$ is halo. In another embodiment of formula (I), $Z^5$ is methyl. In another embodiment of formula (I), $Z^5$ is methoxy. In another embodiment of formula (I), $Z^5$ is bromo.

In another embodiment of formula (I), $Z^3$ and $Z^5$ are each selected from hydrogen alkyl, deuterated alkyl, $C_1$-$C_6$ alkoxy, deuterated $C_1$-$C_6$ alkoxy, halo, alkenyl, alkynyl, aryl, aralkyl, alkyloxy, alkenyloxy, alkynyloxy, aryloxy, aralkyloxy, alkylthioxy, alkenylthioxy, alkynylthioxy, arylthioxy, aralkylthioxy, amino, hydroxy, thio, halo, carboxy, formyl, nitro and cyano, wherein each alkyl, alkenyl, alkynyl, alkoxy and aryl moiety are independently optionally substituted with 1-3 halo. In another embodiment of formula (I), $Z^3$ and $Z^5$ are each selected from alkyl, deuterated alkyl, $C_1$-$C_6$ alkoxy, deuterated $C_1$-$C_6$ alkoxy, alkenyl, alkynyl, aryl, aralkyl, alkyloxy, alkenyloxy, alkynyloxy, aryloxy, aralkyloxy, alkylthioxy, alkenylthioxy, alkynylthioxy, arylthioxy, aralkylthioxy, amino, hydroxy, thio, halo, carboxy, formyl, nitro and cyano, wherein each alkyl, alkenyl, alkynyl, alkoxy and aryl moiety are independently optionally substituted with 1-3 halo. In another embodiment of formula (I), $Z^3$ and $Z^5$ are each deuterated $C_1$-$C_6$ alkoxy. In another embodiment of formula (I), $Z^3$ and $Z^5$ are each $C_1$-$C_6$ alkoxy. In another embodiment of formula (I), $Z^3$ and $Z^5$ are each $C_1$-$C_6$ alkyl. In another embodiment of formula (I), $Z^3$ and $Z^5$ are each $C_1$-$C_3$ alkoxy. In another embodiment of formula (I), $Z^3$ and $Z^5$ are each $C_1$-$C_3$ alkyl. In another embodiment of formula (I), $Z^3$ and $Z^5$ are each hydrogen. In another embodiment of formula (I), $Z^3$ and $Z^5$ are each halo. In another embodiment of formula (I), $Z^3$ and $Z^5$ are each bromo. In another embodiment of formula (I), $Z^3$ and $Z^5$ are each deuterated methoxy. In another embodiment of formula (I), $Z^3$ and $Z^5$ are each methoxy. In another embodiment of formula (I), $Z^3$ and $Z^5$ are each methyl. In another embodiment of formula (I), $Z^3$ and $Z^5$ are each —$OCD_{1-3}$. In another embodiment of formula (I), $Z^3$ and $Z^5$ are each —$OCD_3$.

In another embodiment of formula (I), $Z^3$ and $Z^5$ are each independently selected from halo, methyl, methoxy, or deuterated methoxy.

One aspect of the invention relates to a compound of formula (I):

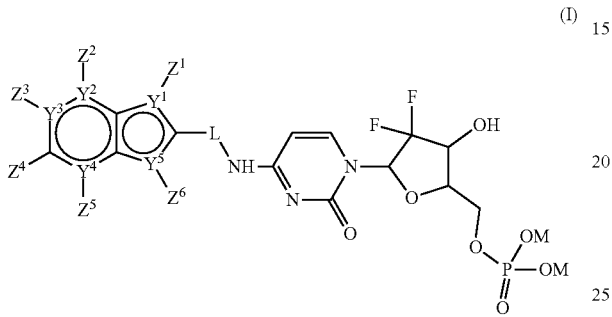

(I)

or a pharmaceutically acceptable salt, ester, solvate, or stereoisomer thereof, wherein:

-L- is defined as: —$(C_1-C_5)$alkylene-O—C(O)—, —$(C_3-C_5)$alkenylene-O—,

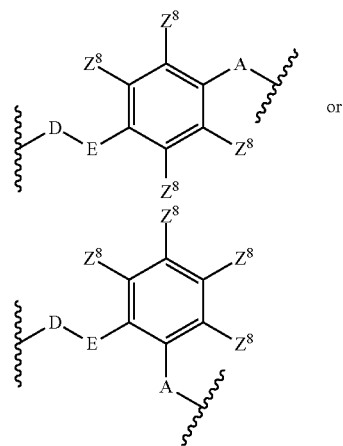

A is —$(C_1-C_5)$alkylene-O—C(O)—;
E is —O—, —O—C(O)N(H)—, —O—C(S)N(H)—, —S— or —S—C(O)N(H)—;
D is —$(C_1-C_5)$alkylene- or —$(C_3-C_5)$alkenylene-;
$Y^1$ is C=C, carbon or nitrogen, wherein if $Y^1$ is nitrogen, $Z^1$ is absent;
Each of $Y^4$ and $Y^5$ is independently carbon or nitrogen, wherein if $Y^3$ is nitrogen, $Z^3$ is absent and if $Y^4$ is nitrogen, $Z^5$ is absent;
$Y^2$ is C or N wherein if $Y^2$ is nitrogen, $Z^2$ is absent;
$Y^5$ is an oxygen, carbon, nitrogen or a sulfur atom, wherein $Z^6$ is absent when $Y^5$ is an oxygen, or a sulfur atom;
$Z^3$, $Z^4$, and $Z^5$ are each independently selected from hydrogen, alkyl, deuterated alkyl, $C_{1-6}$ alkoxy, deuterated $C_{1-6}$ alkoxy, alkenyl, alkynyl, aryl, aralkyl, alkyloxy, alkenyloxy, alkynyloxy, aryloxy, aralkyloxy, alkylthioxy, alkenylthioxy, alkynylthioxy, arylthioxy, aralkylthioxy, amino, hydroxy, thio, halo, carboxy, formyl, nitro and cyano, wherein each alkyl, alkenyl, alkynyl, alkoxy, and aryl moiety is independently optionally substituted with 1-3 halo;
provided that at least one of $Z^1$, $Z^2$ or $Z^4$ is H;
$Z^6$ is selected from hydrogen, alkyl, alkenyl, alkynyl, aryl and aralkyl, wherein each alkyl, alkenyl, alkynyl, alkoxy, and aryl moiety is independently optionally substituted with 1-3 halo;
Each $Z^8$ is independently hydrogen, unsubstituted $C_1-C_6$ alkyl, substituted $C_1-C_6$ alkyl, unsubstituted $C_1-C_6$ alkoxy, unsubstituted deuterated $C_1-C_6$ alkoxy, substituted $C_1-C_6$ alkoxy, and substituted deuterated $C_1-C_6$ alkoxy where the substituted alkyl, alkoxy and deuterated alkoxy are substituted with one or more groups selected from amino, mono- or di-substituted amino, cyclic $C_1-C_5$ alkylamino, imidazolyl, $C_1-C_6$ alkylpiperazinyl, morpholino, thiol, thioether, tetrazole, carboxylic acid, ester, amido, mono- or di-substituted amido, N-connected amide, N-connected sulfonamide, sulfoxy, sulfonate, sulfonyl, sulfoxy, sulfinate, sulfinyl, phosphonooxy, phosphate or sulfonamide, wherein each alkyl, alkenyl, alkynyl, alkoxy, and aryl is optionally substituted with 1-3 halo; and In another embodiment of formula (I), or a pharmaceutically acceptable salt, ester, amide, solvate, or stereoisomer thereof, $Y^3$ and $Y^4$ are each carbon.

In another embodiment of formula (I), or a pharmaceutically acceptable salt, ester, amide, solvate, or stereoisomer thereof, $Z^3$, $Z^4$ and $Z^5$ are each selected from halo, unsubstituted $C_1-C_3$ alkyl, substituted $C_1-C_3$ alkyl, unsubstituted $C_1-C_3$ alkoxy, substituted $C_1-C_3$ alkoxy, unsubstituted deuterated $C_1-C_3$ alkoxy, or substituted $C_1-C_3$ alkoxy, wherein each alkyl and alkoxy moiety can be independently substituted with 1-3 halo.

In another embodiment of formula (I), or a pharmaceutically acceptable salt, ester, amide, solvate, or stereoisomer thereof, $Z^3$, $Z^4$ and $Z^5$ are each selected from bromo, chloro, fluoro, methyl optionally substituted with 1-3 halo, deuterated methyl, methoxy optionally substituted with 1-3 halo, or deuterated methoxy.

Another embodiment of formula (I) relates to a compound having formula (Ia):

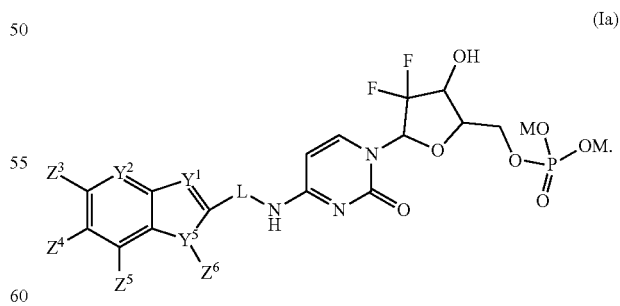

(Ia)

or a pharmaceutically acceptable salt, ester, solvate, or stereoisomer thereof,
wherein L, $Y^1$, $Y^2$, $Y^5$, $Z^3$, $Z^4$, $Z^5$, $Z^6$ are as defined in any of embodiments of formula (I).

Other embodiments of formula (I) and (Ia) relate to a compound having one or more of formulae (Ib-i), (Ib-ii), (Ib-iii), (Ib-iv), (Ib-v), (Ib-vi), (Ib-vii), (Ib-viii), (Ib-ix), (Ib-x), (Ib-xi), (Ib-xii), (Ib-xiii), (Ib-xiv), (Ib-xv), (Ib-xvi), (Ib-xvii) or (Ib-xviii):

(Ib-i)
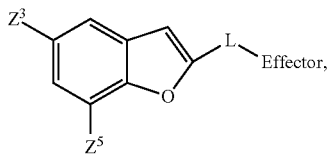

(Ib-ii)
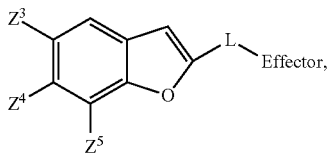

(Ib-iii)
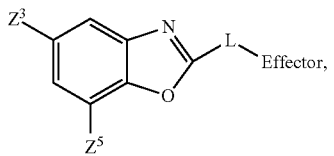

(Ib-iv)
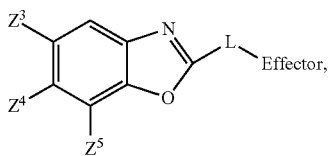

(Ib-v)
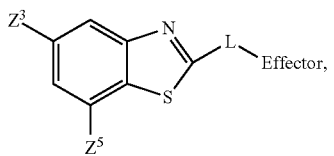

(Ib-vi)
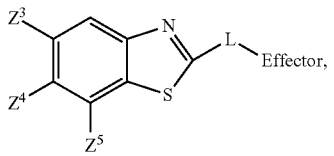

(Ib-vii)
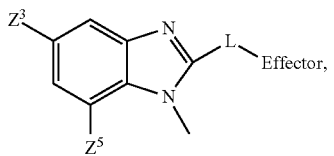

(Ib-viii)
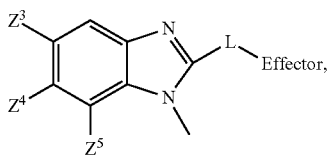

(Ib-ix)
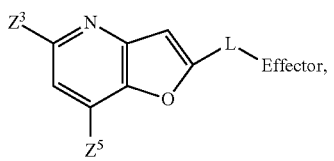

-continued (Ib-x)
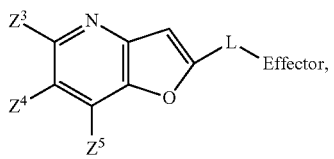

(Ib-xi)
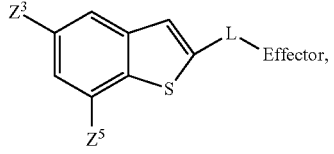

(Ib-xii)
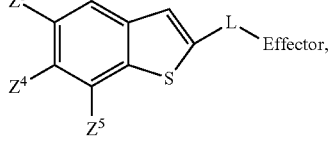

(Ib-xiii)
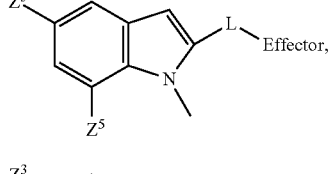

(Ib-xiv)
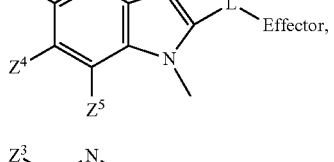

(Ib-xv)
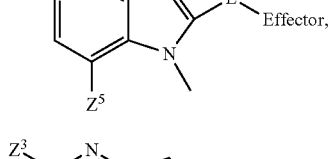

(Ib-xvi)
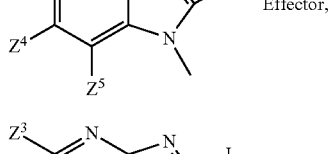

(Ib-xvii)
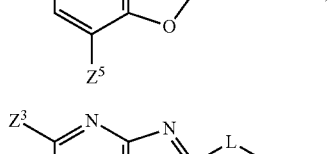

(Ib-xviii)

or a pharmaceutically acceptable salt, ester, solvate, or stereoisomer of any of the above formulae, wherein:

$Z^3$ and $Z^5$ are each independently halo, methyl optionally substituted with 1-3 halo, methoxy optionally substituted with 1-3 halo or deuterated methoxy;

$Z^4$, when present, is halo, methyl optionally substituted with 1-3 halo, methoxy optionally substituted with 1-3 halo or deuterated methoxy;

L-Effector is: —($C_1$-$C_3$)alkylene-O—C(O)-Effector,

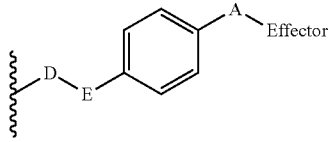

or

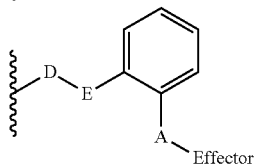

D is —($C_1$-$C_3$)alkylene-;
E is —O—, —O—C(O)N(H)—, —O—C(S)N(H)—, —S— or —S—C(O)N(H)—;
A is —C(H)$_2$—O—C(O)—; and
Effector is part of a (i) phosphoric acid derivative of gemcitabine or (ii) a salt form of a phosphoric acid derivative of gemcitabine.

In other embodiments of the compounds having formulae (I), (Ia), (Ib-i), (Ib-ii), (Ib-iii), (Ib-iv), (Ib-v), (Ib-vi), (Ib-vii), (Ib-viii), (Ib-ix), (Ib-x), (Ib-xi), (Ib-xii), (Ib-xiii), (Ib-xiv), (Ib-xv), (Ib-xvi), (Ib-xvii), or (Ib-xviii), or a pharmaceutically acceptable salt, ester, amide, solvate, or stereoisomer thereof, the linker region (L) is —C(H)$_2$—O—C(O)—.

L represents the linking region which is described in more detail below. Each of the following embodiments of L (the linking region) can be separate embodiments for each of the trigger regions and Effectors, including any combinations of trigger regions and Effector, wherever it is chemically possible. Various embodiments of the linker region are now described.

In other embodiments of formula (I), (Ia), (Ib-i), (Ib-ii), (Ib-iii), (Ib-iv), (Ib-v), (Ib-vi), (Ib-vii), (Ib-viii), (Ib-ix), (Ib-x), (Ib-xi), (Ib-xii), (Ib-xiii), (Ib-xiv), (Ib-xv), (Ib-xvi), (Ib-xvii), or (Ib-xviii), including subembodiments of Each of these formulae described above, the linker region (L) is —($C_1$-$C_5$)alkylene-O—C(O)—.

In other embodiments of formula (I), (Ia), (Ib-i), (Ib-ii), (Ib-iii), (Ib-iv), (Ib-v), (Ib-vi), (Ib-vii), (Ib-viii), (Ib-ix), (Ib-x), (Ib-xi), (Ib-xii), (Ib-xiii), (Ib-xiv), (Ib-xv), (Ib-xvi), (Ib-xvii), or (Ib-xviii), including subembodiments of Each of these formulae described above, the linker region (L) is —($C_3$-$C_5$)alkenylene-O—C(O)—.

In other embodiments of formula (I), (Ia), (Ib-i), (Ib-ii), (Ib-iii), (Ib-iv), (Ib-v), (Ib-vi), (Ib-vii), (Ib-viii), (Ib-ix), (Ib-x), (Ib-xi), (Ib-xii), (Ib-xiii), (Ib-xiv), (Ib-xv), (Ib-xvi), (Ib-xvii), or (Ib-xviii), including subembodiments of Each of these formulae described above, the linker region (L) is

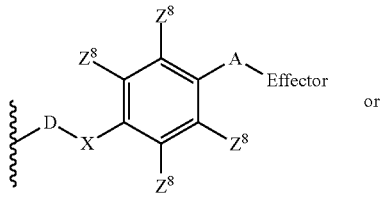

or

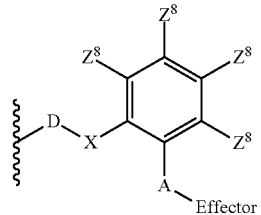

wherein:
A is —($C_1$-$C_5$)alkylene-O—C(O);
X is —O—;
D is —($C_1$-$C_5$)alkylene- or —($C_3$-$C_5$)alkenylene-;
and each $Z^8$ is as defined in any of the embodiments in this specification.

In other embodiments of formula (I), (Ia), (Ib-i), (Ib-ii), (Ib-iii), (Ib-iv), (Ib-v), (Ib-vi), (Ib-vii), (Ib-viii), (Ib-ix), (Ib-x), (Ib-xi), (Ib-xii), (Ib-xiii), (Ib-xiv), (Ib-xv), (Ib-xvi), (Ib-xvii), or (Ib-xviii), including subembodiments of each of these formulae described above, the linker region (L) is

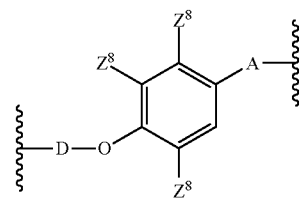

wherein:
A is —($C_1$-$C_2$)alkylene-O—C(O)—;
X is —O—;
D is —($C_1$-$C_2$)alkylene- or —($C_3$-$C_4$)alkenylene-;
and each $Z^8$ is as defined in any of the embodiments in this specification.

In other embodiments of formula (I), (Ia), (Ib-i), (Ib-ii), (Ib-iii), (Ib-iv), (Ib-v), (Ib-vi), (Ib-vii), (Ib-viii), (Ib-ix), (Ib-x), (Ib-xi), (Ib-xii), (Ib-xiii), (Ib-xiv), (Ib-xv), (Ib-xvi), (Ib-xvii), or (Ib-xviii), including subembodiments of Each of these formulae described above, the linker region (L) is

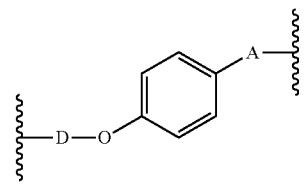

wherein:
A is —($C_1$-$C_2$)alkylene-O—C(O)—;

In other embodiments of formula (I), (Ia), (Ib-i), (Ib-ii), (Ib-iii), (Ib-iv), (Ib-v), (Ib-vi), (Ib-vii), (Ib-viii), (Ib-ix), (Ib-x), (Ib-xi), (Ib-xii), (Ib-xiii), (Ib-xiv), (Ib-xv), (Ib-xvi), (Ib-xvii), or (Ib-xviii), including subembodiments of each of these formulae described above, the linker region (L) is

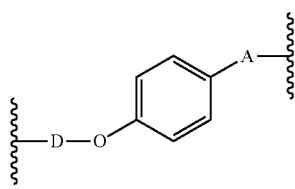

wherein

A is —(C$_1$-C$_2$)alkylene-O—C(O)—; and

D is —CH$_2$— or —CH$_2$—C(H)=C(H—.

In other embodiments of any of formulae (Ic-i), (Ic-ii), (Ic-iii), (Ic-iv), (Ic-v), (Ic-vi), (Ic-vii), (Ic-viii), (Ic-ix), (Ic-x), (Ic-xi), (Ic-xii), (Ic-xiii), (Ic-xiv), (Ic-xv), (Ic-xvi), (Ic-xvii), (Ic-xviii), (Ic-xix), or (Ic-xx), or a pharmaceutically acceptable salt, ester, amide, solvate, or stereoisomer thereof:

$R^b$ is —(C$_1$-C$_5$)alkyl optionally substituted with heterocycloalkyl, or alxoxyaryl;

$R^z$ is —(C$_1$-C$_5$)alkyl optionally substituted with heterocycloalkyl or aryl; and M is —O$^-$Na$^+$, —O$^-$Et$_3$NH$^+$, —O$^-$K$^+$ or —O$^-$NH$_4^+$.

In other embodiments of any of formulae (Ic-i), (Ic-ii), (Ic-iii), (Ic-iv), (Ic-v), (Ic-vi), (Ic-vii), (Ic-viii), (Ic-ix), (Ic-x), (Ic-xi), (Ic-xii), (Ic-xiii), (Ic-xiv), (Ic-xv), (Ic-xvi), (Ic-xvii), (Ic-xviii), (Ic-xix), or (Ic-xx), or a pharmaceutically acceptable salt, ester, amide, solvate, or stereoisomer thereof:

$R^b$ is —(C$_1$-C$_5$)alkyl optionally substituted with heterocycloalkyl, or alxoxyaryl;

$R^z$ is —(C$_1$-C$_5$)alkyl optionally substituted with heterocycloalkyl or aryl; and M is Et$_3$NH$^+$.

In other embodiments of any of formulae (Ic-i), (Ic-ii), (Ic-iii), (Ic-iv), (Ic-v), (Ic-vi), (Ic-vii), (Ic-viii), (Ic-ix), (Ic-x), (Ic-xi), (Ic-xii), (Ic-xiii), (Ic-xiv), (Ic-xv), (Ic-xvi), (Ic-xvii), (Ic-xviii), (Ic-xix), or (Ic-xx), or a pharmaceutically acceptable salt, ester, amide, solvate, or stereoisomer thereof:

$R^b$ is —(C$_1$-C$_5$)alkyl optionally substituted with heterocycloalkyl, or alxoxyaryl;

$R^z$ is —(C$_1$-C$_5$)alkyl optionally substituted with heterocycloalkyl or aryl; and M is —O—(C$_1$-C$_5$)alkyl-heterocycloalkyl.

In other embodiments of formula (I), (Ia), (Ib-i), (Ib-ii), (Ib-iii), (Ib-iv), (Ib-v), (Ib-vi), (Ib-vii), (Ib-viii), (Ib-ix), (Ib-x), (Ib-xi), (Ib-xii), (Ib-xiii), (Ib-xiv), (Ib-xv), (Ib-xvi), (Ib-xvii), (Ib-xviii), including subembodiments of each of these formulae described above, or a pharmaceutically acceptable salt, ester, amide, solvate, or stereoisomer thereof, $Z^3$, $Z^5$ and $Z^4$, when present, are each methoxy or deuterated methoxy.

In other embodiments of formula (I), (Ia), (Ib-i), (Ib-ii), (Ib-iii), (Ib-iv), (Ib-v), (Ib-vi), (Ib-vii), (Ib-viii), (Ib-ix), (Ib-x), (Ib-xi), (Ib-xii), (Ib-xiii), (Ib-xiv), (Ib-xv), (Ib-xvi), (Ib-xvii), or (Ib-xviii), including subembodiments of Each of these formulae described above, or a pharmaceutically acceptable salt, ester, amide, solvate, or stereoisomer thereof, $Z^3$, $Z^5$ and $Z^4$, when present, are each methoxy optionally substituted with 1-3 halo, or deuterated methoxy, and Effector is as defined in any of the embodiments described in the specification.

In other embodiments of formula (I), (Ia), (Ib-i), (Ib-ii), (Ib-iii), (Ib-iv), (Ib-v), (Ib-vi), (Ib-vii), (Ib-viii), (Ib-ix), (Ib-x), (Ib-xi), (Ib-xii), (Ib-xiii), (Ib-xiv), (Ib-xv), (Ib-xvi), (Ib-xvii), (Ib-xviii), including subembodiments of each of these formulae described above, or a pharmaceutically acceptable salt, ester, amide, solvate, or stereoisomer thereof, $Z^3$ and $Z^5$ are each independently bromo or fluoro, and $Z^4$, when present, is methoxy optionally substituted with 1-3 halo, or deuterated methoxy.

In other embodiments of formula (I), (Ia), (Ib-i), (Ib-ii), (Ib-iii), (Ib-iv), (Ib-v), (Ib-vi), (Ib-vii), (Ib-viii), (Ib-ix), (Ib-x), (Ib-xi), (Ib-xii), (Ib-xiii), (Ib-xiv), (Ib-xv), (Ib-xvi), (Ib-xvii), (Ib-xviii), including subembodiments of each of these formulae described above, or a pharmaceutically acceptable salt, ester, amide, solvate, or stereoisomer thereof, $Z^3$ and $Z^5$ are each independently bromo or fluoro; $Z^4$, when present, is methoxy optionally substituted with 1-3 halo, or deuterated methoxy; and Effector is as defined in any of the embodiments described in the specification.

Other embodiments of the compounds having formulae (I) related to any one or more of the following formulae (Id-i), (Id-ii), (Icd-iii), (Id-iv), (Id-v), (Id-vi), (Id-vii), (Id-viii), (Id-ix), (Id-x), (Id-xi), (Id-xii), (Id-xiii), (Id-xiv), (Id-xv), (Id-xvi), (Id-xvii), (Id-xviii), (Id-xix), or (Id-xx):

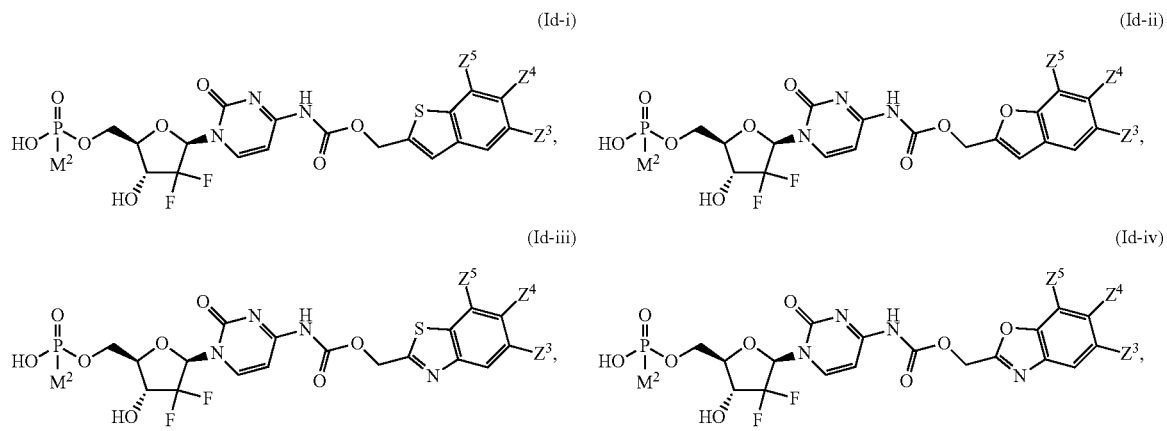

-continued
(Id-v)
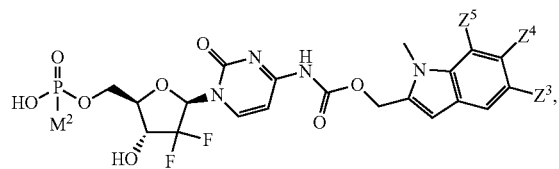
(Id-vi)
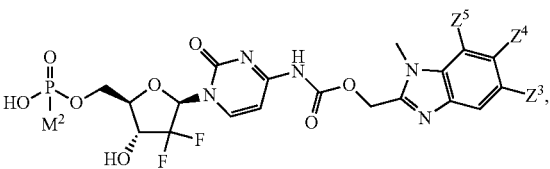
(Id-vii)
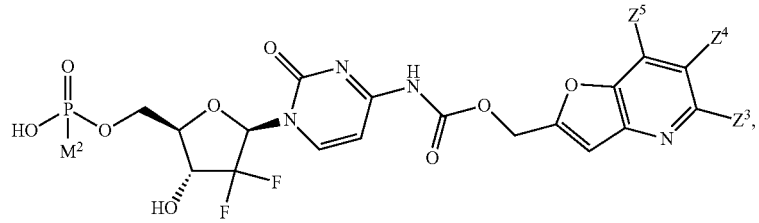
(Id-viii)
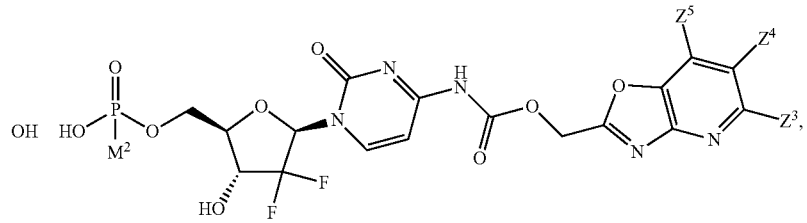
(Id-ix)
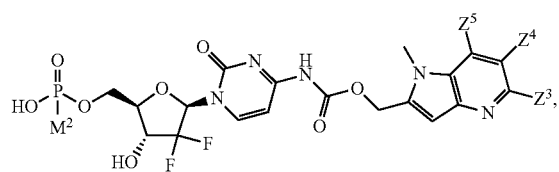
(Id-x)
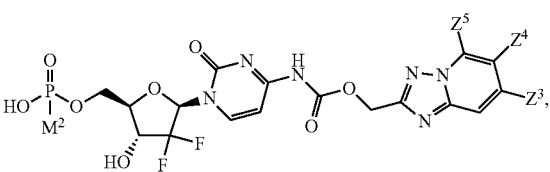
(Id-xi)
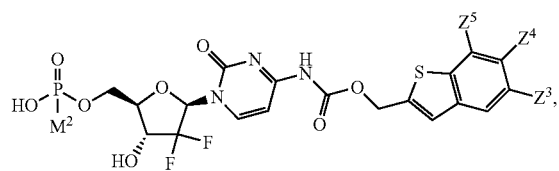
(Id-xii)
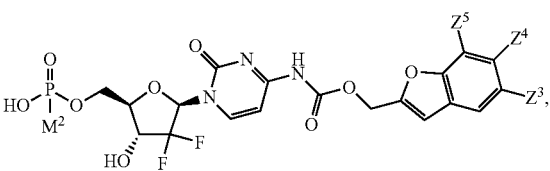
(Id-xiii)
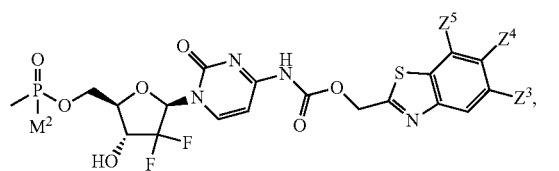
(Id-xiv)
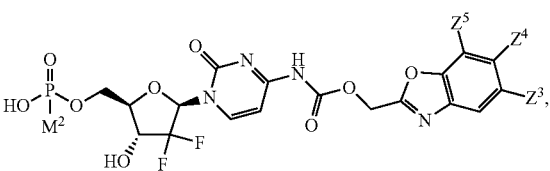
(Id-xv)
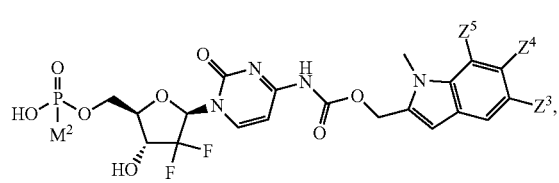
(Id-xvi)
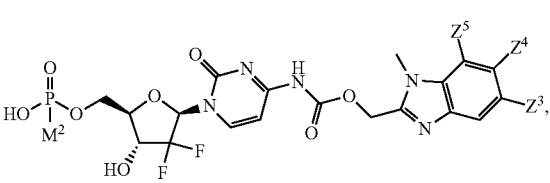

-continued (Id-xvii)

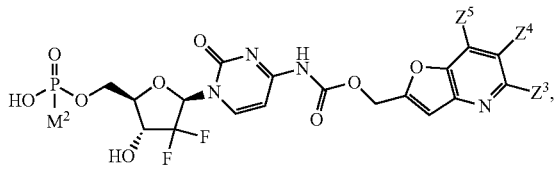

(Id-xviii)

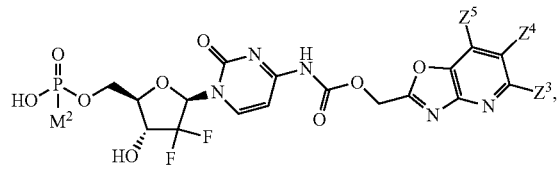

(Id-xix)

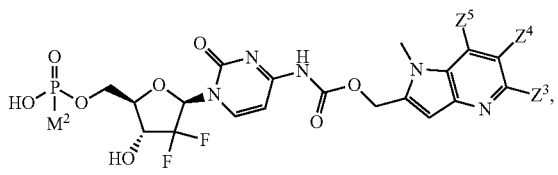

(Id-xx)

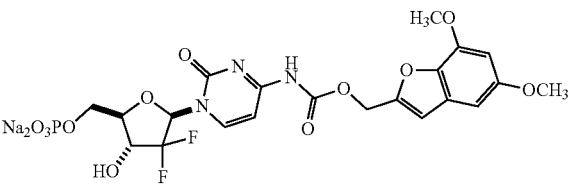

or a pharmaceutically acceptable salt, ester, solvate, or stereoisomer of any of the above formulae, wherein $Z^3$, $Z^4$, and $Z^5$ are each independently methyl optionally substituted with 1-3 halo, halo, methoxy optionally substituted with 1-3 halo or deuterated methoxy; and $M^2$ is —O⁻Na+, —O⁻Et$_3$NH⁺, —O⁻K⁺, —O⁻NH$_4^+$.

In some embodiments, provided herein is a compound having formula (Id-ii-1)

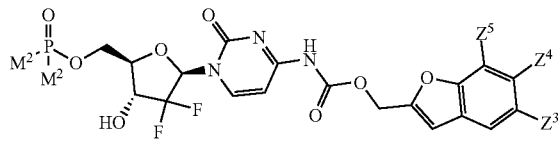

or a pharmaceutically acceptable salt, ester, amide, solvate, or stereoisomer thereof wherein:

$Z^3$, $Z^4$, and $Z^5$ are each independently hydrogen, methyl optionally substituted with 1-3 halo, halo, methoxy optionally substituted with 1-3 halo or deuterated methoxy; and each $M^2$ is independently selected from the group consisting of OH and O⁻ ($M^1$), wherein ($M^1$) in each occurrence is independently a metal cation, ammonium, an alkyl ammonium cation, or an amino acid cation.

In some embodiments of (Id-ii-1), one occurrence of $M^2$ is OH; and the other occurrence of $M^2$ is O⁻ ($M^1$).

In some other embodiments, each occurrence of $M^2$ is an independently selected 0-($M^1$).

In some embodiments of (Id-ii-1), ($M^1$) is selected from the group consisting of Na+, Ca$^{2+}$, K⁺, Mg$^{2+}$, Zn$^{2+}$, NH$^{4+}$, (HNEt3)⁺, meglumine-H⁺, Tromethamine-H⁺, Diethanolamine-H⁺, lysine-H⁺, and arginine-H⁺. In certain embodiments, ($M^1$) is Na⁺.

In some embodiments of (Id-ii-1), each of $Z^5$ and $Z^3$ is independently methoxy.

In some embodiments of (Id-ii-1), $Z^4$ is hydrogen.

In some embodiments of (Id-ii-1), the compound is:

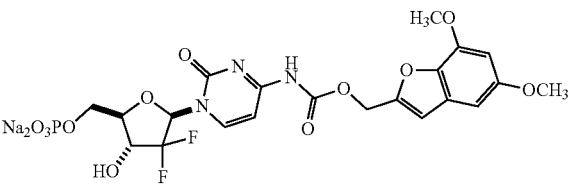

or a pharmaceutically acceptable salt, ester, amide, solvate, or stereoisomer thereof.

Another embodiment of compounds of formula (I) is one or more of compounds described in the Examples herein, or a pharmaceutically acceptable salt, ester, amide, solvate, or stereoisomer of any one or more of compounds 1-5.

The gemcitabine part of the compounds of formula (I) is the moiety which provides the desired targeted effect in cells typically those in which CYP1B1 is expressed. In all embodiments of formula (I), the linker portion of formula (I) is attached directly to the amino bearing base portion of the Effector component of formula (I). When released, the effector molecule has a discernible pharmacological effect on the cells in which it is released.

The Effector molecule has a cytostatic or cytotoxic effect upon the cell that serves to cause its release is expressed (e.g. CYP1B1-expressing cells). As is known, a cytotoxic molecule is a molecule that is toxic to cells whereas a cytostatic agent is one that suppresses the growth and/or replication of cells.

For use according to the present invention, the compounds or a physiologically acceptable salt, solvate, ester or amide thereof described herein may be presented as a pharmaceutical formulation, comprising the compound or physiologically acceptable salt, ester, amide or other physiologically functional derivative thereof, together with one or more pharmaceutically acceptable carriers therefor and optionally other therapeutic and/or prophylactic ingredients. Any carrier(s) are acceptable in the sense of being compatible with the other ingredients of the formulation and not deleterious to the recipient thereof.

Examples of physiologically acceptable salts of the compounds according to the invention include acid addition salts formed with organic carboxylic acids such as acetic, lactic, tartaric, maleic, citric, pyruvic, oxalic, fumaric, oxaloacetic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids.

The determination of physiologically acceptable esters or amides, particularly esters is well within the skills of those skilled in the art.

It may be convenient or desirable to prepare, purify, and/or handle a corresponding solvate of the compounds described herein, which may be used in the any one of the uses/methods described. The term solvate is used herein to refer to a complex of solute, such as a compound or salt of the compound, and a solvent. If the solvent is water, the solvate may be termed a hydrate, for example a monohydrate, di-hydrate, tri-hydrate etc, depending on the number of water molecules present per molecule of substrate.

It will be appreciated that the compounds of the present invention may exist in various stereoisomeric forms and the compounds of the present invention as hereinbefore defined include all stereoisomeric forms and mixtures thereof, including enantiomers and racemic mixtures. The present invention includes within its scope the use of any such stereoisomeric form or mixture of stereoisomers, including the individual enantiomers of the compounds of formula (I) as well as wholly or partially racemic mixtures of such enantiomers.

It will also be understood by those skilled in the art that anticancer SMDCs, such as those described herein, can be targeted towards particular tumors by attachment of a tumor-targeting moiety such as tumor-targeting peptide, for example small peptides identified through the development of phage-displayed peptide libraries. Such peptides or other moieties may assist in the targeting of conjugates that comprise them to a particular cancer, particularly a solid tumor. Accordingly, the provision of such conjugates, i.e. of a compound of the invention conjugated to a tumor-targeting moiety, forms a further aspect of this invention as do compositions, uses and methods described herein that comprise or involve use of such conjugates.

The compounds of the present invention may be prepared using reagents and techniques readily available in the art and/or exemplary methods as described hereinafter. It has been found that compounds of the present invention exhibit cytotoxicity in cells expressing CYP1B1 enzyme, but are substantially non-toxic in normal cells that do not express CYP1B1. Compounds of the invention may also exhibit cytotoxicity in cells expressing CYP1A1 enzyme. In practice, therefore, the compounds of the invention are non-toxic pro-drugs that are converted (typically by CYP1B1) into cytotoxic agents.

Suitably, the compounds of the invention have a cytotoxicity $IC_{50}$ value as defined below or less than 10 μM, advantageously less than 5 μM, for example less than 1.0 μM or 0.5 μM.

In some embodiments, the cytotoxicity of a compound of the invention may be measured by incubating the compound at different serial dilutions with cells engineered to express CYP1B1. Suitably, said cells may be Chinese Hamster Ovary (CHO) cells, which may contain recombinant CYP1B1 and cytochrome P-450 reductase (CPR). High levels of functional enzyme when co-expressed with human P-450 reductase may be achieved using dihydrofolate reductase (DHFR) gene amplification. Typically, the engineered cells may be incubated with the compound and, after a suitable period of time (e.g., 96 hours), further incubated (e.g., for 1.5 hours) with a suitable assay reagent to provide an indication of the number of living cells in culture. A suitable assay reagent is MTS (see below) which is bioreduced by cells into a formazan product that is soluble in tissue culture medium. The absorbance of the formazan product can be directly measured at 510 nm, and the quantitative formazan product as measured by the amount of absorbance at 490 nm or 510 nm is directly proportional to the number of living cells in culture. Detailed methods for determining the $IC_{50}$ value of a compound according to the invention are described in Example 3 below.

By way of comparison, the $IC_{50}$ values of the compounds of the invention may also be measured in cells (e.g., Chinese Hamster Ovary cells) that do not contain CYP1B1, for example wild type CHO cells. The compounds of the invention may suitably have a fold selectivity for CYP1B1 expressing cells of at least 200, where the "fold selectivity" is defined as the quotient of the $IC_{50}$ value of a given compound in non-CYP1 expressing cells and the $IC_{50}$ value of the same compound in CYP1B1 expressing cells.

In some embodiments, the cytotoxicity of a compound of the invention may be also measured by incubating the compound at different serial dilutions with primary head and neck tumor cells derived from patients with head and neck squamous cell carcinoma as described in Example 5.

In some embodiments, the in vivo efficacy of a compound of the invention may be measured by implanting primary head and neck squamous cell carcinoma tumor cells which constitutively express CYP1B1 subcutaneously into the flank of a nude mouse to generate primary human tumor xenograft models and measuring the effect of SMDC treatment on tumor growth.

In some embodiments, the in vivo pharmacokinetic parameters (AUC, concentration, $t_{max}$, $t_{1/2}$) of a compound of this invention may be measured in the plasma and tissues of rodent and non-rodent species including the mouse, rat, dog, and monkey.

As such, the present invention also embraces the use of one or more of the compounds of the invention, including the aforementioned pharmaceutically acceptable esters, amides, salts, solvates and SMDCs, for use in the treatment of the human or animal body by therapy, particularly the treatment or prophylaxis of proliferative conditions such, for example, as proliferative disorders or diseases, in humans and non-human animals, including proliferative conditions which are in certain embodiments of the invention characterized by cells that express CYP1B1. More particularly, the invention comprehends the use of one or more of the compounds of the invention for the treatment of cancers characterized in certain embodiments of the invention by CYP1B1 expression.

By "proliferative condition" herein is meant a disease or disorder that is characterized by an unwanted or uncontrolled cellular proliferation of excessive or abnormal cells which is undesired, such as, neoplastic or hyperplastic growth, whether in vitro or in vivo. Examples of proliferative conditions are pre-malignant and malignant cellular proliferation, including malignant neoplasms and tumors, cancers, leukemias, psoriasis, bone diseases, fibroproliferative disorders (e.g., of connective tissues) and atherosclerosis.

Said proliferative condition may be characterized in certain embodiments of the invention by cells that express CYP1B1.

Said proliferative condition may be selected from bladder, brain, breast, colon, head and neck, kidney, lung, liver, ovarian, prostate and skin cancer. In some embodiments, said proliferative condition may comprise a solid tumor.

Another embodiment relates to a method of treatment or prophylaxis of a proliferative condition, said method comprising administering to a subject a therapeutically or prophylactically useful amount of a compound according to formula (I), including all embodiments of formula (I), or pharmaceutically acceptable salt, ester, amide or solvate thereof, wherein the proliferative condition is bladder, brain, breast, colon, head and neck, kidney, lung, liver, ovarian, prostate and skin cancer.

By "treatment" herein is meant the treatment by therapy, whether of a human or a non-human animal (e.g., in veterinary applications), in which some desired therapeutic effect on the proliferative condition is achieved; for example, the inhibition of the progress of the disorder, including a reduction in the rate of progress, a halt in the rate of progress, amelioration of the disorder or cure of the condition. Treatment as a prophylactic measure is also included. References herein to prevention or prophylaxis herein do not indicate or require complete prevention of a condition; its manifestation may instead be reduced or delayed via prophylaxis or prevention according to the present invention. By a "therapeutically-effective amount" herein is meant an amount of the one or more compounds of the invention or a pharmaceutical formulation comprising such one or more compounds, which is effective for producing such a therapeutic effect, commensurate with a reasonable benefit/risk ratio.

The compounds of the present invention may therefore be used as anticancer agents. By the term "anticancer agent" herein is meant a compound that treats a cancer (i.e., a compound that is useful in the treatment of a cancer). The anti-cancer effect of the compounds of the invention may arise through one or more mechanisms, including the regulation of cell proliferation, the inhibition of angiogenesis, the inhibition of metastasis, the inhibition of invasion or the promotion of apoptosis.

It will be appreciated that appropriate dosages of the compounds of the invention may vary from patient to patient. Determining the optimal dosage will generally involve the balancing of the level of therapeutic benefit against any risk or deleterious side effects of the treatments of the present invention. The selected dosage level will depend on a variety of factors including the activity of the particular compound, the route of administration, the time of administration, the rate of excretion of the compound, the duration of the treatment, other drugs, compounds or materials used in combination and the age, sex, weight, condition, general health and prior medical history of the patient. The amount of compound(s) and route of administration will ultimately be at the discretion of the physician, although generally the dosage will be to achieve local concentrations at the site of action so as to achieve the desired effect.

Administration in vivo can be effected in one dose, continuously or intermittently throughout the course of treatment. Methods of determining the most effective means and dosage of administration are well known to a person skilled in the art and will vary with the formulation used for therapy, the purpose of therapy, the target cell being treated, and the subject being treated. Single or multiple administrations can be carried out with the dose level and pattern being selected by the treating physician.

Pharmaceutical formulations include those suitable for oral, topical (including dermal, buccal and sublingual), rectal or parenteral (including subcutaneous, intradermal, intramuscular and intravenous), nasal and pulmonary administration e.g., by inhalation. The formulation may, where appropriate, be conveniently presented in discrete dosage units and may be prepared by any of the methods well known in the art of pharmacy. Methods typically include the step of bringing into association an active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersible granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active compound is formulated in an appropriate release-controlling matrix, or is coated with a suitable release-controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active compound with the softened or melted carrier(s) followed by chilling and shaping in moulds.

Pharmaceutical formulations suitable for parenteral administration include sterile solutions or suspensions of an active compound in aqueous or oleaeginous vehicles.

Injectable preparations may be adapted for bolus injection or continuous infusion. Such preparations are conveniently presented in unit dose or multi-dose containers, which are sealed after introduction of the formulation until required for use. Alternatively, an active compound may be in powder form that is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient.

As one possibility such formulations are in the form of finely comminuted powders which may conveniently be presented either in a pierceable capsule, suitably of, for example, gelatin, for use in an inhalation device, or alternatively as a self-propelling formulation comprising an active compound, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active compound is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microlitres, upon each operation thereof.

As a further possibility an active compound may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

It should be understood that in addition to the aforementioned carrier ingredients the pharmaceutical formulations described above may include, an appropriate one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

Pharmaceutically acceptable carriers are well known to those skilled in the art and include, but are not limited to, 0.1 M and preferably 0.05 M phosphate buffer or 0.8% saline. Additionally, pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Formulations suitable for topical formulation may be provided for example as gels, creams or ointments.

Liquid or powder formulations may also be provided which can be sprayed or sprinkled directly onto the site to be treated, e.g. a wound or ulcer. Alternatively, a carrier such as a bandage, gauze, mesh or the like can be sprayed or sprinkle with the formulation and then applied to the site to be treated.

Therapeutic formulations for veterinary use may conveniently be in either powder or liquid concentrate form. In accordance with standard veterinary formulation practice, conventional water-soluble excipients, such as lactose or sucrose, may be incorporated in the powders to improve their physical properties. Thus particularly suitable powders of this invention comprise 50 to 100% w/w and preferably 60 to 80% w/w of the active ingredient(s) and 0 to 50% w/w and preferably 20 to 40% w/w of conventional veterinary excipients. These powders may either be added to animal feedstuffs, for example by way of an intermediate premix, or diluted in animal drinking water.

Liquid concentrates of this invention suitably contain the compound or a derivative or salt thereof and may optionally include a veterinarily acceptable water-miscible solvent, for example polyethylene glycol, propylene glycol, glycerol, glycerol formal or such a solvent mixed with up to 30% v/v of ethanol. The liquid concentrates may be administered to the drinking water of animals.

In general, a suitable dose of the one or more compounds of the invention may be in the range of about 1 μg to about 5000 μg/kg body weight of the subject per day, e.g., 1, 5, 10, 25, 50, 100, 250, 1000, 2500 or 5000 μg/kg per day. Where the compound(s) is a salt, solvate, SMDC or the like, the amount administered may be calculated on the basis the parent compound and so the actual weight to be used may be increased proportionately.

In some embodiments, the one or more compounds of the present invention may be used in combination therapies for the treatment of proliferative conditions of the kind described above, i.e., in conjunction with other therapeutic agents. Examples of such other therapeutic agents include but are not limited to topoisomerase inhibitors, alkylating agents, antimetabolites, DNA binders and microtubule inhibitors (tubulin target agents), such as cisplatin, cyclophosphamide, etoposide, irinotecan, fludarabine, 5FU, taxanes or mitomycin C. Other therapeutic agents will be evident to those skilled in the art. For the case of active compounds combined with other therapies the two or more treatments may be given in individually varying dose schedules and via different routes.

The combination of the agents listed above with a compound of the present invention would be at the discretion of the physician who would select dosages using his common general knowledge and dosing regimens known to a skilled practitioner.

Where a compound of the invention is administered in combination therapy with one, two, three, four or more, preferably one or two, preferably one other therapeutic agents, the compounds can be administered simultaneously or sequentially. When administered sequentially they can be administered at closely spaced intervals (for example over a period of 5-10 minutes) or at longer intervals (for example 1, 2, 3, 4 or more hours apart, or even longer period apart where required), the precise dosage regimen being commensurate with the properties of therapeutic agent(s).

The compounds of the invention may also be administered in conjunction with non-chemotherapeutic treatments such as radiotherapy, photodynamic therapy, gene therapy, surgery and controlled diets.

Another aspect of the invention relates to a method of diagnosis of a patient for the presence of tumor cells expressing the CYP1B1 enzyme comprising (a) administering to the patient one or more compounds of the invention;

(b) determining the amount of corresponding hydroxylated metabolite which is subsequently produced; and, (c) correlating the amount with the presence or absence of the tumor cells in the patient.

Another aspect of the invention relates to a method of (1) identifying the presence of a tumor in a patient; and (2) treating the patient, identified as needing the treatment, by administering a therapeutically or prophylactically useful amount of a compound according to any of claims 1-15, or pharmaceutically acceptable salt, ester, amide or solvate thereof. In one embodiment, the tumor can be identified by employing a tumor biomarker. Tumor biomarkers can also be useful in establishing a specific diagnosis, such as determining whether tumors are of primary or metastatic origin. To make this distinction, chromosomal alterations found on cells located in the primary tumor site can be screened against those found in the secondary site. If the alterations match, the secondary tumor can be identified as metastatic; whereas if the alterations differ, the secondary tumor can be identified as a distinct primary tumor.

In another embodiment, the tumor can be identified by a biopsy. Non-limiting examples of biopsies that can be employed include fine needle aspiration biopsy, a core needle biopsy, a vacuum-assisted biopsy, an image-guided biopsy, a surgical biopsy, An incisional biopsy, an endoscopic biopsy, a bone marrow biopsy.

In another embodiment, the identification of tumor can be by magnetic resonance imaging (MRI) is a test that uses magnetic fields to produce detailed images of the body.

In another embodiment, the identification of tumor can be by a bone scan. In another embodiment, the identification of tumor can be a computed tomography (CT) scan, also called a CAT scan.

In another embodiment, the identification of tumor can be by an integrated PET-CT scan combines images from a positron emission tomography (PET) scan and a computed tomography (CT) scan that have been performed at the same time using the same machine.

In another embodiment, the identification of tumor can be by an ultrasound, which is an imaging test that uses high-frequency sound waves to locate a tumor inside the body.

In more specific embodiments, companion diagnostics that can be used to help treat patients, as a form of personalized medicine can be obtained from Ventana Medical Systems, Inc., a member of the Roche Group, located at 1910 Innovation Park Drive, Tucson, AZ 85755.

The examples and scheme below depict the general synthetic procedure for the compounds disclosed herein. Synthesis of the compounds disclosed herein is not limited by these examples and schemes. One skilled in the art will know that other procedures can be used to synthesize the compounds disclosed herein, and that the procedures described in the examples and schemes is only one such procedure. In the descriptions below, one of ordinary skill in the art would recognize that specific reaction conditions, added reagents, solvents, and reaction temperatures can be modified for the synthesis of specific compounds that fall within the scope of this disclosure.

Preparation of Compounds

General $^1$H, $^{13}$C and $^{31}$P nuclear magnetic resonance (NMR) spectra were recorded in the indicated solvent on either a Bruker Avance DPX 400 MHz spectrometer. Chemical shifts are expressed in ppm. Signal splitting patterns are described as singlet (s), broad singlet (bs), doublet (d), triplet (t), quartet (q), multiplet (m) or combination thereof. Low resolution electrospray (ES) mass spectra were recorded on a Bruker MicroTof mass spectrometer, run in a positive ion mode, using either methanol/water (95:5) or water acetonitrile (1:1)+0.1% formic acid as a mobile phase. High resolution electrospray measurements were performed on a Bruker Microtof mass spectrometer. LC-MS analysis were performed with an Agilent HPLC 1100 (Phenomenex Gemini Column 5µ C18 110 Å 50×3.0 mm, eluted with (0 to 20% MeOH/H$_2$O) and a diode array detector in series with a Bruker Microtof mass spectrometer. Column chromatography was performed with silica gel (230-400 mesh) or RediSep®0.4, 12, 40 or 80 g silica prepacked columns. All the starting materials are commercially available and were used without further purification. All reactions were carried out under dry and inert conditions unless otherwise stated.

Methods for the preparation and/or separation and isolation of single stereoisomers from racemic mixtures or non-racemic mixtures of stereoisomers are well known in the art. For example, optically active (R)- and (S)-isomers can be prepared using chiral synthons or chiral reagents, or resolved using conventional techniques. Enantiomers (R- and S-isomers) can be resolved by methods known to one of ordinary skill in the art, for example by: formation of diastereoisomeric salts or complexes which can be separated, for example, by crystallization; via formation of diastereoisomeric derivatives which can be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step can be required to liberate the desired enantiomeric form. Alternatively, specific enantiomer can be synthesized by asymmetric synthesis using optically active reagents, substrates, catalysts or solvents or by converting on enantiomer to the other by asymmetric transformation. For a mixture of enantiomers, enriched in a particular enantiomer, the major component enantiomer can be further enriched (with concomitant loss in yield) by recrystallization.

The examples below depict the general synthetic procedure for the compounds disclosed herein. Synthesis of the compounds disclosed herein is not limited by these examples and schemes. One skilled in the art will know that other procedures can be used to synthesize the compounds disclosed herein, and that the procedures described in the examples and schemes is only one such procedure. In the descriptions below, one of ordinary skill in the art would recognize that specific reaction conditions, added reagents, solvents, and reaction temperatures can be modified for the synthesis of specific compounds that fall within the scope of this disclosure. Unless otherwise specified, intermediate compounds in the examples below, that do not contain a description of how they are made, are either commercially available to one skilled in the art, or can otherwise be synthesized by the skilled artisan using commercially available precursor molecules and synthetic methods known in the art.

Unless otherwise specified, intermediate compounds in the examples below, that do not contain a description of how they are made, are either commercially available to one skilled in the art, or can otherwise be synthesized by the skilled artisan using

GENERAL PREPARATORY EXAMPLES FOR TRIGGER PRECURSORS

Trigger precursor molecules for compounds of the invention can be made by the following synthetic schemes and by making any necessary modifications to the starting materials, reagents and/or reaction conditions known to skilled medicinal chemistry to arrive at the compounds of the invention. Synthetic precursor molecules to these schemes are either commercially available or their preparation is known in the art.

Preparatory Example 1

Benzofuran Trigger Precursors

Benzofuran trigger precursors (i), wherein $Z^3$, $Z^4$ and $Z^5$ are as defined in the specification, can be made using the following scheme:

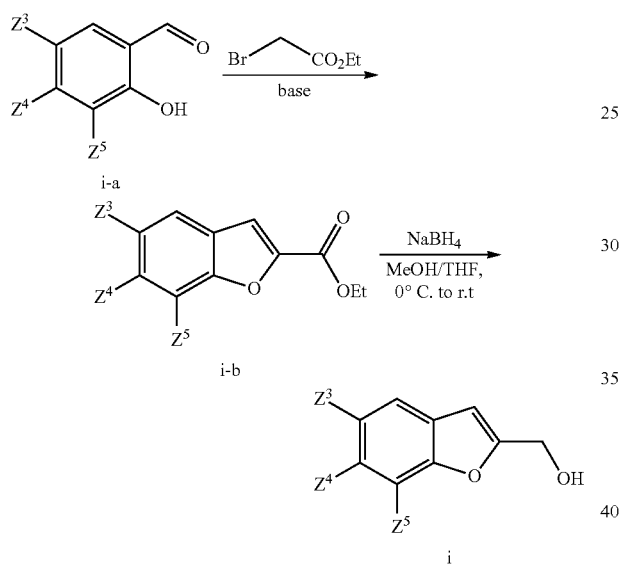

The synthesis of benzofuran-2-carboxylates is widely known and many methods exist for the synthesis of intermediates such as (i-b). As such, appropriately substituted salicylaldehyde starting materials (i-a) can be reacted with a haloacetate such as ethyl-2-bromoacetate followed by cyclization of the formylphenoxyacetic acid derivatives intermediates [see: H. Dumont and S. Kostanecki, "Zur kenntnis der cumaron-gruppe," Chemische Berichte, vol. 42, no. 1, pp. 911-915, 1909]. The cyclizations can be carried out in an alcoholic solution in the presence of a basic catalyst such as sodium ethanolate, 1,8-diazobicyclo-[5.4.0]-7-undecane, or potassium carbonate. The resulting esters can then be further functionalized or converted to the desired trigger precursor using a known method for the reduction of a carboxylate ester to a primary alcohol such as a metal hydride reducing agent ($LiAlH_4$, $LiBEt_3H$ or $NaBH_4$).

Preparatory Example 2

Benzo[b]thiophene Trigger Precursors

Benzo[b]thiophene trigger precursors (iii) wherein $Z^3$, $Z^4$ and $Z^5$ are as defined in the specification, can be made using one of the following schemes.

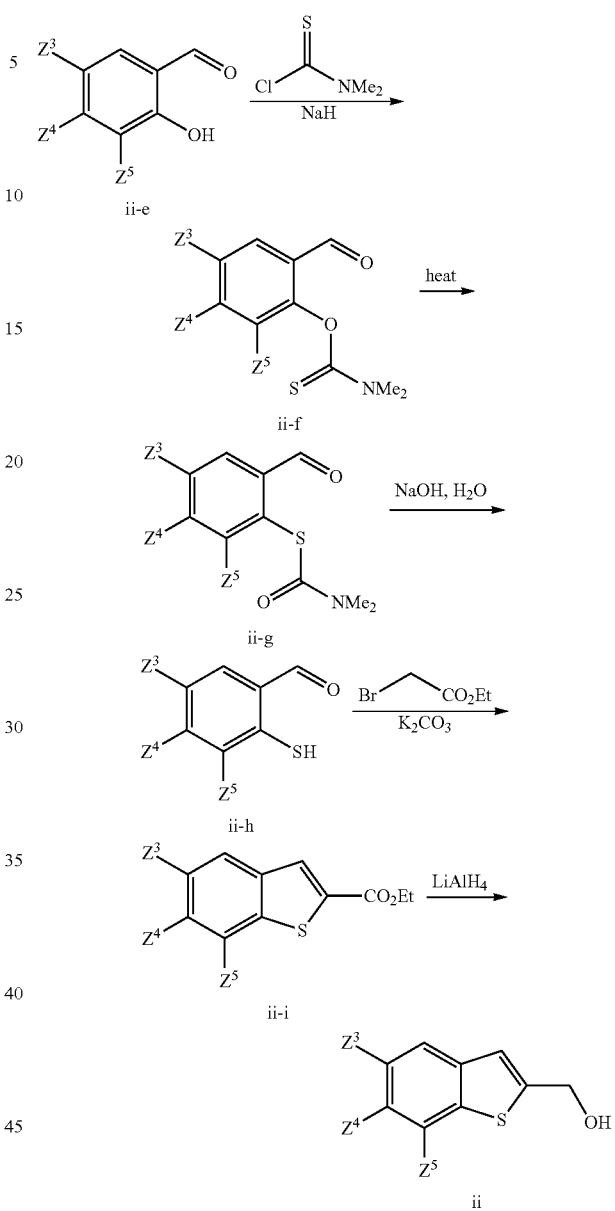

Alternatively, the benzothiophen-2-yl alcohols of formula (ii) can conveniently be prepared from the substituted salicylaldehyde derivatives of formula (ii-e) (see scheme above). Alkylation with dimethylthiocarbamyl chloride and subsequent Newman-Kwart rearrangement provides the intermediates of formula (ii-g). Alkaline work-up can afford the free thiophenol of formula (ii-h) which can undergo an alkylation/cyclization reaction using standard procedures. Ester intermediate (ii-i) can then be reduced to alcohols (ii) using methods commonly employed for the reduction of carboxylate esters to primary alcohols such as LAH in tetrahydrofuran.

Preparatory Example 3

1H-benzo[d]imidazole Trigger Precursors 1H-benzo[d]imidazole trigger precursors, wherein $Z^3$, $Z^4$ and $Z^5$ are as defined in the specification, can be made using the following scheme similar to that described by Borchardt et. al. "Preparation of tetrahydropyranones as hepatitis C virus RNA-dependent RNA polymerase inhibitors", WO 2004/074270.

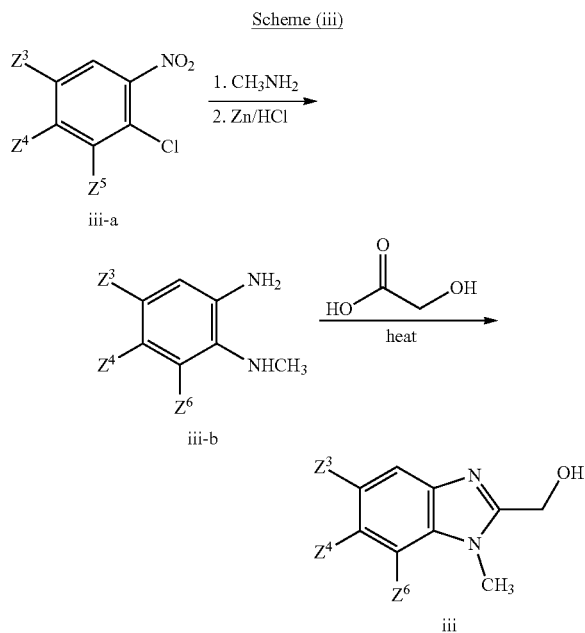

A suitably substituted 2-halo-nitrobenzene (iii) can be reacted with methylamine to form an amino nitro intermediate which can then be reduced using known methods for the conversion of nitro arenes to anilines such as zinc and an acid source such as HCl to give compound (iii-b). Compound (iii-b) can then converted to target alcohol (vi) by heating with a reagent such as hydroxy acetic acid.

Preparatory Example 4

1H-indole Trigger Precursors 1H-indole trigger precursors, wherein $Z^3$, $Z^4$ and $Z^5$ are as defined in the specification, can be made using the following scheme similar to that described by Condie et. al. in *Tetrahedron*, (2005), 61(21), 4989-5004.

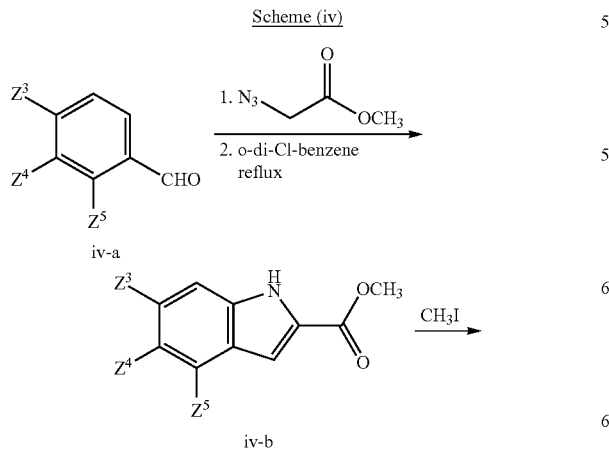

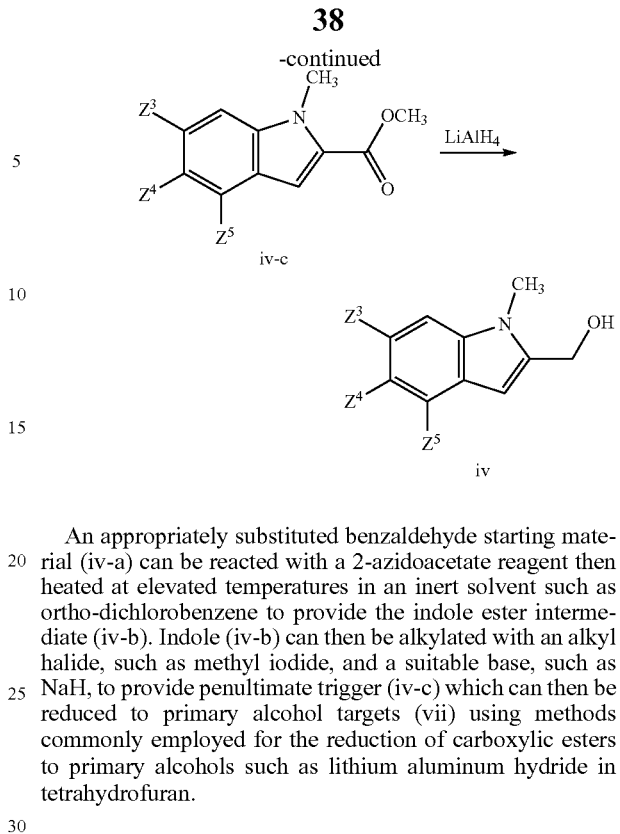

An appropriately substituted benzaldehyde starting material (iv-a) can be reacted with a 2-azidoacetate reagent then heated at elevated temperatures in an inert solvent such as ortho-dichlorobenzene to provide the indole ester intermediate (iv-b). Indole (iv-b) can then be alkylated with an alkyl halide, such as methyl iodide, and a suitable base, such as NaH, to provide penultimate trigger (iv-c) which can then be reduced to primary alcohol targets (vii) using methods commonly employed for the reduction of carboxylic esters to primary alcohols such as lithium aluminum hydride in tetrahydrofuran.

Preparatory Example 5

Benzothiazole Trigger Precursors

Benzothiazole trigger precursors, wherein $Z^3$, $Z^4$ and $Z^5$ are as defined in the specification, can be made using either of the following schemes.

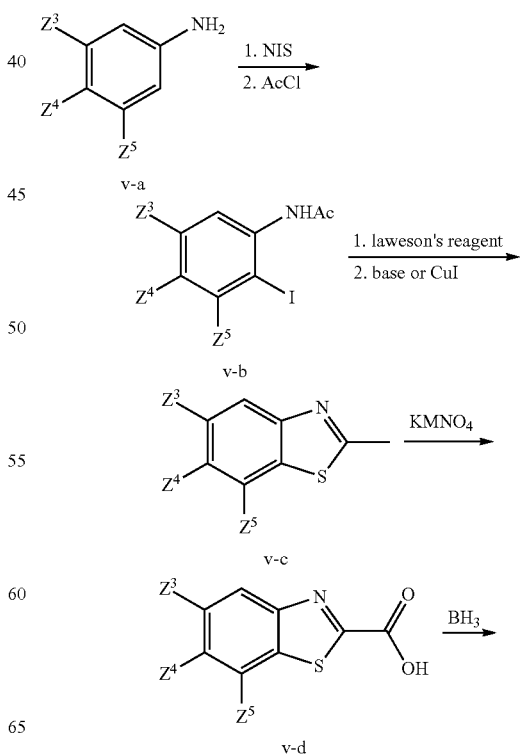

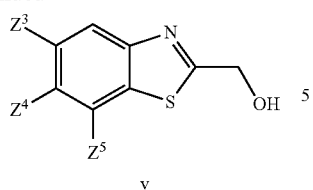

v

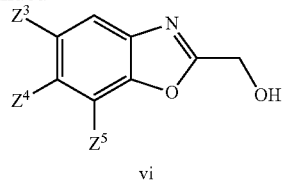

vi

Appropriately substituted anilines can be iodinated then acylated to intermediates (v-b) using standard methods known to effect such transformations such as N-iodosuccinimide followed by reaction with acetyl chloride. Acetamides (v-b) can be converted to the corresponding thioacetamides using a reagent such as Laweson's reagent then cyclized using either a base or copper(I)iodide to provide thiazoles (v-c).

The 2-methyl group can then be oxidized to the corresponding carboxylic acid (v-d) using an oxidant such as potassium permanganate. Subsequent conversion to the primary alcohols (ix) can be effected using conditions described above.

Preparatory Example 6

Benzoxazole Trigger Precursors

Benzoxazole trigger precursors, wherein $Z^3$, $Z^4$ and $Z^5$ are as defined in the specification, can be made using either of the following schemes.

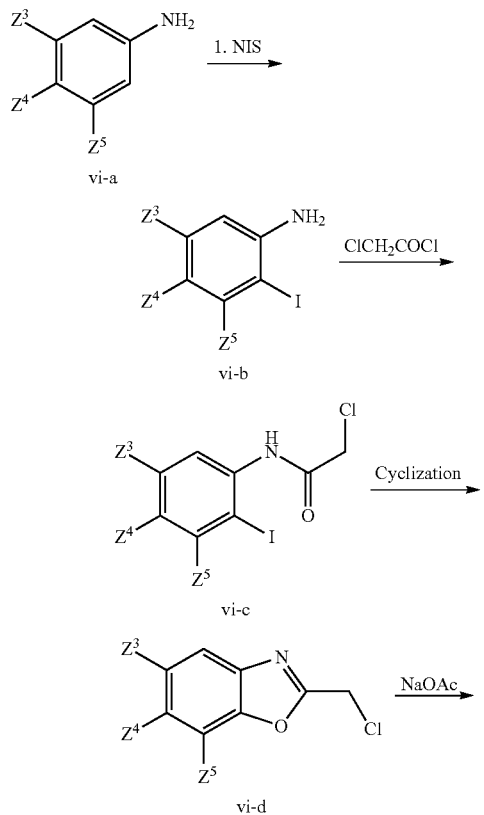

Appropriately substituted anilines can be iodinated then acylated to intermediates (vl-b) using standard methods known to effect such transformations such as N-iodosuccinimide followed by reaction with acetyl chloride. Acetamides (vl-c) can be cyclized to provide oxazoles (vl-d). Subsequent conversion to the primary alcohols (vi) can be effected using conditions described above.

Synthetic Examples for Compounds of the Invention

Compounds of the invention can be made according to the Synthetic Schemes I and II below, and by making any necessary modifications to the starting materials, reagents and/or reaction conditions known to skilled medicinal chemist to arrive at the compounds of the invention. Synthetic precursor molecules to these schemes are either commercially available or their preparation is known in the art.

Synthetic Scheme I

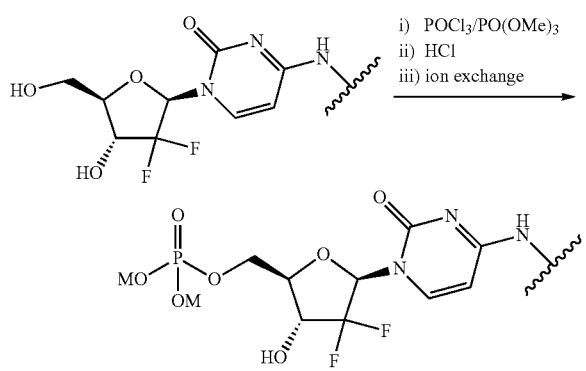

Phosphate analogs of the SMDCs can be prepared starting from advanced intermediates described herein using well known and established literature methods for the synthesis of phosphate and phosphonate analogs of nucleosides (see: Pradere et. al. Chem. Rev. 2014, 114, 9154-9218).

Synthesis of Intermediate Compounds

Compound A:
(5,7-dibromobenzofuran-2-yl)methanol

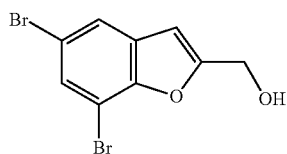 [SMILES: OCc1cc2cc(Br)cc(Br)c2o1]

Step A: Synthesis of Int A-1

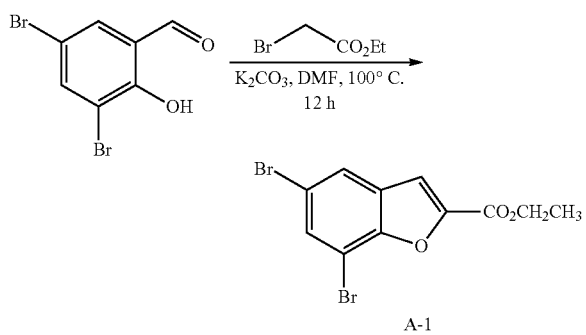

To a solution of 3,5-dibromo-2-hydroxybenzaldehyde (400 g, 1.44 mol) and ethyl 2-bromoacetate (360 g, 2.16 mol) in DMF (1800 mL) was added anhydrous potassium carbonate (590 g, 4.29 mol) in one portion at room temperature. The mixture was heated at 100° C. and magnetically stirred at this temperature overnight. The mixture was cooled to room temperature and the solids were removed by filtration. The filter cake was washed with EtOAc (500 mL×3) and the filtrate was concentrated under reduce pressure with rotary-evaporator to remove EtOAc. The residue was poured into ice water (w/w=1/1, 4 L) whereby a yellow solid formed. The solid was collected by filtration and washed with MeOH (200 mL) three times. The solid was dried under reduced pressure to give 240 g of compound Int A-1 which was used directly in the next step. $R_f$=0.5 (Petroleum Ether:EtOAc=20:1)

Step B: Synthesis of Compound A

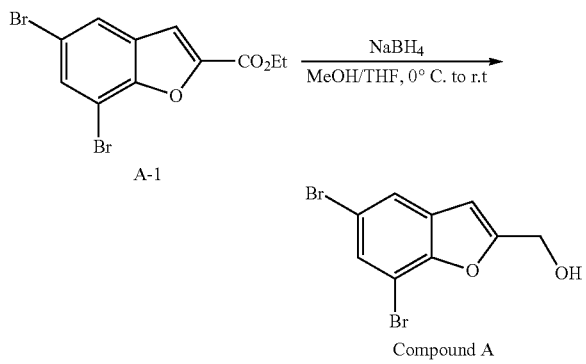

To a cooled solution of Int A-1 (120 g, 0.35 mol) in MeOH (1000 mL) and THF (1000 mL) was added NaBH$_4$ (52.8 g, 1.39 mol), portion-wise (5 g each) in order to keep the reaction temperature between 5-10° C. The resulting mixture was stirred for 3 hours before removing the ice bath and allowing the reaction to come to room temperature over a period of 16 h. The mixture was poured into ice/water (w/w=1/1, 3 L) and concentrated to remove most of the organic solvents. The mixture was extracted with EtOAc (800 mL×3) and the combined organic washings were extracted with saturated brine (400 mL) three times. The organic phase was separated and dried over anhydrous sodium sulfate. This process was repeated and the two reaction products were combined and concentrated to afford 120 g of crude compound A which was used directly to the next step. $R_f$=0.4 (Petroleum Ether:EtOAc=5:1) $^1$H NMR: 400 MHz CDCl$_3$ δ 7.62 (d, J=1.8 Hz, 1H), 7.58 (d, J=1.5 Hz, 1H), 6.69 (s, 1H), 4.81 (d, J=3.3 Hz, 2H), 2.12 (br.s, 1H).

Compound B: (5,7-dimethoxybenzofuran-2-yl)methanol

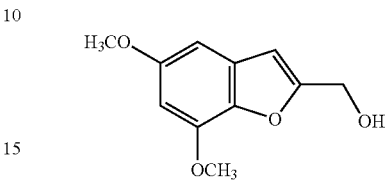

Synthesis of Compound B

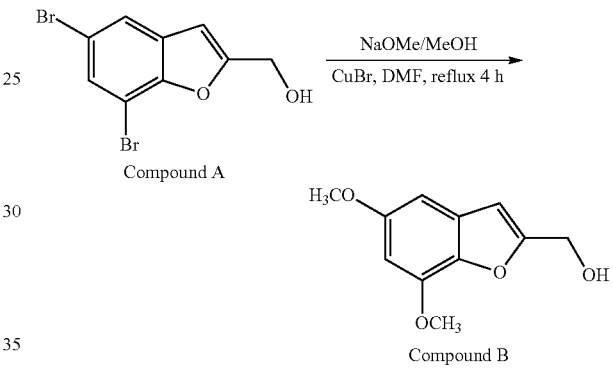

To a mixture of compound A (60 g, 0.20 mol), NaOMe (600 mL, 30% w/w, purchased from Alfa) and DMF (6 g, 0.08 mol) was added CuBr (8 g, 0.056 mol) at room temperature under nitrogen. Then the mixture was stirred at 80° C. for 4 h. The reaction mixture was cooled to 0° C. and then H$_2$O (500 mL) was added to the mixture at 0° C. The mixture was filtered through a pad of Celite and the filtrate was extracted with DCM (500 mL) three times. The combined DCM extracts were dried over anhydrous sodium sulfate and filtered. The filtrate was concentrated to give a brown solid. This process was repeated and the two reaction products were combined and concentrated to afford an oil which was purified by column chromatography (Pet Ether:EtOAc=5:1 to 0:1) to give 60 g of compound B as a yellow solid. $R_f$ (Pet Ether:EtOAc=5:1)=0.4 $^1$H NMR (400 MHz) CDCl$_3$ δ 6.62 (d, J=6.3 Hz, 1H), 6.46 (s, 1H), 4.77 (d, J=6.0 Hz, 2H), 3.99 (s, 3H), 3.86 (s, 3H).

Compound C: (5,7-bis(methoxy-d$_3$)benzofuran-2-yl)methanol

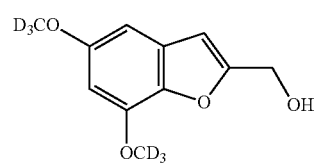

Step A: Synthesis of Int C-1

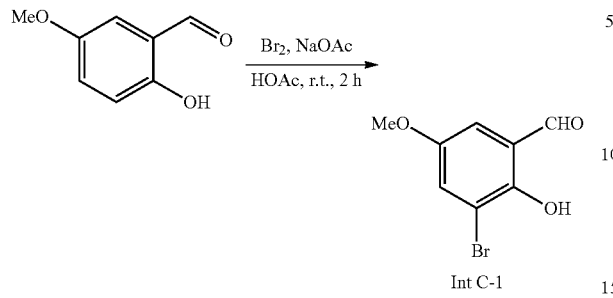

To a mixture of 5-methoxysalicylaldehyde (200 g, 1.31 mol) and anhydrous NaOAc (172 g, 2.10 mol) in AcOH (1.5 L) was added Br$_2$ (270 g, 1.71 mol) dropwise with dropping funnel over 1 hour between 0-5° C. (ice-water bath) under nitrogen. The mixture was warmed to room temperature and stirred for 2 hours. The mixture was poured into ice-water (w/w=1/1, 2 L) and stirred for 15 min. Then the mixture was filtered. The filtrate was washed with water (400 mL×3) and then dried by vacuum (oil pump) at 45° C. for 2 days to afford Int C-1 (200 g) as yellow solid. LCMS: 230.9 [M+H]$^+$. $^1$H NMR: (DMSO-d$^6$, 400 MHz): δ 10.09 (s, 1H), 7.54 (d, J=2.8 Hz, 1H), 7.32 (d, J=2.8 Hz, 1H), 3.78 (s, 3H).

Step B: Synthesis of Int C-2

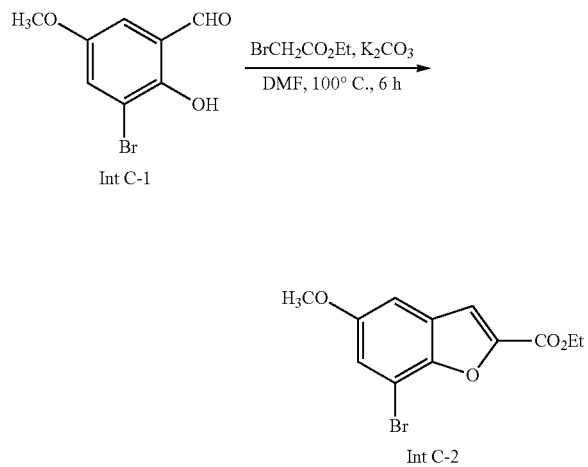

To a mixture of Int C-1 (200 g, 0.87 mol) and anhydrous K$_2$CO$_3$ (360 g, 2.61 mol) in 1000 mL of dry DMF was added 217 g (1.30 mol) of ethyl 2-bromoacetate in one portion at room temperature under nitrogen and stirred at room temperature for 10 min before being heated to 100° C. and stirred for 6 hours. The mixture was cooled to room temperature and concentrated. The residue was poured into water (1 L) and stirred for 20 min. The mixture was filtered and the filtrate was washed with water (500 mL×3) and dried by vacuum (oil pump) to afford Int C-2 (105.4 g) as brown solid. LCMS: 299.0 [M+H]$^+$. $^1$H NMR (DMSO-d$^6$, 400 MHz): δ 7.76 (s, 1H), 7.40 (s, 1H), 7.30 (s, 1H), 4.38 (q, J=7 Hz, 2H), 3.82 (s, 3H), 2.09 (s, 1H), 1.35 (t, J=7 Hz, 3H).

Step C: Synthesis of Int C-3

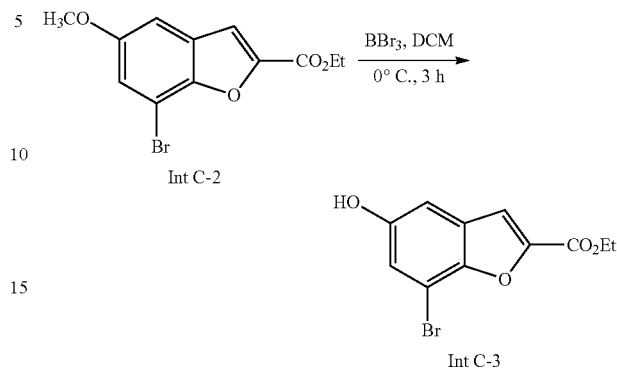

To a solution of Int C-2 (120 g, 0.40 mol) in DCM (700 mL) was added a solution of BBr$_3$ (350 g, 1.4 mol) in DCM (500 mL) drop wise at −70° C. over a period of 30 min under nitrogen during which the temperature was maintained below −60° C. The reaction mixture was warmed to 0° C. and stirred at 0° C. for 3 h. The reaction was poured into iced water (w/w=1/1, 1 L) slowly and then extracted with DCM (800 mL×2). The combined organic phase was washed with saturated brine (800 mL×2), dried over anhydrous Na$_2$SO$_4$, filtered and concentrated by vacuum. The residue was purified by silica gel chromatography (column height: 150 mm, diameter: 50 mm, 100-200 mesh silica gel, petroleum ether/EtOAc=20/1, 10/1, 5/1) to afford Int C-3 (42 g) as white solid. LCMS: 283.0 [M−H]+. $^1$H NMR (DMSO-d$^6$, 400 MHz): δ 9.86 (s, 1H), 7.72 (s, 1H), 7.20 (s, 1H), 7.09 (s, 1H), 4.38 (q, J=7 Hz, 2H), 1.34 (t, J=7 Hz, 3H).

Step D: Synthesis of Int C-4

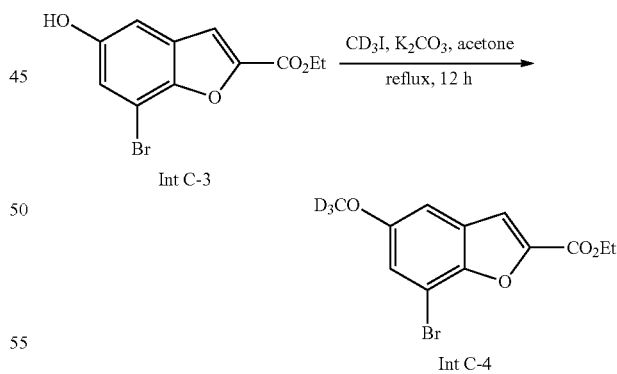

To a solution of Int C-3 (95 g, 0.33 mol) in dry acetone (2 L) was added K$_2$CO$_3$ (115 g, 0.83 mol) and CD$_3$I (97 g, 0.67 mol) in one portion and heated to reflux for 12 hours. The mixture was cooled and filtered and the solid was washed with acetone (300 mL×3). The combined organic layers were evaporated to afford Int C-4 (81 g) as yellow solid. LCMS: 302.0 [M+H]$^+$. $^1$H NMR (DMSO-d$^6$, 400 MHz): δ 7.77 (s, 1H), 7.41 (s, 1H), 7.31 (s, 1H), 4.38 (q, J=7.2 Hz, 2H), 1.35 (t, J=7.2 Hz, 3H).

Step E: Synthesis of Int C-5

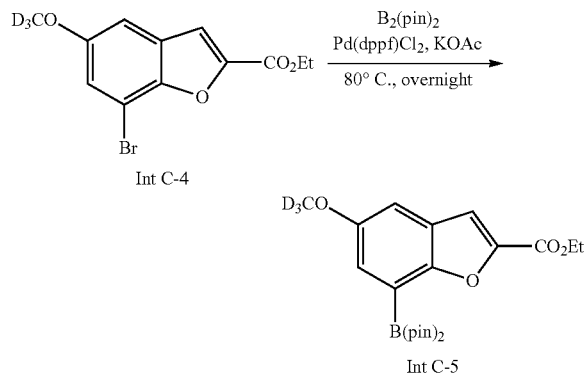

A mixture of Int C-4 (70 g, 0.071 mol), bis(pinacolato) diboron (89 g, 0.35 mol), KOAc (68.6 g, 0.70 mol) and Pd(dppf)Cl$_2$ (16.8 g, 0.023 mol) in DMSO (800 mL) was de-gassed for 15 min with nitrogen and then heated to 80° C. overnight under nitrogen. The reaction mixture was poured into water (1.5 L) and extracted with EtOAc (600 mL×3). The organic extracts were washed with saturated brine (800 mL×2), dried over anhydrous MgSO$_4$ and filtered. The filtrate was concentrated to give a residue which was purified by silica gel column chromatography (column height: 80 mm, diameter: 28 mm, 100-200 mesh silica gel, petroleum ether/EtOAc=20/1, 10/1, 5/1) to afford Int C-5 (53 g) as pale solid. $^1$H NMR (DMSO-d$^6$, 400 MHz): δ 7.62 (s, 1H), 7.38 (d, J=2.4 Hz, 1H), 7.26 (d, J=2.4 Hz, 1H), 4.31 (q, J=7.2 Hz, 2H), 1.28-1.32 (m, 15H).

Step F: Synthesis of Int C-6

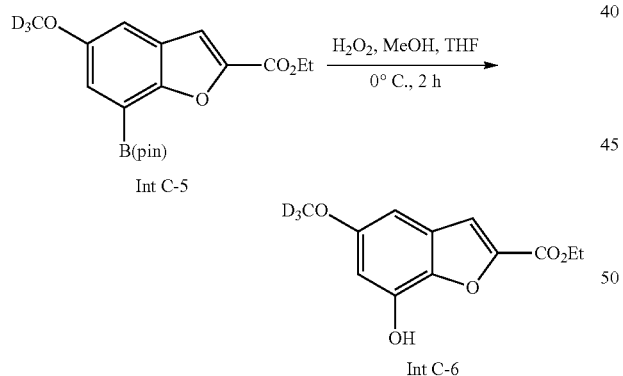

To a solution of Int C-5 (58 g, 0.17 mol) in 600 mL of THF/MeOH (v/v=1/2) was added 30% H$_2$O$_2$ (200 mL) at 0° C. in one portion. The mixture was stirred at same temperature for 2 hours. Saturated aqueous Na$_2$S$_2$O$_3$ (500 mL) was added and the mixture was stirred for another 1 hour. The reaction was checked by potassium iodide-starch test paper to see if H$_2$O$_2$ was destroyed. The mixture was extracted with EtOAc (500 mL×3) and the combined extracts were washed with brine (500 mL), dried over anhydrous MgSO$_4$ and then filtered. The filtration was concentrated to afford Int C-6 (25.4 g) as white solid. LCMS: 240.1 [M+H]$^+$. $^1$H NMR: (DMSO, 400 MHz): δ 10.40 (s, 1H), 7.57 (s, 1H), 6.64 (d, J=2.4 Hz, 1H), 6.48 (d, J=2.4 Hz, 1H), 4.31 (q, J=7.2 Hz, 2H), 1.30 (t, J=7.2 Hz, 3H).

Step G: Synthesis of Int C-7

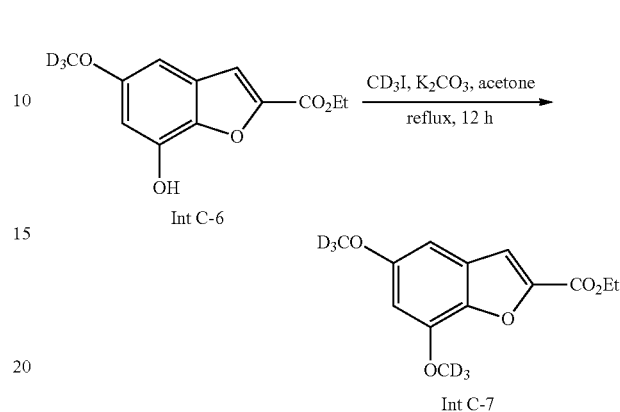

To a solution of Compound Int C-6 (27 g, 0.113 mol) in acetone (800 mL) was added anhydrous K$_2$CO$_3$ (38.8 g, 0.282 mol) and CD$_3$I (32.8 g, 0.226 mol). The reaction mixture was heated to reflux for 12 h then cooled and filtered. The solid was washed with acetone (400 mL×3) and the combined organic extracts were evaporated by vacuum to afford 22 g of Compound Int C-7 as white solid. LCMS: 257.1 [M+H]$^+$. $^1$H NMR: (DMSO-d$^6$, 400 MHz): δ 7.60 (s, 1H), 6.76 (d, J=2.4 Hz, 1H), 6.67 (d, J=2.4 Hz, 1H), 4.31 (q, J=7.2 Hz, 2H), 1.30 (t, J=7.2 Hz, 3H).

Step H: Synthesis of Compound C

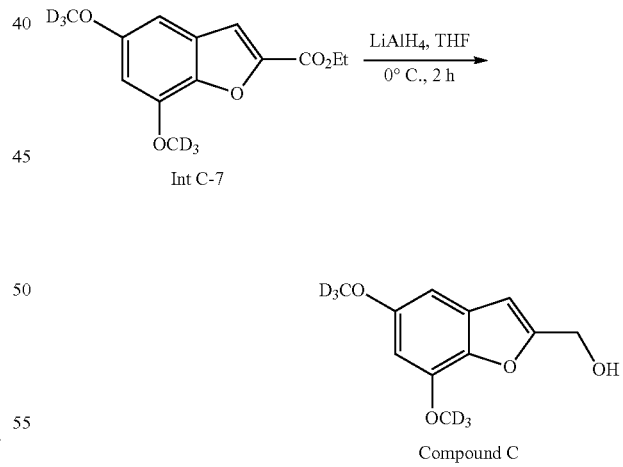

To a solution of Int C-7 (16 g, 0.062 mol) in anhydrous THF (400 mL) was added LiAlH$_4$ (4.8 g, 0.125 mol) at 0° C. over 10 min under nitrogen. The reaction mixture was stirred at 0° C. for 2 hours. The reaction was quenched with water (100 ml) and the resulting suspension was filtered. The filtrate was concentrated to give Compound C (8.5 g) as white solid. LCMS: 197.2 [M–OH]$^+$, 215.2 [M+H]+, 237.1 [M+23]+. $^1$H NMR: (DMSO, 400 MHz): δ 6.65 (s, 2H), 6.49 (s, 1H), 5.46 (t, J=6 Hz, 1H), 4.51 (d, J=6 Hz, 2H).

Compound D:
5-methoxy-7-methylbenzofuran-2-yl)methanol

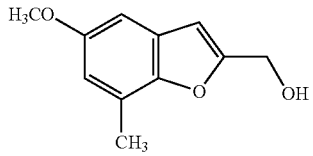

Step A: Synthesis of Int D-1

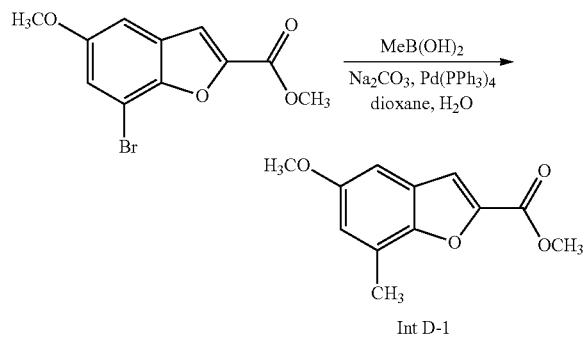

To a solution of 2.0 g (7.0 mmol) of methyl 7-bromo-5-methoxybenzofuran-2-carboxylate (prepared in a manner similar to that described for the ethyl ester Int C-2), CH$_3$B(OH)$_2$ (0.42 g, 7.0 mmol) and Na$_2$CO$_3$ (2.2 g, 20.7 mmol) in dioxane (80 mL)/H$_2$O (10 mL) was added Pd(PPh$_3$)$_4$ (0.8 g, 0.7 mmol). The mixture was refluxed overnight then cooled to room temperature. The reaction mixture was poured into H$_2$O, extracted with EtOAc and the organic extracts were washed with brine and dried over MgSO$_4$. The solution was concentrated to give a residue which was purified by silica gel column to give compound 320 mg of Int D-1.

Step B: Synthesis of Compound D

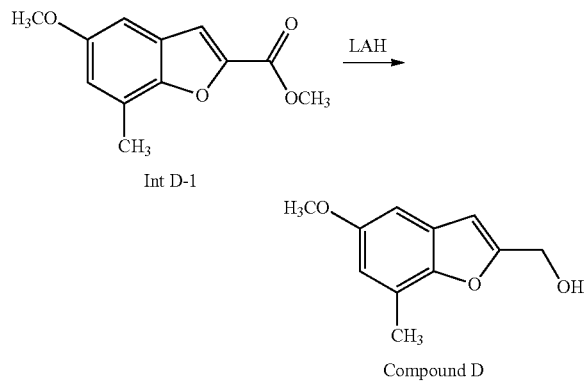

To a suspension of LiAlH$_4$ (0.22 g, 5.79 mmol) in THF (15 mL) was added dropwise a solution of Int D-1 (0.32 g, 1.45 mmol) in THF (15 mL) at 0° C. The mixture was stirred for 30 min at 0° C. then poured into H$_2$O, extracted with EtOAc, the organic phase was washed with brine, dried over MgSO$_4$, concentrated to give a residue, which was purified by silica gel column to give 260 mg of compound D. LCMS: (EI): 175.1 [M−OH]$^+$, 193.1[MH]+. $^1$H NMR (400 MHz, DMSO-d$^6$): δ 6.92 (1H, s), 6.70 (1H, s), 6.69 (1H, s), 5.45 (1H, t, J=11.6 Hz), 5.54 (2H, dd, J=0.8 Hz, 6 Hz), 3.76 (3H, s), 2.41 (3H, s).

Compound E:
(7-cyclopropyl-5-methoxybenzofuran-2-yl)methanol

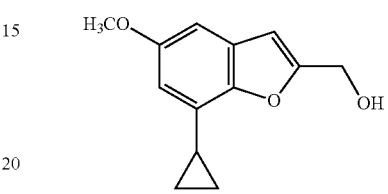

Step A: Synthesis of Compound E

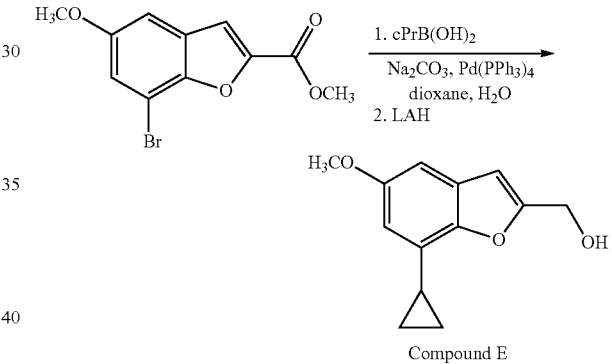

To a solution of 2.0 g (7.0 mmol) of methyl 7-bromo-5-methoxybenzofuran-2-carboxylate (prepared in a manner similar to that described for the ethyl ester Int C-2), cyclopropylboronic acid (0.6 g, 8.0 mmol) and Na$_2$CO$_3$ (2.2 g, 20.7 mmol) in dioxane (80 mL)/H$_2$O (10 mL) was added Pd(PPh$_3$)$_4$ (0.8 g, 0.7 mmol). The mixture was refluxed overnight then cooled. The reaction mixture was poured into H$_2$O and extracted with EtOAc (3×20 mL). The combined organic extracts were washed with brine, dried over MgSO$_4$ and concentrated to give a residue which was purified by silica gel column to give 200 mg of the desired ester. To a suspension of LiAlH$_4$ (0.12 g, 3.25 mmol) in THF (5 mL) was added dropwise a solution of the ester (0.20 g, 0.813 mmol) in THF (5 mL) at 0° C. and stirred for 30 min at 0° C. The reaction mixture was poured into H$_2$O, extracted with EtOAc and the organic extracts were washed with brine, dried over MgSO$_4$, concentrated to give a residue which was purified by silica gel column to give compound E (0.15 g). LCMS: MS (EI) for C$_{13}$H$_{14}$O$_3$, 201.0 [M−OH]$^+$, 219.1 [MH]$^+$. $^1$H NMR (400 MHz, DMSO-d$^6$): δ. 6.84 (s, 1H), 6.62 (s, 1H), 6.37 (s, 1H), 5.40 (m, 1H), 4.54 (d, J=6 Hz, 2H), 3.70 (s, 3H), 2.20-2.17 (m, 1H), 0.99-0.95 (m, 2H), 0.84-0.82 (m, 2H).

Compound F: (7-isopropyl-5-methoxybenzofuran-2-yl)methanol

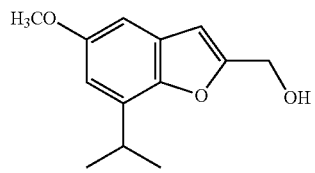 [SMILES: COc1cc(C(C)C)c2oc(CO)cc2c1]

Synthesis of Compound F

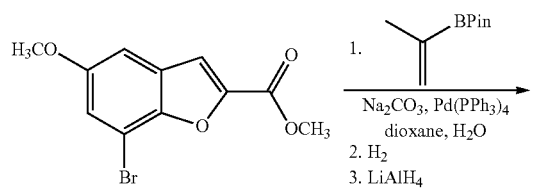

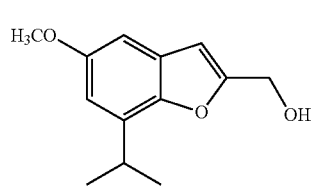

Compound F

To a solution of 2.0 g (7.0 mmol) of methyl 7-bromo-5-methoxybenzofuran-2-carboxylate (prepared in a manner similar to that described for the ethyl ester Int C-2), cyclopropylboronic acid (0.6 g, 8.0 mmol) and $Na_2CO_3$ (2.2 g, 20.7 mmol) in dioxane (80 mL)/$H_2O$ (10 mL) was added Pd(PPh$_3$)$_4$ (0.8 g, 0.7 mmol). The mixture was refluxed overnight then cooled. The reaction mixture was poured into $H_2O$ and extracted with EtOAc (3×20 mL). The combined organic extracts were washed with brine, dried over $MgSO_4$ and concentrated to give a residue which was purified by silica gel column to give 500 mg of the desired ester. A mixture of the olefinic ester (0.5 g, 2.29 mmol) and Pd/C (0.1 g) in ethanol (20 mL) was hydrogenated under 50 psi of hydrogen pressure for 2 h at room temperature. The mixture was filtered and evaporated to provide 400 mg of the desired compound. To a suspension of LiAlH$_4$ (0.305 g, 8.04 mmol) in THF (15 mL) was added dropwise a solution of the intermediate ester (0.50 g, 2.01 mmol) in THF (15 mL) at 0° C. and stirred for 30 min at 0° C. The reaction mixture was poured into water and extracted with EtOAc. The organic extracts were washed with brine, dried over $MgSO_4$ and concentrated to give a residue which was purified by silica gel column to give 350 mg of compound F. LCMS: MS (EI) for $C_{13}H_{16}O_3$, 203.1 [M–OH]+, 221 [MH]+. $^1$H NMR (400 MHz, DMSO-d$^6$): δ 6.86 (1H, d, J=2.4 Hz), 6.69 (1H, d, J=2.4 Hz), 4.64 (2H, s), 3.78 (3H, s), 3.39-3.30 (1H, m), 1.34 (6H, d, J=6.8 Hz).

Compound G: (5-methoxy-7-phenylbenzofuran-2-yl)methanol

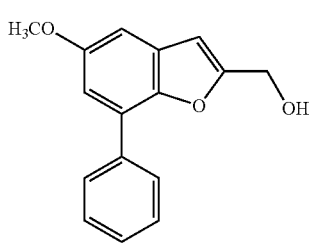 [SMILES: COc1cc(-c2ccccc2)c2oc(CO)cc2c1]

Synthesis of Compound G

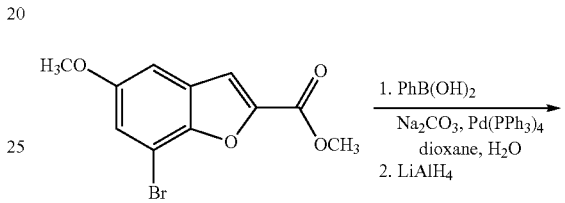

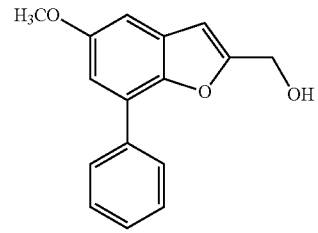

Compound G

To a solution of methyl 7-bromo-5-methoxybenzofuran-2-carboxylate (1.5 mmol), phenylboronic acid (0.18 g, 1.5 mmol) and $Na_2CO_3$ (0.48 g, 4.5 mmol) in dioxane (20 mL)/$H_2O$ (5 mL) was added Pd(PPh$_3$)$_4$ (0.17 g, 0.15 mmol). The mixture was refluxed for 1 h under $N_2$. The reaction mixture was poured into $H_2O$, extracted with EtOAc and the organic extracts were washed with brine, dried over $MgSO_4$ and concentrated to afford 200 mg of the crude coupling product which was redissolved in 15 mL of THF and added drop wise to a suspension of LiAlH$_4$ (0.23 g, 5.96 mmol) in THF (15 mL) at 0° C. The reaction was stirred for 30 min at 0° C. then poured into water and extracted with EtOAc (3×10 mL). The organic extracts were washed with brine and dried over $MgSO_4$ then concentrated to give a residue which was purified by silica gel column to afford 300 mg of compound G. LCMS: MS (EI) for $C_{16}H_{14}O_3$, 237.1 [M–OH]+, 255.1 [MH]+, 277.1 [M+Na]+. $^1$H NMR (400 MHz, DMSO-d$^6$): δ. 7.88-7.85 (m, 2H), 7.54-7.50 (m, 2H), 7.13 (d, J=2.8 Hz, 1H), 7.04 (d, J=2.4 Hz, 1H), 6.76 (s, 1H), 5.47 (t, J=12 Hz, 1H), 4.57 (d, J=6.0 Hz, 2H), 3.83 (s, 3H).

Compound H: (7-(dimethylamino)-5-methoxybenzofuran-2-yl)methanol

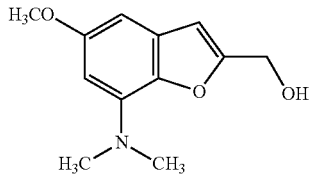 [SMILES: COc1cc(N(C)C)c2oc(CO)cc2c1]

Synthesis of Compound H

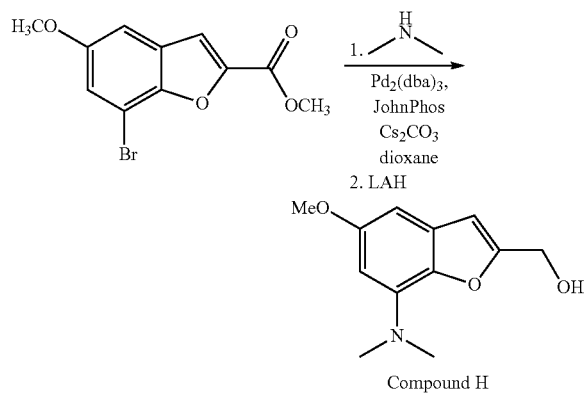

Compound H

To a solution of methyl 7-bromo-5-methoxybenzofuran-2-carboxylate (3.0 g, 10 mmol), dimethylamine (0.57 g, 13 mmol) and Cs$_2$CO$_3$ (12.3 g, 37 mmol) in dioxane (80 mL) was added Pd$_2$(dba)$_3$ (0.75 g, 0.82 mmol) and 450 mg (1.50 mmol) of (2-biphenyl)di-tert-butylphosphine (JohnPhos). The mixture was refluxed overnight under N$_2$ then cooled. The reaction mixture was poured into H$_2$O then extracted with EtOAc (3×20 mL). The organic extracts were washed with brine, dried over MgSO$_4$, concentrated in vacuo to give 700 mg of the desired amino ester. To a suspension of LiAlH$_4$ (0.32 g, 8.43 mmol) in THF (30 mL) was added dropwise a solution of the above mentioned amino ester (0.70 g, 2.81 mmol) in THF (30 mL) at 0° C. and stirred for 30 min. The reaction mixture was poured into H$_2$O and extracted with EtOAc. The organic extracts were washed with brine, dried over MgSO$_4$, concentrated in vacuo to give a residue which was purified by silica gel column to give compound H (0.39 g). LCMS: MS (EI) for C$_{12}$H$_{15}$NO$_3$, 222.1 [MH]+. $^1$H NMR (400 MHz, DMSO-d$^6$): S. 6.57 (d, J=0.4 Hz, 1H), 6.54 (d, J=2.4 Hz, 1H), 6.24 (s, 1H), 4.63 (s, 2H), 3.76 (s, 3H), 6.76 (s, 1H), 2.97 (s, 6H).

Compound I: (5-methoxy-7-(methyl(phenyl)amino)benzofuran-2-yl)methanol

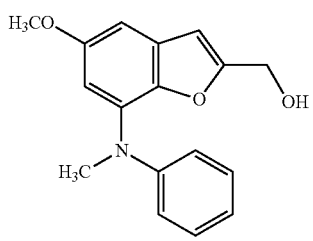 [SMILES: COc1cc(N(C)c2ccccc2)c2oc(CO)cc2c1]

Synthesis of Compound I

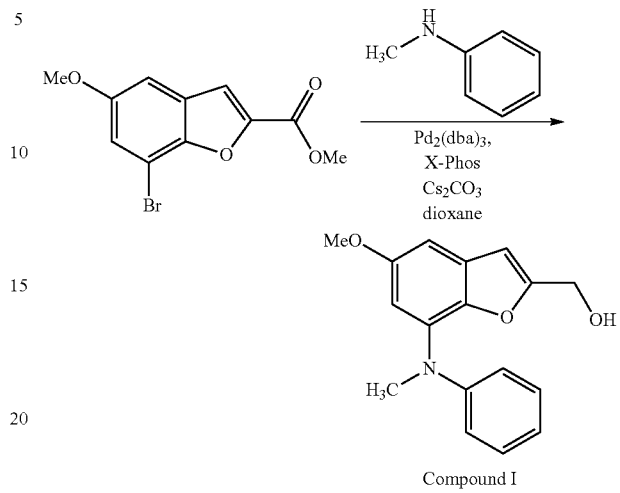

Compound I

To a solution of methyl 7-bromo-5-methoxybenzofuran-2-carboxylate (3.0 g, 10 mmol), N-methylaniline (1.36 g, 12 mmol) and Cs$_2$CO$_3$ (12.3 g, 37 mmol) in dioxane (80 mL) was added Pd$_2$(dba)$_3$ (0.75 g, 0.82 mmol) and X-Phos (0.43, 1.44 mmol). The mixture was refluxed overnight under N$_2$. The reaction mixture was cooled then poured into water and extracted with EtOAc. The organic extracts were washed with brine, dried over MgSO$_4$ and concentrate to give a residue which was purified by silica gel column to give 1.1 g of the desired C—N coupling product which was used directly in the next step. To a suspension of LiAlH$_4$ (0.20 g, 5.77 mmol) in THF (20 mL) was added dropwise a solution of the above described ester (0.60 g, 1.92 mmol) in THF (20 mL) at 0° C. The reaction mixture was stirred for 30 min at 0° C. then poured into H$_2$O and extracted with EtOAc. The organic extracts were washed with brine dried over MgSO$_4$ and concentrated. The residue was purified by silica gel column to give compound I (0.35 g) as a white solid. LCMS: MS (EI) for C$_{17}$H$_{17}$NO$_3$, 284.2 [M+H]+. $^1$H NMR (400 MHz, CD$_3$OD): δ. 7.20-7.17 (m, 2H), 6.89-6.85 (m, 1H), 6.84-6.79 (m, 3H), 6.67-6.64 (m, 1H), 6.64-6.63 (m, 1H), 4.58 (s, 2H), 3.80 (s, 3H), 3.30 (s, 3H).

Compound J: (5-methoxy-7-(4-methylpiperazin-1-yl)benzofuran-2-yl)methanol

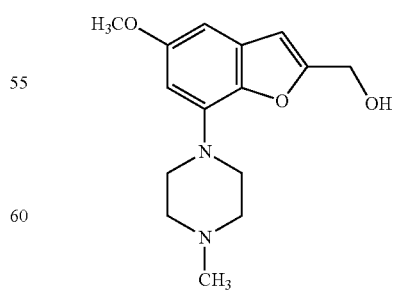

Similar two-step procedure as described for the synthesis of Compound I using N-methylpiperazine as the amine. LCMS: (EI) for C$_{15}$H$_{20}$N$_2$O$_3$, 277.2 [MH]+. $^1$H NMR (400

MHz, MeOD): δ 6.67 (1H, s), 6.63 (1H, s), 6.37 (1H, s), 4.65 (2H, s), 3.80 (3H, s), 3.36-3.30 (4H, m), 2.70-2.68 (3H, m).

Compound K: (5-methoxy-7-morpholinobenzofuran-2-yl)methanol

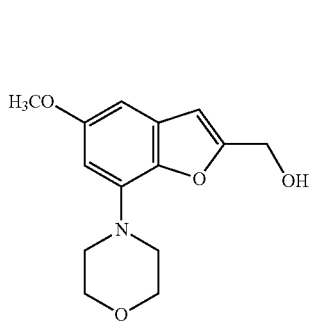 [SMILES: COc1cc(N2CCOCC2)c2oc(CO)cc2c1]

Similar two-step procedure as described for the synthesis of Compound I using morpholine as the amine. LCMS: (EI) for $C_{14}H_{17}N_4O$, 264.1 [MH]$^+$. $^1$H NMR (400 MHz, MeOD): δ 6.65 (s, 1H), 6.60 (s, 1H), 6.34 (s, 1H), 4.62 (s, 2H), 3.88-3.86 (m, 4H), 3.77 (s, 3H), 3.30-3.26 (m, 4H).

Compound L: 4-(2-(hydroxymethyl)-5-methoxybenzofuran-7-yl)thiomorpholine 1,1-dioxide

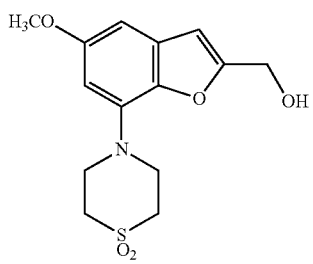 [SMILES: COc1cc(N2CCS(=O)(=O)CC2)c2oc(CO)cc2c1]

Similar two-step procedure as described for the synthesis of Compound I using thiomorpholine 1,1-dioxide as the amine. LCMS: (EI) for $C_{14}H_{17}NO_5S$, 312.0 [MH]$^+$. $^1$H NMR (400 MHz, DMSO): δ 6.70 (s, 1H), 6.66 (s, 1H), 6.41 (s, 1H), 5.49-5.44 (m, 1H), 4.54-4.52 (m, 2H), 3.82-0.80 (m, 4H), 3.75 (s, 3H), 3.27-3.24 (m, 4H).

Compound M: (7-(1,1-difluoroethyl)-5-methoxybenzofuran-2-yl)methanol

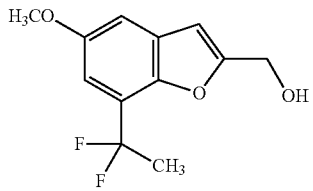 [SMILES: COc1cc(C(C)(F)F)c2oc(CO)cc2c1]

Step A: Preparation of Int M-1

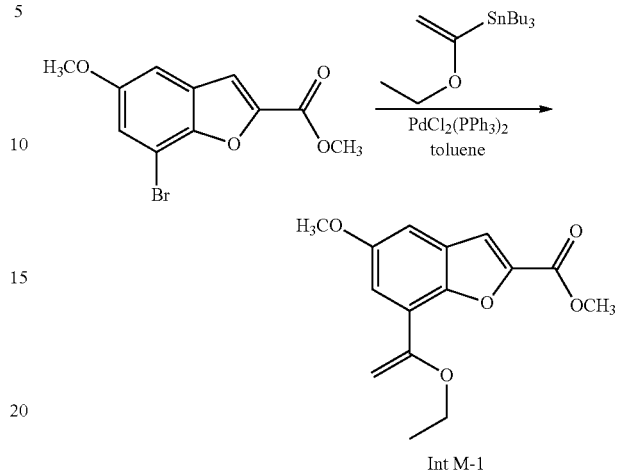

To a solution of methyl 7-bromo-5-methoxybenzofuran-2-carboxylate (2.85 g, 10 mmol) in (100 mL) was added (1-ethoxy)-tributylstannane (6.31 g, 17.5 mmol) and PdCl$_2$(PPh$_3$)$_3$ (0.7 g, 1.0 mmol). The mixture was stirred overnight at 50° C. under N$_2$. The reaction mixture was poured into H$_2$O, extracted with EtOAc and the organic extracts were washed with brine, dried over MgSO$_4$, concentrated in vacuo to give 2.0 g of a residue which was used directly in the next step without further purification.

Step B: Preparation of Int M-2

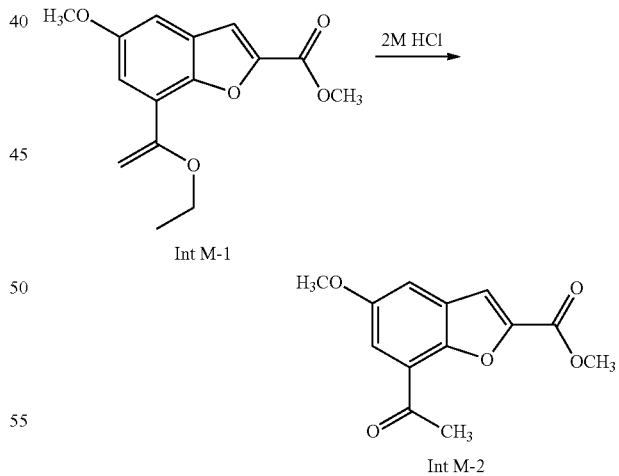

To a solution of Int M-1 (2.0 g, 7.25 mmol) in dioxane (100 mL) was added 2M HCl (9 mL, 18 mmol). The mixture was stirred for 30 min at room temperature then diluted with EtOAc. The organic phase was washed twice with saturated NaHCO$_3$ then water then brine. The organics were dried over MgSO$_4$ and concentrated in vacuo to afford 1.2 g of Int M-2 which was used directly in the next step without purification.

Step C: Preparation of Int M-3

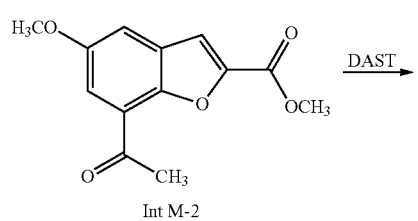

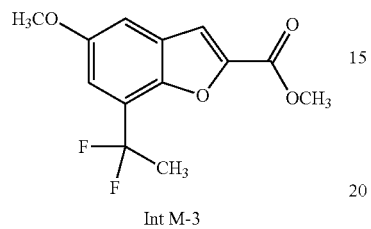

A solution of Int M-2 (0.9 g, 0.88 mmol) in DAST (6 mL) was stirred overnight at 60° C. The reaction mixture was cooled and treated with 1 mL of water very slowly. The resulting mixture was extracted with EtOAc (3×20 mL) and the organic extracts were washed with brine and dried over MgSO$_4$. Evaporation of the solvent provided 450 mg of Int M-3 as an off-white solid.

Step D: Preparation of Compound M

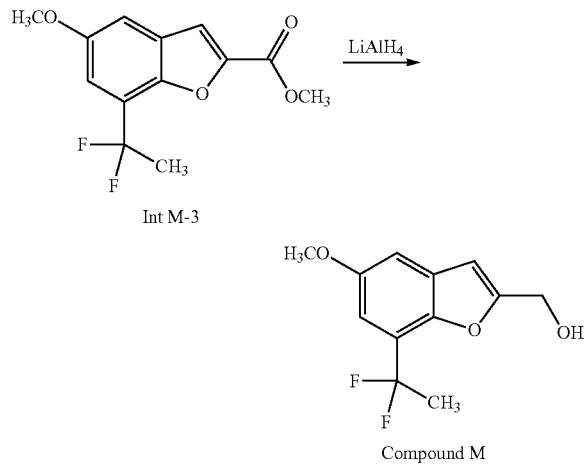

To a suspension of LiAlH$_4$ (0.18 g, 4.93 mmol) in THF (20 mL) was added dropwise a solution of Int M-3 (0.45 g, 1.67 mmol) in THF (20 mL) at 0° C. The reaction mixture was stirred for 30 min at 0° C. then poured into H$_2$O and extracted with EtOAc. The organic extracts were washed with brine dried over MgSO$_4$ and concentrated. The residue was purified by silica gel column to give compound M (0.27 g) as a white solid. LCMS: MS (EI) for C$_{12}$H$_{12}$F$_2$O$_3$, 223.0 [M−OH]$^+$. $^1$H NMR (400 MHz, MeOD): δ 7.16 (s, 1H), 6.97 (s, 1H), 6.70 (s, 1H), 4.66 (s, 2H), 3.82 (s, 3H), 2.10 (t, J=18.8 Hz, 3H).

Compound N: (5,7-dimethylbenzofuran-2-yl)methanol

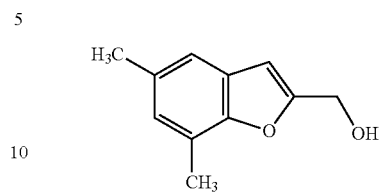

Step A: Preparation of Int N-1

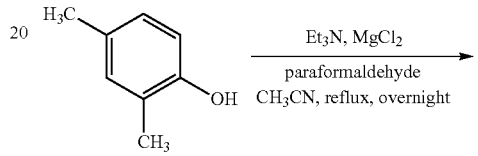

To a solution of 2,4-dimethylphenol (80 g, 0.66 mol) in CH$_3$CN (2000 mL) was added Et$_3$N (248 g, 2.46 mol) and MgCl$_2$ (93 g, 0.99 mol) in one portion at room temperature. The mixture was stirred at room temperature for 1 h and then (CH$_2$O)$_n$ was added. The resulting mixture was heated to reflux and stirred overnight. The mixture was cooled to room temperature and then poured into a stirred 5% HCl (500 mL) solution. The mixture was extracted with EtOAc (3×400 mL). The combined organic extracts were washed with brine (300 mL) and separated. The organic layer was dried over anhydrous Na$_2$SO$_4$, filtered and concentrated under reduce pressure. The residue was purified by column chromatography (column height: 50 cm, diameter: 20 cm, 100-200 mesh silica gel, petroleum ether/EtOAc=10/1) to give Int N-1 (58 g) as a yellow solid. $^1$H NMR: (CDCl$_3$, 400 MHz): δ 10.87 (s, 1H), 9.82 (s, 1H), 6.81 (s, 1H), 2.29 (s, 6H).

Step B: Preparation of Int N-2

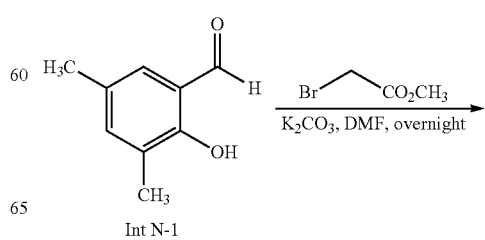

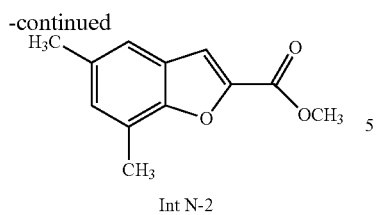

Int N-2

To a mixture of Int N-1 (58 g, 0.386 mol) and $K_2CO_3$ (160 g, 1.16 mol) in DMF (1.2 L) was added methyl 2-bromoacetate (88.2 g, 0.58 mol) in one portion at room temperature under $N_2$. The mixture was stirred at room temperature for 10 min then heated to 100° C. and stirred overnight. The suspension was cooled to room temperature and filtered. The filter cake was washed with EtOAc (500 mL×3) and the filtrate concentrated to remove most of EtOAc. The resulting DMF solution was poured into ice-water (w/w=1/1) (1 L) and stirred for 20 min at room temperature. A brown solid was collected by filtration. The filter cake was washed with water (200 mL) and then dried with high vacuum (Vacuum Dryer with $P_2O_5$, oil pump make the pressure <10 Pa) to afford crude Int N-2 which was washed with PE/EA (v/v=5/1, 600 mL). The residual solvent was removed with rotary-evaporator to afford pure Int N-2 (40 g) as brown solid. $^1$H NMR: (CDCl$_3$, 400 MHz): δ 7.38 (s, 1H), 7.36 (s, 1H), 7.30 (s, 1H), 3.93 (s, 3H), 2.34 (s, 3H), 2.28 (s, 3H). LCMS: MS cal.: 204.1; MS found: 205.1.

Step C: Preparation of Compound N

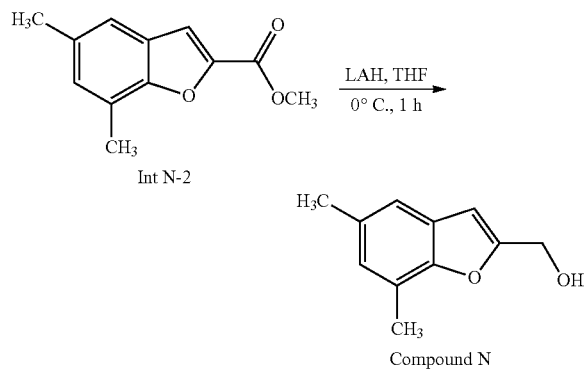

Int N-2

Compound N

To a stirred suspension of LAH (4.5 g, 118 mmol) in anhydrous THF (100 mL) was added dropwise Int N-2 (12 g, 60 mmol) at 4° C. (ice-water bath) under $N_2$. The mixture was stirred at 0° C. for 1 h before the mixture was quenched by the dropwise addition of water (50 mL) taking care to control the internal temperature below 10° C. The suspension was filtered and the filter cake was washed with THF (100 mL). The filtrate was concentrated and the residue was washed with petroleum ether/EtOAc=8/1 to afford Compound N (8 g) as white solid. $^1$H NMR: (CDCl$_3$, 400 MHz): δ 7.30 (s, 1H), 7.25 (s, 1H), 6.56 (s, 1H), 4.74 (d, J=6.0 Hz, 2H), 2.37 (t, J=13.0 Hz, 6H), 1.92 (t, J=6.2 Hz, 1H). $^{13}$C NMR: (CDCl$_3$, 100 MHz): δ 155.3, 153.7, 133.1, 130.9, 125.6, 120.8, 111.3, 103.4, 57.8, 20.1, 19.5. LCMS: purity: 98.4%; MS cal.: 176.1; MS found: 159.1 [M−OH]. Melting point: 96.4° C.-97.1° C.

Compound O: (4-((5,7-dimethoxybenzofuran-2-yl)methoxy)phenyl)methanol

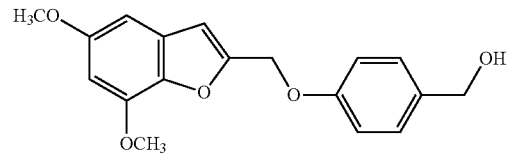 [SMILES: COc1cc(OC)c2oc(COc3ccc(CO)cc3)cc2c1]

Step A: Synthesis of Int O-1

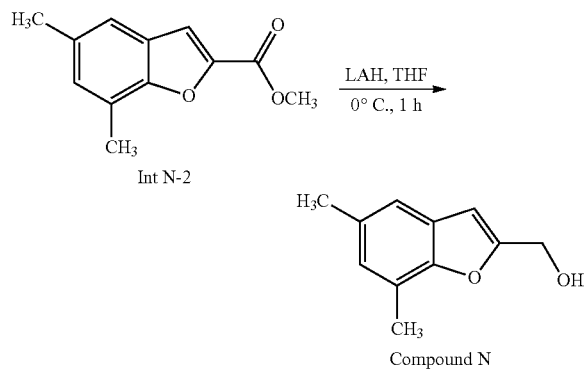

Compound B

Int O-1

To a suspension of Compound B (30.0 g, 0.144 mol), ethyl 4-hydroxybenzoate (28.7 g, 0.173 mol) and PPh$_3$ (18.8 g, 0.187 mol) in anhydrous THF (300 mL) was added DEAD (32.2 g, 0.187 mol) dropwise at 4° C. (ice-water batch) over 30 min. After the addition was complete, the reaction mixture was allowed to stir at room temperature for 15 h. The mixture was poured into water and extracted with DCM (200 mL×3). The combined organic extracts were dried over Na$_2$SO$_4$. The filtrate was concentrated under reduced pressure. The residue was purified by column chromatography (column height: 20 cm, diameter: 5 cm, 100-200 mesh silica gel, petroleum ether/EtOAc=5/1) to afford crude Int O-1 (20 g, 85% $^1$H NMR purity) as an off-white solid. $^1$H NMR (400 MHz, CDCl$_3$): δ 8.01 (d, J=9.26 Hz, 2H), 7.01 (d, J=8.82 Hz, 2H), 6.74 (s, 1H), 6.60 (d, J=2.21 Hz, 1H), 6.47 (d, J=2.21 Hz, 1H), 5.20 (s, 2H), 4.36 (q, J=7.06 Hz, 2H), 3.92-4.06 (m, 3H), 3.77-3.89 (m, 3H), 1.39 (t, J=7.28 Hz, 3H).

Step B: Synthesis of Compound O

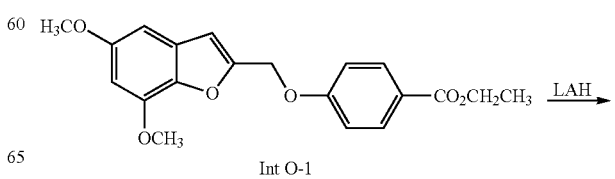

Int O-1

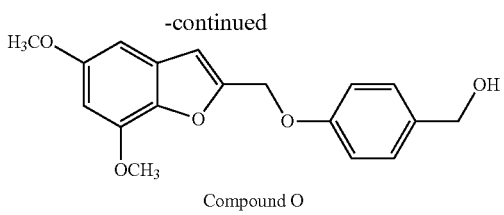

Compound O

To a suspension of LAH (2.87 g, 0.075 mol) in anhydrous THF (200 mL) was added Int 0-1 (18 g, 0.050 mol) in portions at 4° C. (ice-water bath) over 30 min under nitrogen. After the addition was complete the reaction mixture was allowed to stir at room temperature for 12 h. Water (3 ml) was added dropwise at 0° C., then 15% NaOH aqueous (3 ml) and $H_2O$ (15 ml) were added. After stirring 30 min, $MgSO_4$ (40 g) was added and the mixture was stirred another 30 min. Then mixture was filtered off and the filtrate was concentrated under reduced pressure. The residue was purified by column chromatography (column height: 20 cm, diameter: 5 cm, 100-200 mesh silica gel, petroleum ether/EtOAc=5:1) to afford Compound O (11 g) as off-white solid. LCMS: 315.1 [M+H] $^1$H NMR (400 MHz, DMSO): δ 7.24 (d, J=8.03 Hz, 2H), 7.00 (d, J=8.03 Hz, 2H), 6.93 (s, 1H), 6.93 (s, 1H), 6.70 (s, 1H), 6.54 (s, 1H), 5.19 (s, 2H), 5.05 (t, J=5.52 Hz, 1H), 4.41 (d, J=5.52 Hz, 2H), 3.89 (s, 3H), 3.76 (s, 3H). $^{13}$C NMR (100 MHz, DMSO-d$^6$): δ 157.14, 156.98, 145.56, 139.40, 135.67, 1129.40, 128.38, 114.91, 107.67, 97.78, 96.33, 63.00, 62.56, 56.214, 56.00, 40.61, 40.41, 40.26, 39.99, 39.78, 39.57, 39.37. MP: 128.5° C.-129.5° C.

Compound P: (4-((5,7-bis(methoxy-d$^3$)benzofuran-2-yl)methoxy)phenyl)methanol

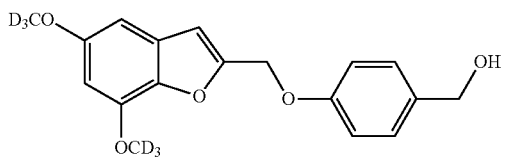 [SMILES: COc1cc(C)c2oc(COc3ccc(CO)cc3)cc2c1]

Similar two-step procedure as described for the synthesis of Compound O using Compound C as the starting material. LCMS: MS cal.: 320.2, MS found: 321.1 [M+H]$^+$. $^1$H NMR (400 MHz, DMSO-d$^6$): a 7.25 (d, J=8.8 Hz, 2H), 7.02 (d, J=8.8 Hz, 2H), 6.94 (s, 1H), 6.70 (d, J=2.4 Hz, 1H), 6.54 (d, J=2.4 Hz, 1H), 5.20 (s, 2H), 5.07 (t, J=6 Hz, 1H), 4.42 (d, J=5.6 Hz, 2H). MP: 130.6° C.-131.2° C.

Compound Q: (4-((5-methoxy-7-methylbenzofuran-2-yl)methoxy)phenyl)methanol

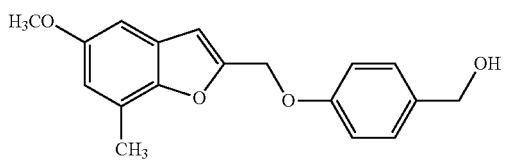

Similar two-step procedure as described for the synthesis of Compound O using Compound D as the starting material. LCMS: MS cal.: 298.12; MS found: 321.0 [M+Na]. $^1$H NMR (400 MHz, CDCl$_3$): δ 7.29 (d, J=8.4 Hz, 2H), 6.99 (d, J=8.4 Hz, 2H), 6.82 (d, J=2.0 Hz, 1H), 6.71-6.68 (m, 2H), 5.13 (s, 2H), 4.61 (s, 2H), 3.80 (s, 3H), 2.47 (s, 3H), 1.63 (br, 1H). $^{13}$C NMR (100 MHz, CDCl$_3$): δ 157.9, 155.9, 153.2, 149.5, 133.9, 128.6, 127.8, 122.3, 115.0, 114.4, 106.6, 100.8, 64.9, 63.3, 55.8, 15.2. Melting Point: 101.6° C.-102.3° C.

Compound R: (4-((5,7-dimethylbenzofuran-2-yl)methoxy)phenyl)methanol

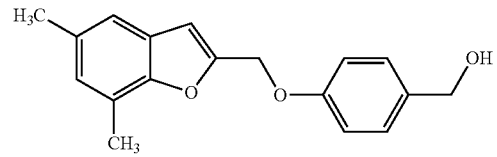

Similar two-step procedure as described for the synthesis of Compound N using Compound N as the starting material. LCMS: MS cal.: 282.13; MS found: 305.0 [M+Na]. $^1$H NMR (400 MHz, CDCl$_3$): δ 7.31 (d, J=9.2 Hz, 4H), 7.02 (d, J=8.4 Hz, 2H), 6.70 (s, 1H), 4.64 (d, J=3.6 Hz, 2H), 2.37 (d, J=12.0 Hz, 6H), 1.75 (s, 1H). $^{13}$C NMR (100 MHz, CDCl$_3$): δ 157.9, 154.2, 151.9, 133.8, 131.4, 128.6, 125.8, 121.2, 115.1, 111.8, 105.9, 64.9, 63.2, 20.5, 19.9. Melting Point: 133.8° C.-135.6° C.

Compound S: (E)-3-(5,7-dimethylbenzofuran-2-yl)prop-2-en-1-ol

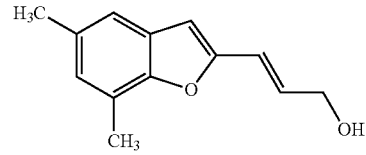

Step A: Preparation of Int S-1

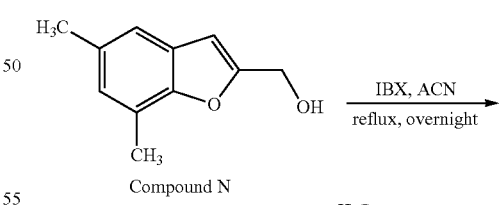

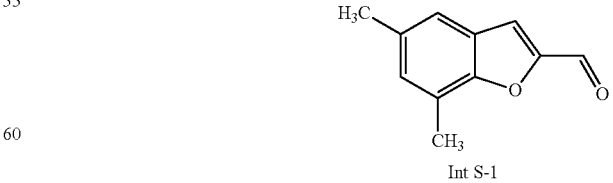

To a solution of Compound N (30 g, 0.170 mol) in acetonitrile (300 mL) was added IBX (104.3 g, 0.340 mol) and the mixture was heated to reflux and stirred overnight. The mixture was cooled to room temperature and filtered.

The filter cake was washed with EtOAc (100 mL) and the solvent was concentrated to give Int S-1 (27 g) as colorless oil. $^1$H NMR: (CDCl$_3$, 400 MHz): δ 9.81 (s, 1H), 7.48 (d, J=4.0 Hz, 2H), 7.38 (s, 1H), 2.39 (d, J=18.0 Hz, 6H).

Step B: Preparation of Int S-2

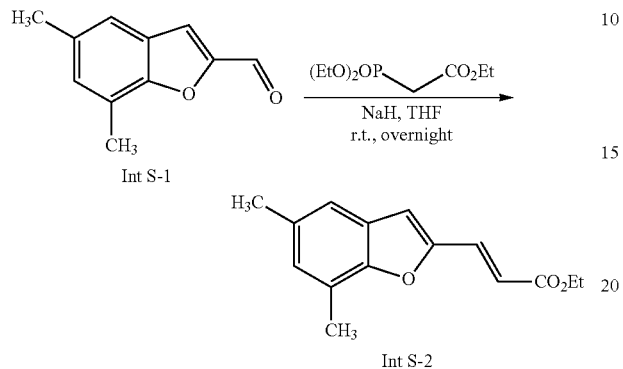

To a mixture of NaH (3.3 g, 0.139 mol) in THF (50 mL) was added triethyl phosphonoacetate (31.2 g, 0.139 mol) at 0° C. (ice-water bath). After the addition the mixture was stirred at 0° C. for 1 h. A solution of Int S-1 (22 g, 0.126 mol) in THF (150 mL) was then added dropwise at 0° C. and the mixture was allowed to warm to ambient temperature overnight. The solvent was poured into ice water and extracted with EtOAc (200 mL). The organic extract was dried over anhydrous Na$_2$SO$_4$ and concentrated to give 16.5 g of Int S-2 as a white solid. $^1$H NMR (400 MHz, CDCl$_3$): δ 7.49 (d, J=16.0 Hz, 1H), 7.29 (s, 1H), 7.23 (s, 1H), 6.80 (s, 1H), 6.49 (d, J=16.0 Hz, 1H), 4.28 (m, 2H), 2.32 (d, J=18.0 Hz, 6H), 1.32 (t, J=7.2 Hz, 3H).

Step C: Preparation of Compound S

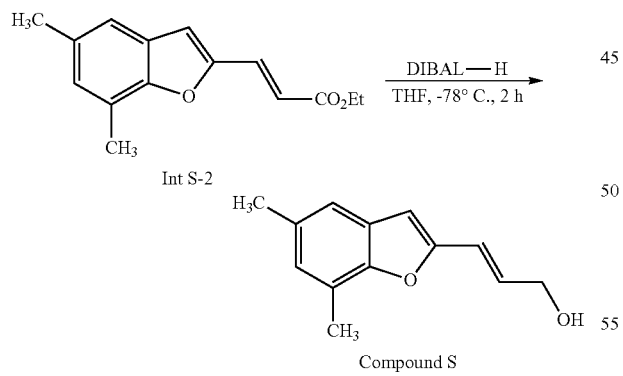

To a stirred solution of Int S-2 (21 g, 0.086 mol) in anhydrous THF (200 mL) at 4° C. (ice-water bath) was added DIBAL-H (206 mL, 0.206 mol) dropwise to keep the reaction temperature between −78° C. and −65° C. under nitrogen. Then the mixture was warmed to room temperature and the reaction was quenched with water (20 mL) and anhydrous MgSO$_4$ (200 g) was added then stirred for 1 h. The mixture was filtered and the filter cake was washed with EtOAc (200 mL×2). The solvent was concentrated to give 10.4 g of Compound S. $^1$H NMR (400 MHz, DMSO-d$^6$): a 7.31 (s, 2H), 6.69 (s, 1H), 6.57 (d, J=16.0 Hz, 1H), 6.44 (d, J=16.0 Hz, 1H), 4.98 (t, J=5.6 Hz, 1H), 4.17 (t, J=4.4 Hz, 2H), 2.28 (d, J=14.8 Hz, 6H). $^{13}$C NMR (100 MHz, CDCl$_3$): δ 153.8, 153.6, 133.7, 131.3, 129.7, 126.7, 121.0, 119.3, 111.4, 104.4, 63.1, 20.5, 19.9. LCMS: MS cal.: 202.1; MS found: 185 [M−OH]. Melting Point: 104.6° C.-106.3° C.

Compound T: (E)-3-(5-methoxy-7-methylbenzofuran-2-yl)prop-2-en-1-ol

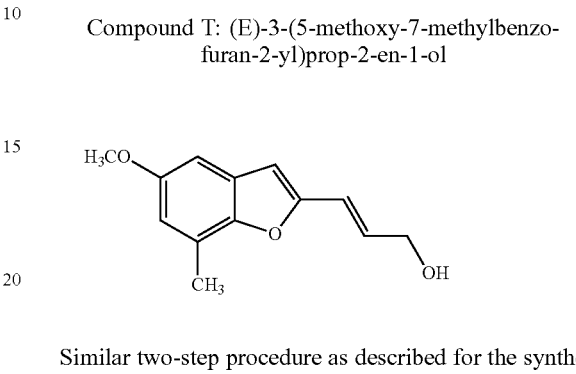

Similar two-step procedure as described for the synthesis of Compound S using Compound D as the starting material. $^1$H NMR: (DMSO-d$_6$, 400 MHz): δ 6.85 (s, 1H), 6.67 (d, J=10.4 Hz, 2H), 6.56-6.43 (m, 2H), 4.96 (t, J=5.2 Hz, 1H), 4.14 (s, 2H), 3.73 (s, 3H), 2.38 (s, 3H). $^{13}$C NMR: (DMSO-ds, 100 MHz): δ 156.0, 155.3, 148.4, 133.4, 129.1, 121.5, 117.5, 114.1, 104.8, 101.3, 61.8, 55.8, 15.2. LCMS cal.: 218.09; MS found: 201.1 [M−OH+1].

Compound U: (E)-3-(5,7-bis(methoxy-d3)benzofuran-2-yl)prop-2-en-1-ol

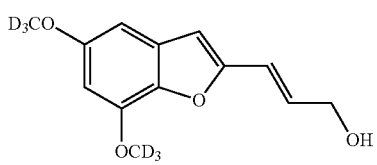

Similar two-step procedure as described for the synthesis of Compound S using Compound C as the starting material. $^1$H NMR: (DMSO-d$_6$, 400 MHz): δ 6.74 (s, 1H), 6.65 (s, 1H), 6.64-6.55 (m, 1H), 6.55-6.48 (m, 2H), 5.00 (s, 1H), 4.15 (d, J=4 Hz, 2H). $^{13}$C NMR: (DMSO-d$_6$, 100 MHz): δ 156.9, 155.3, 145.2, 138.7, 133.6, 130.4, 117.3, 104.8, 97.6, 95.1, 61.2. LCMS: MS cal.: 240.13; MS found: 223.1 [M−OH], 241.1 [M+1], 263.0 [M+Na]. Melting Point: 86.5° C.-87.0° C.

Compound V: (5,6,7-trimethoxybenzofuran-2-yl)methanol

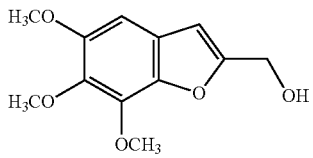 [SMILES: COc1cc2cc(CO)oc2c(OC)c1OC]

Step A: Synthesis of Int V-1

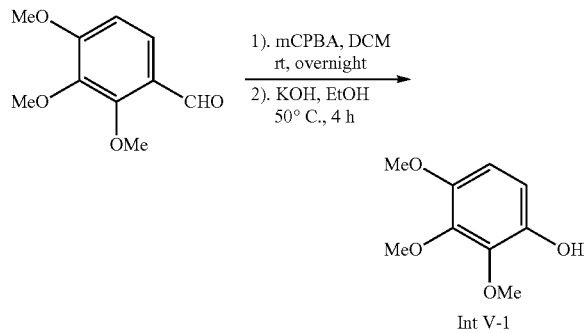

To a solution containing 150.0 g (0.77 mol) of 2,3,4-trimethoxybenzaldehyde in 1000 mL of DCM was added 300.0 g (1.74 mol) of m-CPBA in five portions (30 g each) at 0° C.-10° C. (ice-water bath). After the addition the reaction mixture was warmed to room temperature and stirred overnight. The reaction mixture was filtered to remove the solid and the filtrate was washed with aqueous NaHCO$_3$ (400 mL×3), water (300 mL) and brine (300 mL). The organic layer was separated and dried over anhydrous Na$_2$SO$_4$ and the mixture was filtered. The filtrate was concentrated to provide a dark yellow colored oil which was dissolved in EtOH (600 mL) and treated with a 10% aqueous KOH solution (500 mL) in one portion. The mixture was stirred at 50° C. for 4 h. The mixture was then cooled and acidified to pH=1 with 1 M HCl and extracted with DCM (500 mL×3). The combined organic extracts were washed with water (500 mL) and brine (500 mL), dried over anhydrous Na$_2$SO$_4$ and then filtered. The filtrate was concentrated and purified by silica gel chromatography (column height: 50 cm, diameter: 20 cm, 100-200 mesh silica gel, petroleum ether/EtOAc=30/1, 20/1, 15/1, 10/1) to give Int V-1 (79.0 g) as yellow oil. $^1$H NMR: (CDCl$_3$, 400 MHz): δ 6.63 (d, J=8 Hz, 1H), 6.55 (d, J=8 Hz, 1H), 5.38 (brs, 1H), 3.96 (s, 3H), 3.90 (s, 3H), 3.81 (s, 3H).

Step B: Synthesis of Int V-2

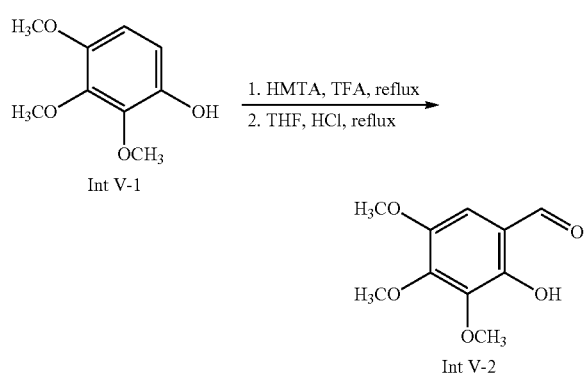

A mixture of Int V-1 (74 g, 400 mmol), HMTA (67.6 g, 480 mmol) and TFA (500 mL) was refluxed under N$_2$ for 20 h. The solution was cooled to room temperature and concentrated under vacuum. Toluene (200 mL) was added to the residue and the solution was further concentrated to remove trace amount of TFA. The residual oil was treated with THF (300 mL) and 2 M HCl (300 mL) and then heated to reflux for 2 h. The solution was cooled to room temperature and extracted with DCM (300 mL×3). The combined organic layers were washed with water (300 mL) and brine (300 mL), dried over anhydrous Na$_2$SO$_4$ and then filtered. The filtrate was concentrated and purified by silica gel chromatography (column height: 50 cm, diameter: 20 cm, 100-200 mesh silica gel, petroleum ether/EtOAc=30/1, 20/1, 15/1, 10/1) to give Int V-2 (36.0 g) as yellow solid. $^1$H NMR: (CDCl$_3$, 400 MHz): δ 10.96 (s, 1H), 9.75 (s, 1H), 6.75 (s, 1H), 4.03 (s, 3H), 3.92 (s, 3H), 3.84 (s, 3H).

Step C: Synthesis of Int V-3

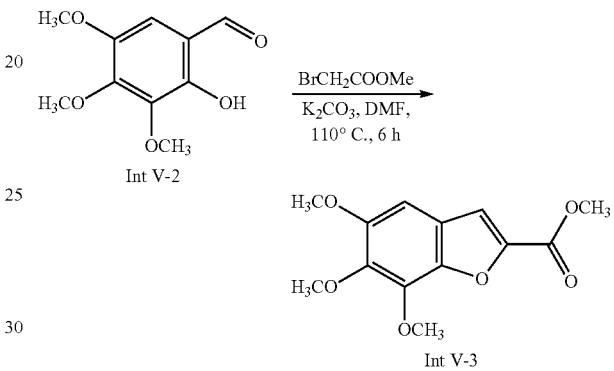

To a solution of Int V-2 (36 g, 0.17 mol) in anhydrous DMF (200 mL) was added K$_2$CO$_3$ (46.9 g, 0.34 mol) and methyl bromoacetate (28.4 g, 0.19 mol) at room temperature. The resulting solution was heated to 110° C. and stirred for 6 hours. The suspension was cooled and filtered through a pad of celite. The filter cake was washed with EtOAc (500 mL) and the filtrate was concentrated. The residual oil was purified by silica gel chromatography (column height: 30 cm, diameter: 10 cm, 100-200 mesh silica gel, petroleum ether/EtOAc=15/1, 10/1, 5/1) to give Int V-3 (14 g) as white solid. $^1$H NMR: (CDCl$_3$, 400 MHz): δ 7.41 (s, 1H), 6.76 (s, 1H), 4.20 (s, 3H), 3.93 (s, 3H), 3.90 (s, 3H), 3.87 (s, 3H).

Step D: Synthesis of Compound V

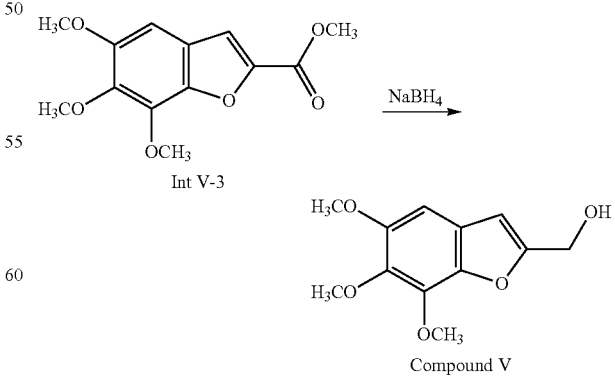

To a solution of compound Int V-3 (14 g, 52.63 mmol) in anhydrous MeOH (100 mL) was added NaBH$_4$ (10 g, 263.16 mmol) in ten portions (1 g for each portion) at 0-10° C. (ice-water bath) and the resulting mixture was stirred at 30° C. for 3 hours. The suspension was filtered and the filtrate was concentrated to give 10.6 g of Compound V as a white solid. MP: 68.2° C.-68.7° C. LCMS: MS cal.: 238.08, [M+H]+=239.1. ¹H NMR: (CDCl₃, 400 MHz): δ 6.74 (s, 1H), 6.60 (s, 1H), 4.77 (d, J=6.3 Hz, 2H), 4.21 (s, 3H), 3.91 (d, J=5.3 Hz, 6H), 1.95 (t, J=6.4 Hz, 1H).

Compound W:
(4,5,7-trimethoxybenzofuran-2-yl)methanol

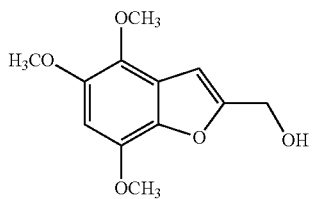

Similar three-step procedure as described for the synthesis of Compound V using as 2,4,5-trimethoxybenzaldehyde as the starting material. LCMS: MS cal.: 238.08, [M+H]+=239.1. ¹H NMR: (CDCl₃, 400 MHz): δ 6.77 (s, 1H), 6.55 (s, 1H), 4.76 (d, J=5.6 Hz, 2H), 4.01 (s, 3H), 3.94 (s, 3H), 3.92 (s, 3H), 2.13 (t, J=6 Hz, 1H). ¹³C NMR: (CDCl₃, 100 MHz): δ 157.2, 146.8, 140.6, 139.7, 135.5, 123.2, 101.8, 96.7, 60.9, 57.9, 57.7, 56.8.

Compound X:
(5,7-dimethoxy-3-methylbenzofuran-2-yl)methanol

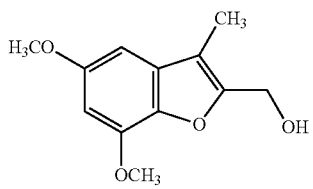 [SMILES: COc1cc(OC)c2oc(CO)c(C)c2c1]

Step A: Synthesis of Int X-1

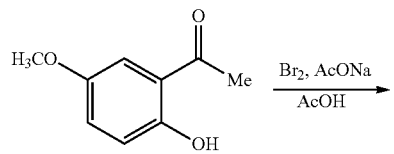

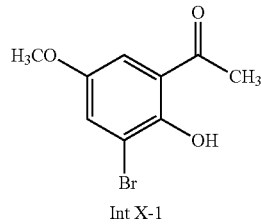

2-Hydroxy-5-methoxyacetophenone (200 g, 1200 mmol) and anhydrous NaOAc (104 g, 1264 mmol) were added to 2000 mL of AcOH in one portion at room temperature. Bromine (199 g, 1.264 mol) in 300 mL of AcOH was then added at room temperature dropwise with a dropping funnel over 2 h keeping the internal reaction temperature between 15-25° C. (water bath). After the addition was complete, the mixture was stirred at room temperature for 16 h then poured into iced water (w/w=1/1, 8 L) and stirred for 1 h. Then the mixture was filtered and the filter cake was washed with water (3×1 L) then dried in air for 2 days to afford Int X-1 (210 g) as yellow solid. ¹H NMR (400 MHz, CDCl₃): δ 12.45 (s, 1H), 7.39 (d, J=2.8 Hz, 1H), 7.20 (d, J=2.4 Hz, 1H), 3.80 (s, 3H), 2.64 (s, 3H).

Step B: Synthesis of Int X-2

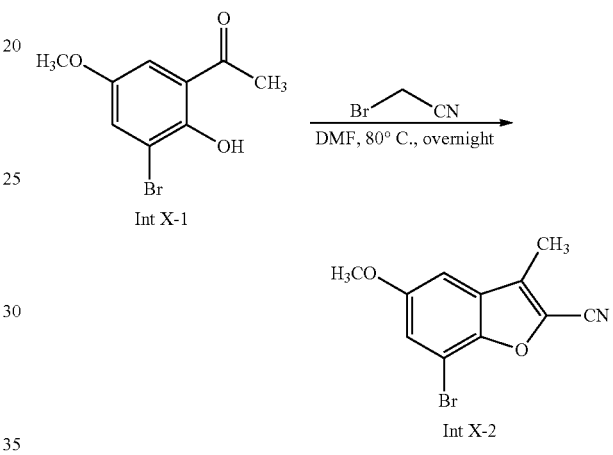

To a mixture of Int X-1 (100 g, 0.408 mol) and 2-bromoacetonitrile (73 g, 0.612 mol) in DMF (1 L) was added K₂CO₃ (169 g, 1.224 mol) in one portion at room temperature. The mixture then heated to 80° C. under N₂ and stirred overnight. The suspension was cooled to room temperature and poured into 2000 mL of ice/water/brine (v/v/v=1/1/2) and the mixture was extracted with EtOAc (3×1000 mL). The combined organic extracts were washed with water (3×1000 mL) then brine (3×1000 mL) and dried over anhydrous Na₂SO₄. The mixture was filtered and the filtrate was concentrated. The residue was purified by silica gel column (column height: 60 cm, diameter: 20 cm, 100-200 mesh silica gel, petroleum ether/EtOAc=5/1 to 3/1) to afford Int X-2 (38 g) as yellow solid. ¹H NMR (400 MHz, CDCl₃): δ 7.22 (d, J=2.0 Hz, 1H), 6.85 (d, J=2.0 Hz, 1H), 3.79 (s, 3H), 2.35 (s, 3H).

Step C: Synthesis of Int X-3

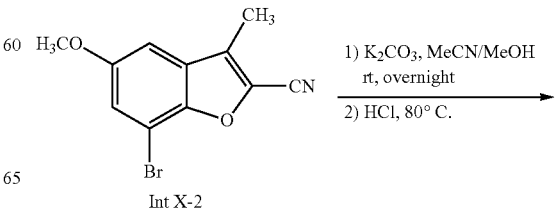

-continued

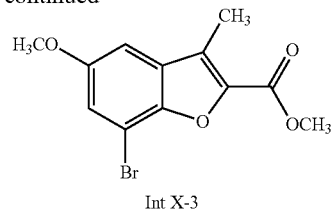
Int X-3

To a solution of Int X-2 (50 g, 188 mmol) in MeOH/MeCN (600 mL, v/v=1/1) was added K$_2$CO$_3$ (182 g, 1316 mmol) in one portion at room temperature. The mixture was stirred at room temperature overnight. The mixture was filtrated and the filtrate was poured into water (800 mL) and extracted with EtOAc (3×400 mL). The combined organic extracts were washed with brine (3×500 mL) and dried over anhydrous Na$_2$SO$_4$. The mixture was filtered and the filtrate was concentrated. The residue was redissolved in 1M HCl (500 mL) and MeOH (100 mL). The mixture was heated to 80° C. for 2 h before the reaction was cooled and filtered. The solids were washed with water (800 mL×3) and then dried to afford Int X-3 (34.3 g) as white solid. $^1$H NMR (400 MHz, CDCl$_3$): δ 7.26 (d, J=2.0 Hz, 1H), 6.95 (d, J=2.4 Hz, 1H), 3.98 (s, 3H), 3.86 (s, 3H), 2.55 (s, 3H).

Step D: Synthesis of Int X-4

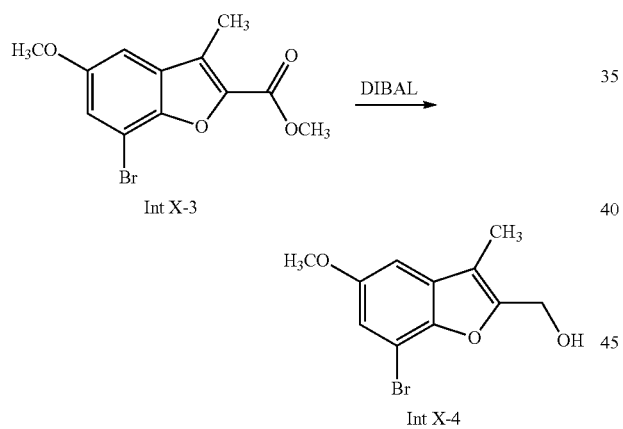

To a mixture of Int X-3 (35 g, 117 mmol) in anhydrous DCM (500 mL) was added a solution of DIBAL-H (257 mL, 1 M in toluene, 257 mmol) dropwise over 1 h at −70° C. under N$_2$ (dry ice-acetone bath). The temperature of the system rose to −65° C. during the addition and the mixture was stirred for 2 h at −70° C. The mixture was warmed to 0° C. and quenched with water (100 mL) and the mixture was filtered. The organic phase was separated and the aqueous phase was extracted with DCM (2×100 mL). The combined organic phase was washed with saturated brine (2×100 mL), dried over anhydrous Na$_2$SO$_4$ and then filtered. The filtrate was concentrated in vacuo and the residue was purified by silica gel chromatography (column height: 30 cm, diameter: 15 cm, 100-200 mesh silica gel, Pet Ether/EtOAc=10/1 to 3/1) to afford Int X-4 (9.8 g) as yellow solid. $^1$H NMR (400 MHz, CDCl$_3$): δ 7.08 (d, J=2.4 Hz, 1H), 6.88 (d, J=2.0 Hz, 1H), 4.76 (s, 2H), 3.85 (s, 3H), 2.23 (s, 3H).

Step E: Synthesis of Compound X

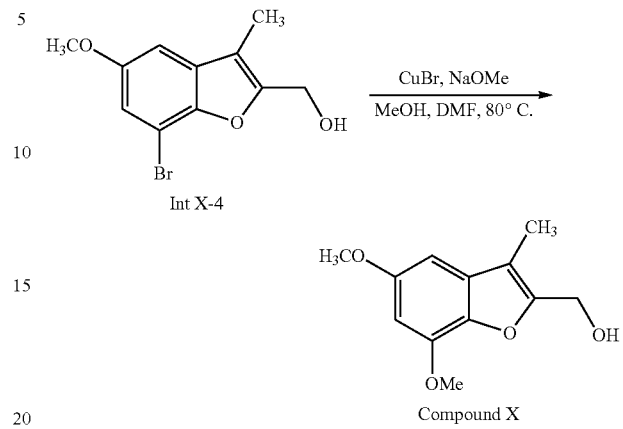

To a mixture of Int X-4 (19.5 g, 71.9 mmol), NaOMe (212 mL, 25% w/v in MeOH) and anhydrous DMF (2.2 g, 29.6 mmol) was added CuBr (3.0 g, 21.2 mmol) at room temperature under nitrogen. The reaction mixture was heated to 80° C.-90° C. for 3 h. The reaction mixture was cooled to 0° C. before H$_2$O (500 mL) was added. The mixture was extracted with DCM (2×300 mL) and the combined organic extracts were dried over anhydrous Na$_2$SO$_4$ and filtered. The filtrate was concentrated in vacuo with rotary-evaporator and the residue was purified by silica gel chromatography (column height: 30 cm, diameter: 10 cm, 100-200 mesh silica gel, petroleum ether/EtOAc=10/1 to 3/1) to afford Compound X (8.4 g) as a yellow solid. $^1$H NMR (400 MHz, CDCl$_3$): δ 6.52 (s, 1H), 6.47 (s, 1H), 4.75 (s, 2H), 3.98 (s, 2H), 3.87 (s, 3H), 2.24 (s, 3H), 1.91 (s, 1H). $^{13}$C NMR: (CDCl$_3$, 100 MHz): δ 156.5, 152.1, 145.3, 138.5, 113.4, 97.1, 93.1, 55.9, 55.8, 55.7, 8.0. LCMS: MS cal.: 222.24; MS found: 205.1 [M−OH]$^+$. Melting point: 71.9° C.-73.8° C.

Compound Y:
1-(5,7-dimethoxybenzofuran-2-yl)ethan-1-ol

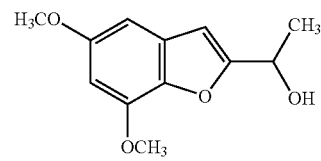 [SMILES: COc1cc(OC)c2oc(C(C)O)cc2c1]

Step A: Synthesis of Int Y-1

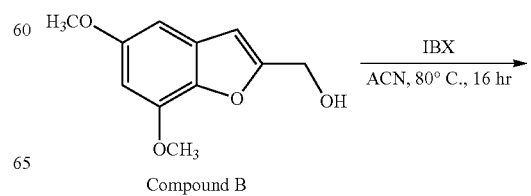
Compound B

Step A: Synthesis of Int Z-1

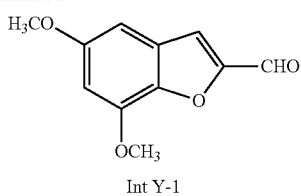

Int Y-1

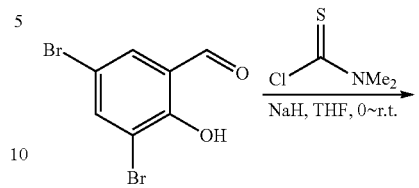

A solution of Compound B (10.0 g, 48.03 mmol) and IBX (26.9 g, 96.06 mmol) was dissolved in 150 mL of acetonitrile and stirred at 80° C. under a blanket of nitrogen for 4 h. The suspension was cooled and filtered and filtered cake was washed with 100 mL of EtOAc. The filtrate was concentrated to give 9.8 g of Int Y-1 as a yellow solid.

Step B: Synthesis of Compound Y

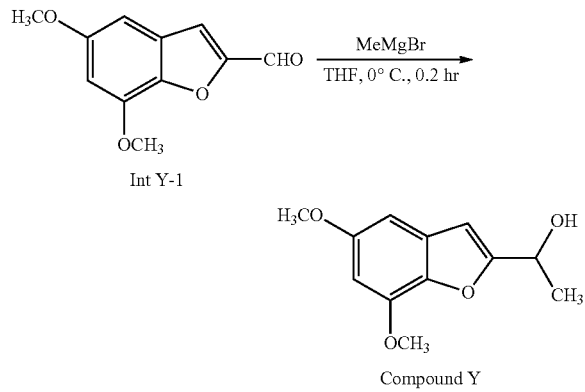

To a 0° C. solution containing 3,5-dibromo-2-hydroxybenzaldehyde (12 g, 42.8 mmol) in THF (100 mL) was added NaH (1.9 g, 47.6 mmol) in five portions. The reaction was stirred for 1 h from 0° C. to 20° C. then recooled and treated with a solution of dimethylthiocarbamoyl chloride (6.52 g, 52.7 mmol) in THF (20 mL). When the reaction was complete, a solution of saturated aqueous $NH_4Cl$ (100 mL) was added and the resulting mixture was extracted with EtOAc (100 mL×2). The organic extracts were dried over anhydrous $Na_2SO_4$, filtered and concentrated. The residue was purified by column chromatography (petroleum ether:EtOAc=50:1~20:1) to afford 9.0 g of Int Z-1 as yellow solid. $^1$H NMR: (400 MHz, $CDCl_3$) δ 9.87 (s, 1H), 7.91 (t, J=8.0 Hz, 2H), 3.40 (s, 6H).

A solution containing 3.0 g (14.5 mmol) in 50 mL of THF at 0° C. was added MeMgBr (7.3 mL, 21.9 mmol, 3M in ether) dropwise at 0° C. The reaction mixture was stirred for 10 minutes before it was quenched with a saturated $NH_4Cl$ solution (20 mL). The resulting organic layer was extracted with EtOAc (100 mL×2) and the combined organic extracts were dried over $Na_2SO_4$, filtered and concentrated to give 3.2 g of Compound Y as a brown oil. $^1$H NMR (400 MHz, $CDCl_3$) δ 6.50 (s, 1H), 6.47 (s, 1H), 6.35 (s, 1H), 4.93 (dd, J=6.0, 12.8 Hz, 1H), 3.89 (s, 3H), 3.75 (s, 3H), 1.55 (d, J=6.0, 12.8 Hz, 3H).

Step B: Synthesis of Int Z-2

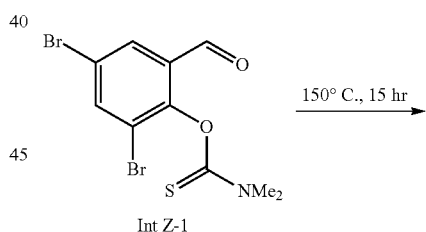

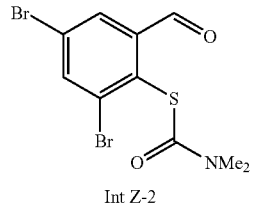

Int Z-2

Compound Z: (5,7-dimethoxybenzo[b]thiophen-2-yl)methanol

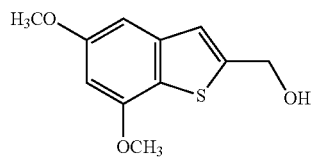 [SMILES: COc1cc(OC)c2sc(CO)cc2c1]

Compound Int Z-1 (5.0 g, 13.6 mmol) in a 100 mL round bottom flask was stirred at 150° C. for 3 hr then cooled and purified by column chromatography (petroleum ether:EtOAc=5:1) to afford 3 g of Int Z-2 as yellow solid. $^1$H NMR (400 MHz, $CDCl_3$) δ 10.18 (s, 1H), 8.00 (t, J=10.0 Hz, 2H), 3.14 (s, 3H), 2.97 (s, 3H).

Step C: Synthesis of Int Z-3

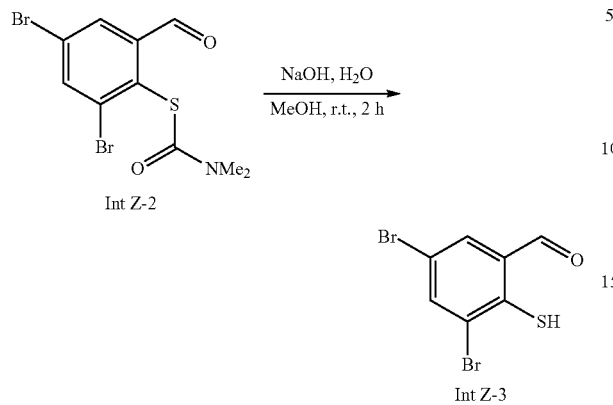

A solution containing 3 g (8.17 mmol) of Int Z-2 in MeOH (50 mL) was added NaOH (1.8 g, 45 mmol) in H$_2$O (50 mL). The reaction was stirred at ambient temperature for 2 h. The reaction was neutralized by the addition of 10% citric acid (50 mL) and extracted with EtOAc (50 mL×2). The organic extracts were dried over anhydrous Na$_2$SO$_4$, filtered and concentrated to provide Int Z-3 (2 g, crude) as yellow oil which was used in the next step without further purification.

Step D: Synthesis of Int Z-4

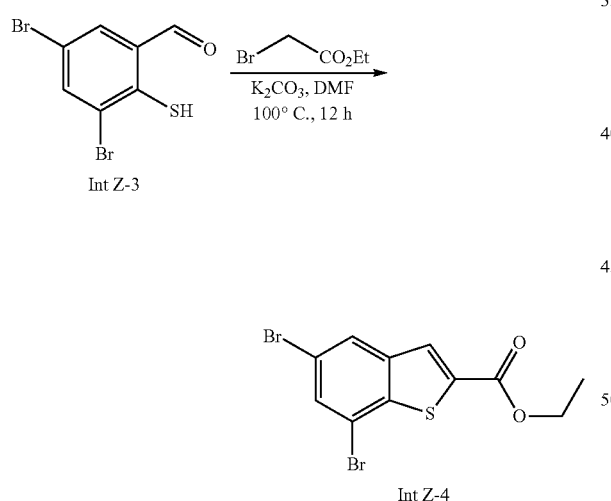

A solution containing 2 g (6.76 mmol) of Int Z-3 in DMF (80 mL) was added ethyl bromoacetate (1.13 g, 6.76 mmol) and K$_2$CO$_3$ (2.8 g, 20.3 mmol). The resulting mixture was heated to 100° C. and stirred for 12 h. The reaction was then cooled and treated with 100 mL of water then extracted with 2×100 mL of EtOAc. The organic extracts were dried and concentrated to afford a residue which was purified by column chromatography (petroleum ether:EtOAc=100:1) to provide Int Z-4 (2.0 g) as a white solid. $^1$H NMR (400 MHz, CDCl$_3$) δ 7.98 (s, 1H), 7.90 (d, J=2.0 Hz, 1H), 7.66 (d, J=2.0 Hz, 1H), 4.36-4.34 (m, 2H), 1.37-1.33 (m, 3H).

Step E: Synthesis of Int Z-5

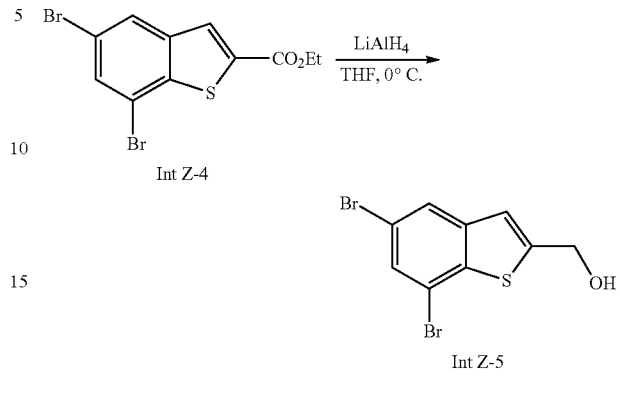

To a slurry containing LiAlH$_4$ (0.42 g, 11 mmol) in THF (80 mL) in a 250 mL round bottom flask at 0° C. was added a solution of Int Z-4 (2 g, 5.5 mmol) in THF (20 mL) dropwise at 0° C. The reaction mixture was stirred at 0° C. for 1 h then quenched slowly with H$_2$O (0.45 mL) then NaOH (15%, 0.45 mL) and H$_2$O (1.3 mL). Solid MgSO$_4$ was added and the mixture was filtered. The filtrate was concentrated to afford Int Z-5 (1.4 g) as white solid.

Step F: Synthesis of Int Z-6

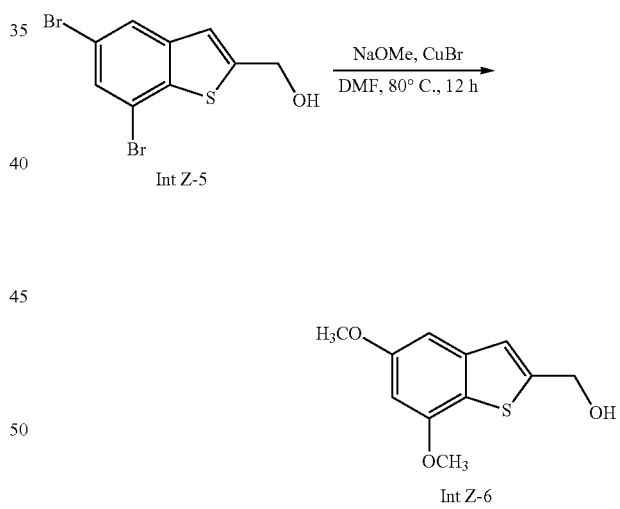

A solution containing Int Z-5 (1.4 g, 4.35 mmol) in NaOMe/MeOH (40 mL) was added DMF (0.13 g, 1.74 mmol) and CuBr (0.19 g, 1.31 mmol). The resulting mixture was stirred for 12 h at 100° C. then cooled and treated with 50 mL of water. The mixture was extracted with 50 mL of DCM then dried over anhydrous Na$_2$SO$_4$. The mixture was filtered and concentrated to leave a residue which was purified by column chromatography (Petroleum Ether/EtOAc=20:1) to provide 1.1 g of Compound Z as a white solid. $^1$H NMR (400 MHz, CDCl$_3$) δ 7.11 (s, 1H), 6.73 (d, J=2.0 Hz, 1H), 6.36 (d, J=2.0 Hz, 1H), 4.83 (t, J=4.8 Hz, 1H), 3.87 (s, 3H), 3.79 (s, 3H).

EXAMPLES

Example 1

Preparation of ((2R,3R,5R)-5-(4-((((5,7-dimethoxy-benzofuran-2-yl)methoxy)carbonyl)-amino)-2-oxopyrimidin-1(2H)-yl)-4,4-difluoro-3-hydroxytetrahydrofuran-2-yl)methyl hydrogen phosphate triethyl ammonium salt (Compound 1)

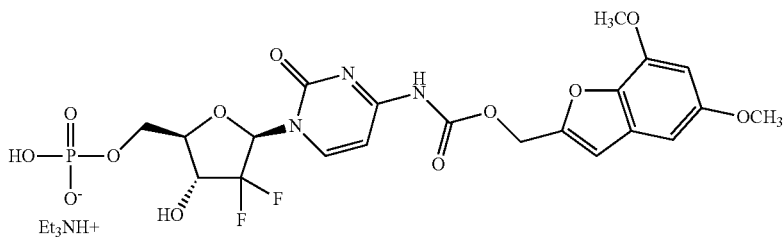 [SMILES: "Et3NH+" ; COc1cc(OC)c2oc(COC(=O)Nc3ccn([C@@H]4O[C@H](COP(=O)([O-])O)[C@@H](O)C4(F)F)c(=O)n3)cc2c1]

Step A: Synthesis of Int 1-1

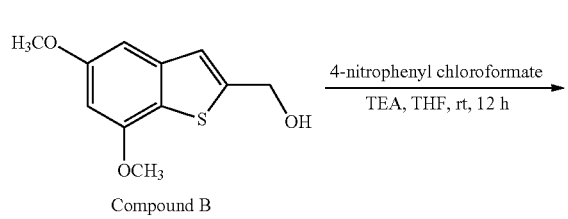

Step B: Synthesis of Int 1-2

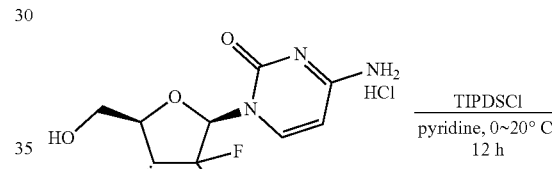

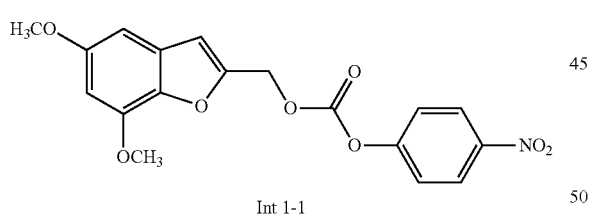

To a stirred solution of compound B (60 g, 0.29 mol) and TEA (31 g, 0.30 mol) in anhydrous THF (500 mL) (ice-water bath) was added 4-nitrophenyl chloroformate (60 g, 0.30 mol) in anhydrous THF (300 mL) dropwise at 0° C. The reaction mixture was then stirred at 20° C. for 12 h before the solvent was evaporated. The crude residue was washed with MTBE (150 mL×3) and then filtered. The filtrate was discarded and the filter cake was dissolved in EtOAc (2000 mL) and water (1000 mL). The organic phase was separated and washed with water (1000 mL×2) then brine (500 mL) then dried over anhydrous $Na_2SO_4$. The filtrate was concentrated to afford 85 g of Int 1-1. $R_f$(PE:EtOAc=3:1)=0.5. $^1$H NMR (400 MHz) CDCl$_3$ δ 8.30 (d, J=9.2 Hz, 2H), 7.40 (d, J=9.2 Hz, 2H), 6.84 (s, 1H), 6.62 (s, 1H), 6.51 (s, 1H), 5.38 (s, 2H), 4.00 (s, 3H), 3.84 (s, 3H).

To a solution of gemcitabine hydrochloride (140 g, 460 mmol) in pyridine (2000 mL) (ice-water bath) was added TIPDSCl (176 g, 560 mmol) dropwise at 0° C. under $N_2$. The reaction mixture was stirred at 20° C. for 12 h. The pyridine removed under vacuum and the residue was dissolved with EtOAc (1500 mL) and washed with water (800 mL×3). The organic layer was separated and dried over anhydrous $Na_2SO_4$ and filtered. The filtrate was concentrated to give 250 g of compound 1-2 as white solid, which was used directly to the next step. $^1$H NMR (400 MHz) DMSO-d$^6$ δ 7.49 (d, J=7.6 Hz, 1H), 7.41-7.44 (m, 2H), 6.11 (s, 1H), 5.78-5.80 (m, 1H), 4.37 (s, 1H), 4.12-4.20 (d, J=10.4 Hz, 1H), 4.00-3.89 (m, 2H), 1.05-0.73 (m, 28H).

Step C: Synthesis of Int i-3

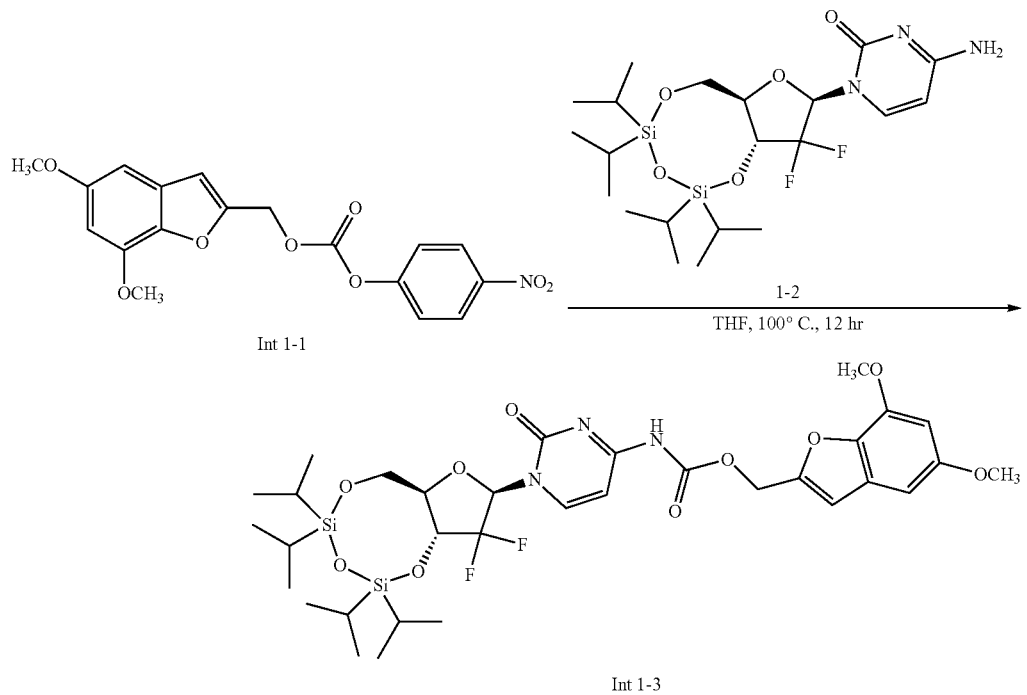

Int 1-1

To a stirred suspension of compound Int 1-1 (85 g, 0.224 mol) in THF (800 mL) was added compound 1-2 (116 g, 0.23 mol) in one portion under nitrogen. The resulting solution was heated to reflux at 100° C. for 12 h. The mixture was cooled and the solvent was evaporated off to give a residue which was dissolved in EtOAc (500 mL) and washed with water (200 mL×3). The organic phase was separated and dried over anhydrous $Na_2SO_4$ and filtered. The filtrate was concentrated under reduced pressure to afford the crude product which was purified by flash chromatography to give 90 g of compound Int 1-3 as foam. $R_f$ (Petroleum Ether:EtOAc=1:1)=0.4.

Step D: Synthesis of Int 1-4

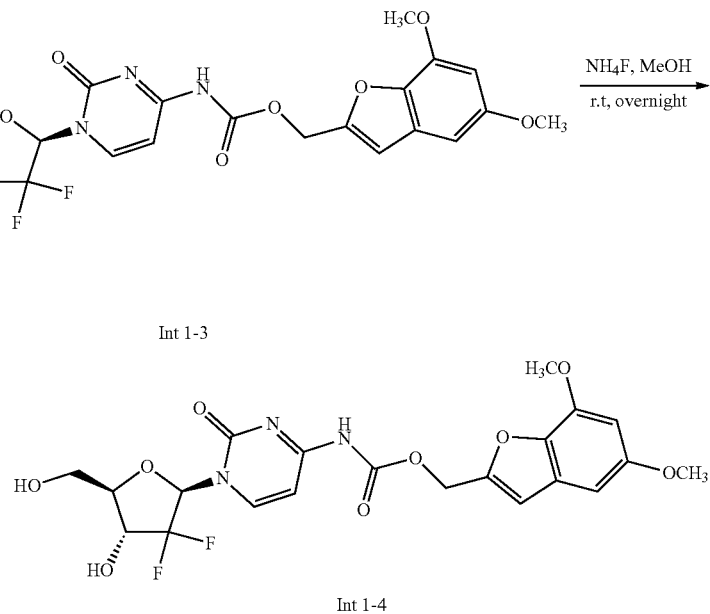

Compound Int 1-3 (90 g, 0.12 mol) was dissolved in MeOH (1000 mL) and treated with NH$_4$F (22.5 g, 2.46 mol) in a single portion. The resulting solution was stirred at 20° C. for 12 h before the solvent was evaporated affording a residue. The residue was dissolved in EtOAc (1000 mL) and washed with water (500 mL×3) then dried over anhydrous Na$_2$SO$_4$ and concentrated to give a residue. The residue was covered with HPLC grade MeOH (1000 mL) then filtered. The filter cake was washed with HPLC grade MeOH (200 mL×2). The filter cake was then covered with HPLC grade MeOH (1500 mL) and heated at 80° C. to produce a solution. The solution was cooled to room temperature over 12 h to effect precipitation. The precipitate was filtered and washed with HPLC grade MeOH (150 mL×3) and the solids were dried at 45° C. for 6 days to give 35 g of Int 1-4 as a white solid. R$_f$ (DCM/MeOH=15/1)=0.3. HPLC: t=2.40 min; purity: 99.71%. $^1$H NMR (400 MHz) DMSO-d$^6$ δ 11.03 (s, 1H), 8.24 (d, J=7.6 Hz, 1H), 7.10 (d, J=7.2 Hz, 1H), 6.95 (s, 1H), 6.72 (s, 1H), 6.56 (s, 1H), 6.31 (d, J=2.0 Hz, 1H), 6.18-6.14 (m, 1H), 5.30 (s, 3H), 4.21-3.90 (m, 1H), 3.82 (s, 4H), 3.77 (m, 4H), 3.69-3.64 (m, 1H). MS cal.: 497.1, [M−44]$^+$=454.2.

Step E: Synthesis of Compound 1

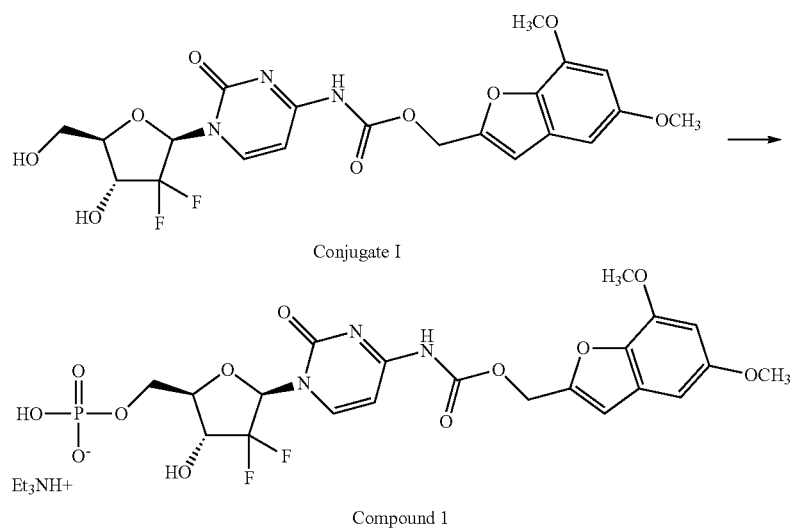

To a dry 100 mL round bottomed flask containing Int 1-4 (2.0 g, 4.0 mmol) was added trimethyl phosphate (10 ml). The slurry was stirred under nitrogen at room temperature until a homogeneous solution formed. The resulting reaction mixture was then cooled to −10° C. in an ice-water-salt bath and stirred for 10 minutes. Phosphorous oxychloride (2.8 g, 18 mmol) was added in a dropwise fashion over a period of 10 minutes. Upon completion of addition, the reaction mixture was stirred at −10° C. for an additional 3 hours. The reaction mixture was then treated with deionized water (200 mL) drop wise at 0° C. During the addition, a yellow solid was formed which was subsequently filtered and washed with water (10 mL×3). The yellow solid was dissolved in acetonitrile/water (20 mL, 1/1) and adjusted to pH=8 with EtOAc. The mixture was purified by preparative HPLC to give 1.0 g of Compound 1 as a white solid. HPLC purity: 99.83%. $^1$H NMR (400 MHz) DMSO-d$^6$ δ 11.03 (br. s., 1H), 8.32 (d, J=7.5 Hz, 1H), 7.11 (d, J=7.5 Hz, 1H), 6.96 (s, 1H), 6.72 (s, 1H), 6.56 (d, J=1.5 Hz, 1H), 6.16 (t, J=6.9 Hz, 1H), 5.30 (s, 2H), 4.31-4.22 (m, 1H), 4.08 (s., 1H), 3.99 (d, J=6.3 Hz, 2H), 3.90 (s, 3H), 3.77 (s, 3H), 2.97 (d, J=6.5 Hz, 6H), 1.16 (t, J=7.2 Hz, 9H). $^{31}$P NMR: (160 MHz) DMSO-d$^6$ δ 0.27.

Example 2

Preparation of Disodium ((2R,3R,5R)-5-(4-((((5,7-dimethoxybenzofuran-2-yl)methoxy)-carbonyl)amino)-2-oxopyrimidin-1(2H)-yl)-4,4-difluoro-3-hydroxytetra-hydrofuran-2-yl)-methyl phosphate (Compound 2)

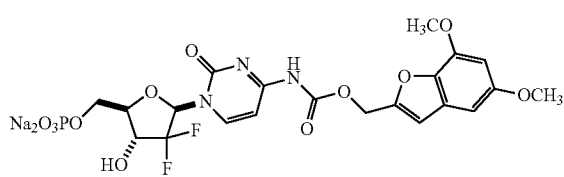

Step A: Preparation of Compound 2

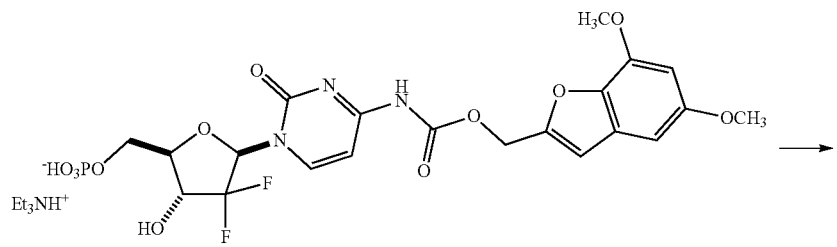

Compound 1 (0.100 g, 0.1 mmoles, 1.0 equivalent) was dissolved in deionized water (10 mL) and added to Bio-Rex 70 sodium form ion-exchange resin (5.0 g) which was previously swelled with deionized water (10 mL). The mixture was diluted with deionized water (20 mL) and stirred at room temperature for 1 hour. HPLC and LC_MS indicated a complete different retention time from the starting material. The material was filtered through a sintered frit. The resulting clear solution was lyophilized to dryness to obtain Compound 2 as a white powder. $^1$H NMR (300 MHz, D$_2$O): δ 8.16 (d, J=7.5 Hz, 1H), 7.02 (d, J=7.8 Hz, 1H), 6.72 (s, 1H), 6.56 (d, J=1.8 Hz, 1H), 6.35 (d, J=2.1 Hz, 1H), 6.06 (t, J=6.8 Hz, 1H), 5.17-5.08 (m, 2H), 4.40-4.28 (m, 1H), 4.06-4.00 (m, 2H), 3.95-3.86 (m, 1H), 3.78 (s, 3H), 3.65 (s, 3H). $^{31}$P NMR (120 MHz, D$_2$O): δ 4.90

Example 3

Preparation of Triethylammonium ((2R,3R,5R)-5-(4-((((5,7-bis(methoxy-d3)benzofuran-2-yl)-methoxy)carbonyl)amino)-2-oxopyrimidin-1(2H)-yl)-4,4-difluoro-3-hydroxy-tetrahydrofuran-2-yl) methyl hydrogen phosphate (Compound 3)

Step A: Synthesis of Int 3-1

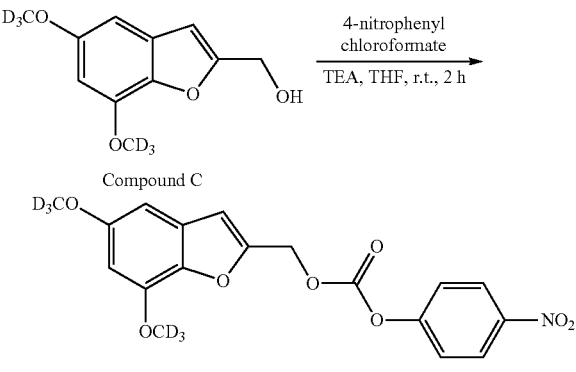

To a stirred solution of Compound C (17 g, 79 mmol) in THF (100 mL) was added EtOAc (8.2 g, 83 mmol) drop wise at 0° C. (ice-water bath) over 5 min followed the solution of 4-nitrophenyl chloroformate (17.1 g, 85 mmol) portionwise in THF (50 mL). The resulting solution was

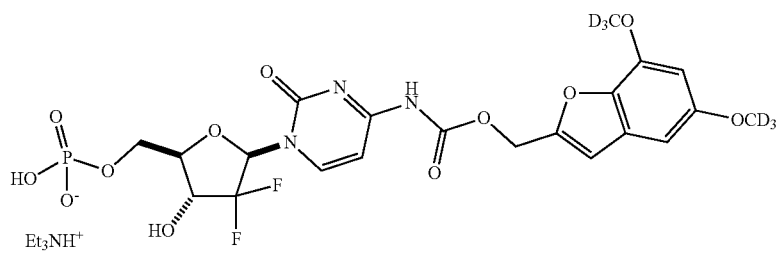

stirred at room temperature for 2 h. The solvent was then evaporated and the crude residue was stirred with MTBE (100 mL×3) then filtered. The filter cake was dissolved in EtOAc (150 mL) and washed with water (50 mL×2). The organic layer was separated, dried over anhydrous Na$_2$SO$_4$ and filtered. The filtrate was concentrated to give Int 3-9 (19 g) as a white solid. LCMS: 380.2 [M+H]$^+$. $^1$H NMR: (CDCl$_3$, 400 MHz): δ 8.27 (d, J=8.8 Hz, 2H), 7.38 (d, J=8.8 Hz, 2H), 6.83 (s, 1H), 6.60 (d, J=2.0 Hz, 1H), 6.49 (s, J=2.0 Hz, 1H), 5.37 (s, 2H).

Step B: Synthesis of Int 3-2

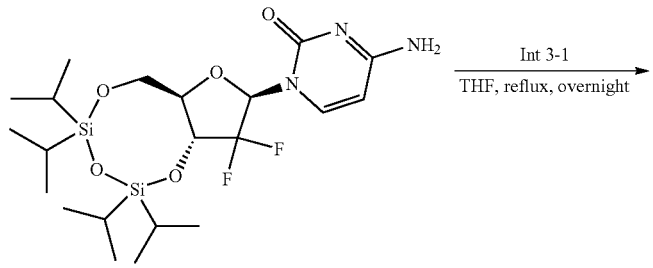

To a stirred solution of Int 1-2 (14 g, 28 mmol) in THF (50 mL) was added Int 3-9 (11 g, 28 mmol) and the resulting solution was heated to reflux overnight. The mixture was cooled to room temperature and the solvent was removed to give a residue. The residue was purified by flash chromatography (column height: 30 cm, diameter: 10 cm, 100-200 mesh silica gel, petroleum ether/EtOAc=10/1, 5/1, 4/1) to give Int 3-10 (13 g) as white solid. LCMS: 702.4 [M−C$_3$H$_8$]$^+$. $^1$H NMR (400 MHz, CDCl$_3$): δ 8.02 (d, J=8.0, 1H), 7.32 (d, J=8.4, 1H) 6.81 (s, 1H), 6.63 (d, J=2.0 Hz, 1H), 6.47 (d, J=2.0 Hz, 1H), 6.17-6.14 (t, J=12.4 Hz, 1H), 5.33-5.25 (m, 2H), 4.43-4.37 (m, 2H), 4.25-4.21 (m, 1H), 4.10-3.91 (m, 2H), 1.11-1.03 (m, 28H).

Step C: Synthesis of Int 3-3

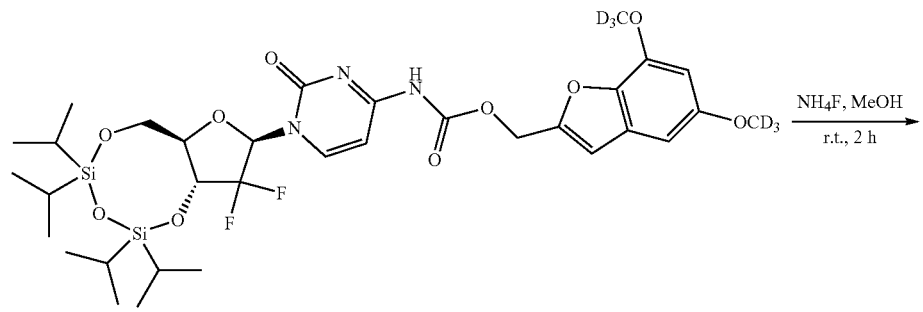

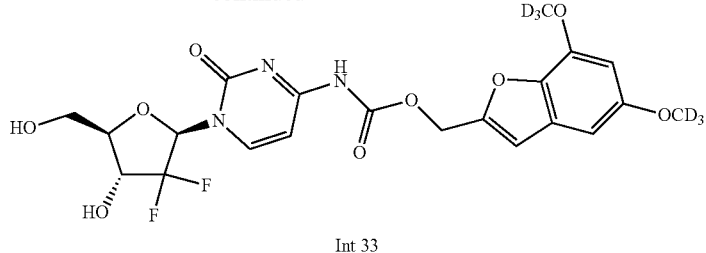

Int 33

Compound Int 3-2 (13 g, 17.4 mmol) was dissolved in MeOH (50 mL). To this solution was added NH₄F (2.9 g, 78.4 mmol) in one portion and the resulting solution was stirred at room temperature overnight. The solvent was evaporated to give a residue which was dissolved in EtOAc (100 mL) then washed with water (50 mL×3). The organic extracts were combined and dried over anhydrous Na₂SO₄ then concentrated to give a residue. The residue was stirred with HPLC grade MeOH (200 mL) then filtered. The filter cake was washed twice with 500 mL of HPLC grade MeOH (HPLC showed the purity of the filter cake to be ~99%). The filter cake was dissolved in HPLC grade MeOH (200 mL) and heated to 80° C. The heat was removed and the resulting solution was allowed to stand at room temperature overnight. The resulting solid was filtered and washed with HPLC grade MeOH (50 mL×3). The solid product was heated at 45° C. under vacuum for 6 days, to give Int 3-3 (5.7 g) as white solid. LCMS: 460 [M−CO₂]⁺. ¹H NMR: (DMSO-d⁶, 400 MHz): δ=10.01 (s, 1H), 8.24 (d, J=8.0 Hz, 1H), 7.10 (d, J=7.6 Hz, 1H), 6.94 (s, 1H), 6.71 (s, 1H), 6.55 (d, J=2.0 Hz, 1H), 6.32-6.30 (m, 1H), 6.18-6.14 (m, 1H), 5.29 (s, 3H), 4.22-4.16 (m, 1H), 3.89-3.87 (m, 1H), 3.78-3.65 (m, 2H). ¹³C NMR: (DMSO-d⁶, 100 MHz): a: 163.7, 157.0, 154.4, 153.1, 152.5, 145.5, 144.9, 139.4, 129.2, 125.9, 123.4, 120.8, 108.5, 98.0, 95.3, 81.4, 69.0, 68.8, 68.6, 59.7, 59.2. MP: 137.8° C.-142.4° C.

Step D: Synthesis of Compound 3

A dry 100 mL round bottomed flask, was charged with Int 3-3 (0.223 g, 0.4 mmol, 1.0 equivalent) and trimethyl phosphate (0.918 ml). This mixture was sonicated to give a homogenous solution which was then cooled in an ice-water bath and stirred for 10 minutes. Phosphorous oxychloride (49 ul, 0.5 mmoles, 1.2 equivalents) was added in a dropwise fashion over a period of 3 min. The stirred reaction mixture was allowed to warm to room temperature and stirred for 2 hours. Additional phosphorous oxychloride (13 ul) was added and stirred for an hour. The reaction was quenched with 2 M TEAHC buffer (triethylammonium hydrogen carbonate) until pH=8 and stored in the fridge over the weekend. The mixture was then extracted with dichloromethane (50 ml). The aqueous layer was purified by preparative reverse phase-HPLC (Gemini-NX, 10u C18 110A AXD 100×21.20 mm; 0-50% CH₃CN/50 mM TEAHC water over 9 min, held at 50% CH₃CN/50 mM TEAHC water for 10 min, there were about 6 mL of the crude product, injection amount was 0.4 mL, the product was eluted at ~5.5 min). The collected fractions were lyophilized to give 140 mg of compound 3 as a white solid. ¹H NMR (D₂O, 300 MHz): δ 8.2 ppm (d, 1H, J=7.5 Hz), 7.05 (d, 1H, J=7.5 Hz), 6.79 (s, 1H), 6.65 (d, 1H, 2.4 Hz), 6.455 (d, 1H, J=2.4 Hz), 6.131 (m, 1H), 5.195 (s, 2H), 4.5-4.3 (m, 1H), 4.15-4.0 (m, 2H), 4.0-3.9 (m, 1H), 3.0 (q, 12H, J=7.2 Hz, Et₃NH⁺), 1.141 (t, 18H, J=7.2 Hz, Et₃NH⁺). ³¹P NMR (D₂O, 121 MHz): δ 4.975. LC-MS: 606.0 [M+Na]⁺, 581.6 [M−1]⁻.

The following compounds 4-6 can be prepared using a similar procedure to that described in Example 3:

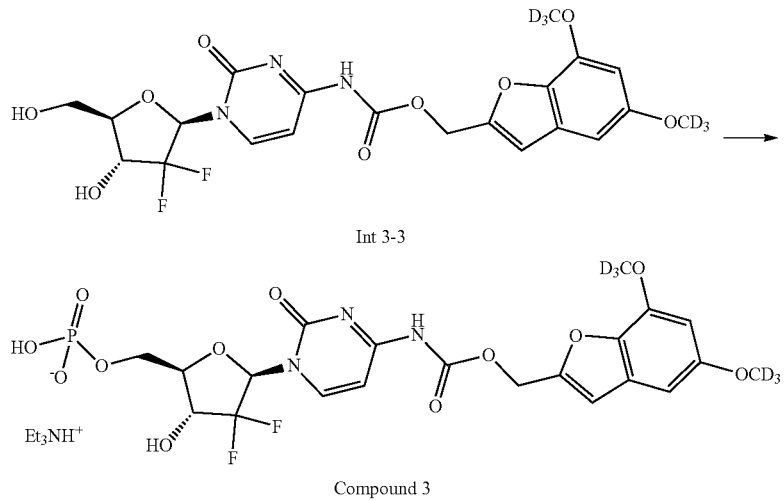

Int 3-3

Compound 3

Compound 4: Triethylammonium ((2R,3R,5R)-5-(4-((((5,7-dibromobenzofuran-2-yl)methoxy)carbonyl)-amino)-2-oxopyrimidin-1(2H)-yl)-4,4-difluoro-3-hydroxytetra-hydrofuran-2-yl)methyl hydrogen phosphate

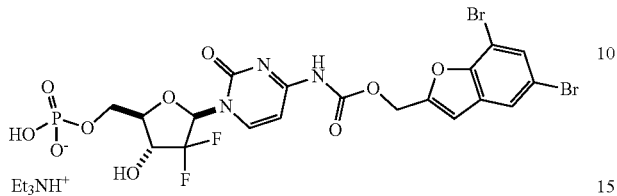

$^1$H NMR (300 MHz, D$_2$O): δ 7.94 (d, J=7.2 Hz, 1H), 7.09 (s, 1H), 6.98 (s, 1H), 6.94 (d, J=7.2 Hz, 1H), 6.54 (s, 1H), 6.01 (t, J=7.2 Hz, 1H), 5.11-5.00 (m, 2H), 4.30-4.19 (m, 1H), 4.09-4.02 (m, 3H), 3.00 (q, J=7.2 Hz, 6H), 1.08 (t, J=7.2 Hz, 9H). $^{31}$P NMR (121 MHz, D$_2$O): δ 1.92. LC-MS: 1350.4 [2M+1]$^+$, 675.7, 677.6, 678.7 [M+1]$^+$

Compound 5: Triethylammonium ((2R,3R,5R)-4,4-difluoro-3-hydroxy-5-(4-(((((5-methoxy-7-methyl-benzofuran-2-yl)methoxy)carbonyl)amino)-2-oxopyrimidin-1(2H)-yl)tetrahydrofuran-2-yl)methyl hydrogen phosphate

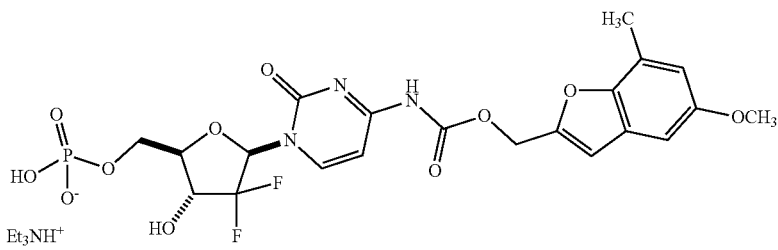 [SMILES: "Et3NH+" ; COc1cc(C)c2oc(COC(=O)Nc3ccn([C@@H]4O[C@H](COP(=O)([O-])O)[C@@H](O)C4(F)F)c(=O)n3)cc2c1]

$^1$H NMR (300 MHz, D$_2$O): δ 7.94 (d, J=7.5 Hz, 1H), 6.77 (d, J=7.5 Hz, 1H), 6.60 (d, J=2.1 Hz, 1H), 6.56 (s, 1H), 6.40 (s, 1H), 5.96 (t, J=7.0 Hz, 1H), 5.02-4.91 (m, 2H), 4.33-4.21 (m, 1H), 4.01-3.97 (m, 2H), 3.92-3.86 (m, 1H), 3.54 (s, 3H), 2.87 (q, J=7.3 Hz, 12H), 2.12 (s, 3H), 1.02 (t, J=7.3 Hz, 18H). $^{31}$P NMR (121 MHz, D$_2$O): δ 4.88.

Compound 6: Triethylammonium ((2R,3R,5R)-5-(4-((((5,7-dimethylbenzofuran-2-yl)methoxy)carbonyl)amino)-2-oxopyrimidin-1(2H)-yl)-4,4-difluoro-3-hydroxytetra-hydrofuran-2-yl)methyl hydrogen phosphate

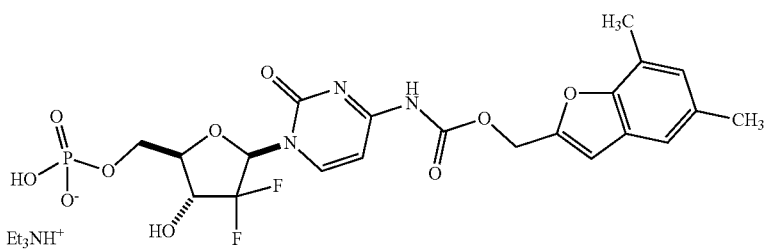 [SMILES: "Et3NH+" ; Cc1cc(C)c2oc(COC(=O)Nc3ccn([C@@H]4O[C@H](COP(=O)([O-])O)[C@@H](O)C4(F)F)c(=O)n3)cc2c1]

$^1$H NMR (300 MHz, D$_2$O): δ 8.04 (d, J=7.5 Hz, 1H), 6.99-6.89 (m, 3H), 6.56 (s, 1H), 6.00 (t, J=6.9 Hz, 1H), 5.11-5.00 (m, 2H), 4.35-4.24 (m, 1H), 4.04-3.88 (m, 3H), 2.95 (q, J=7.2 Hz, 12H), 1.98 (s, 3H), 1.96 (s, 3H), 1.07 (t, J=7.2 Hz, 18H). $^{31}$P NMR (121 MHz, D$_2$O): δ 4.90. LC-MS: 543.6 [M−H]$^+$.

Example 4

Preparation of di(triethylammonium) ((2R,3R,5R)-5-(4-((((4-((5,7-dimethoxybenzofuran-2-yl)methoxy)benzyl)oxy)carbonyl)amino)-2-oxopyrimidin-1(2H)-yl)-4,4-difluoro-3-hydroxytetrahydrofuran-2-yl) methyl phosphate (Compound 7)

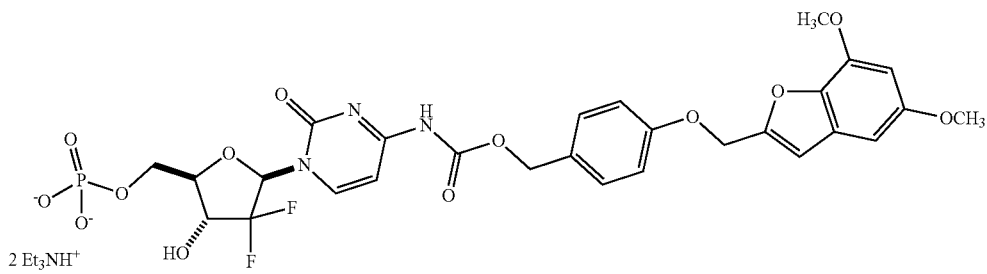

Step A: Preparation of Compound 7

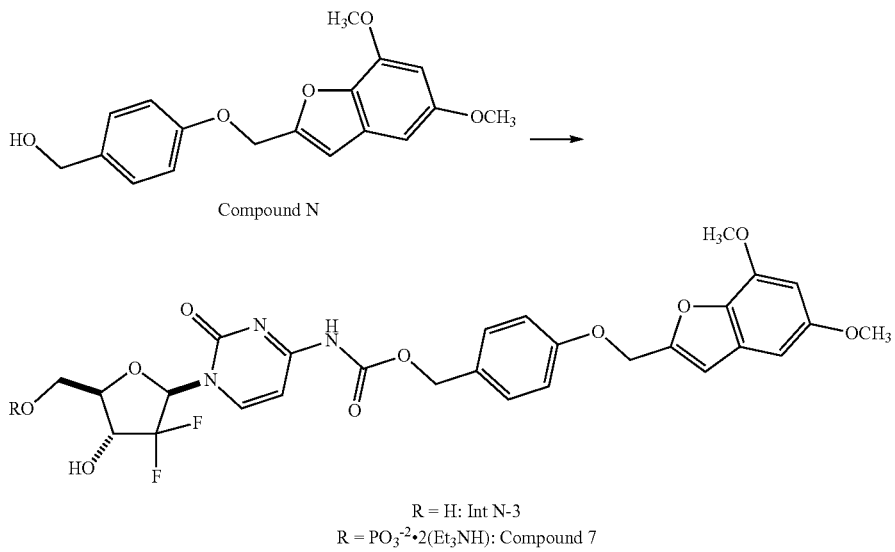

R = H: Int N-3
R = PO$_3$$^{-2}$·2(Et$_3$NH): Compound 7

Int N was converted to Int N-3 using the 3 step procedure described in Example 1. A dry 100 mL round bottomed flask was charged with Int N-3 (0.220 g, 0.4 mmol) and trimethyl phosphate (0.906 ml). This mixture was sonicated to give a homogenous solution after which was cooled in an ice-water bath and stirred for 10 minutes. Phosphorous oxychloride (40 uL, 0.4 mmol) was added in a dropwise fashion over 3 minutes. Upon completion of addition the reaction mixture was allowed to warm to room temperature and stirred for 2 h. Additional phosphorous oxychloride (13 ul) was added and the reaction mixture was stirred for an hour. The reaction was quenched with 2 M TEAHC buffer until pH=8 and stirred overnight at room temperature. The mixture was then extracted with dichloromethane. The aqueous layer (initially an emulsion, which was cleared upon standing overnight standing) was purified on preparative reverse phase-HPLC (Gemini-NX, 10u C18 110A AXD 100×21.20 mm; 0-45% CH$_3$CN/50 mM TEAHC water over 16 minutes, held at 45% CH$_3$CN/50 mM TEAHC water for 2 minutes, the product was eluted at 12 minutes). Appropriate fractions were collected, combined and lyophilized to afford Compound 7 as a white powder (87 mg). $^1$H NMR (300 MHz, D$_2$O): δ 7.83 (d, J=7.8 Hz, 1H), 7.08 (d, J=7.5 Hz, 1H), 6.69-6.63 (m, 3H), 6.10 (s, 1H), 5.97 (t, J=7.3 Hz, 1H), 5.85 (s, 1H), 5.50 (s, 1H), 4.82 (s, 2H), 4.75 (s, 2H), 4.31-4.20 (m, 1H), 4.04-3.89 (m, 3H), 3.51 (s, 3H), 3.28 (s, 3H), 2.85 (q, J=7.3 Hz, 12H), 1.04 (t, J=7.3 Hz, 18H). $^{31}$P NMR (121 MHz, D$_2$O): δ 4.95. LCMS: 639.9 [M−44+H]$^+$ The following compound could be prepared using a similar procedure to that described in Example 4:

Compound 8: Di(triethylammonium) ((2R,3R,5R)-5-(4-((((4-((5-methoxy-7-methylbenzofuran-2-yl)methoxy)benzyl)oxy)carbonyl)amino)-2-oxopyrimidin-1(2H)-yl)-4,4-difluoro-3-hydroxytetrahydrofuran-2-yl)methyl phosphate

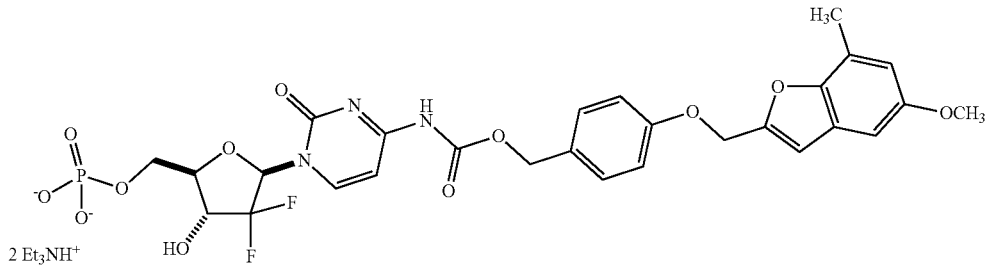

Yield: 55%. $^1$H NMR (300 MHz, D$_2$O): δ 7.86 (d, J=7.8 Hz, 1H), 6.92 (d, J=7.8 Hz, 2H), 6.79 (d, J=7.8 Hz, 1H), 6.48 (d, J=7.8 Hz, 2H), 6.20-6.11 (m, 3H), 5.99 (t, J=7.3 Hz, 1H), 4.71 (s, 2H), 4.48 (s, 2H), 4.29-4.18 (m, 1H), 4.02-3.88 (m, 3H), 3.31 (s, 3H), 2.80 (q, J=7.3 Hz, 12H), 1.00 (t, J=7.3 Hz, 18H). $^{31}$P NMR (121 MHz, D$_2$O): δ 4.91. LC-MS: 624.0 [M−CO$_2$+H]$^+$; 690.0[M+Na]$^+$ Example 5

Comparative Cytotoxicity IC$_{50}$ of Compound 1 with its Non-Phosphorylated SMDC Int 1-4 and Gemcitabine in Primary Human Head and Neck Squamous Cell Carcinoma Cell Lines A tumor cell proliferation assay was used to determine cytotoxicity IC$_{50}$ values for the phosphate prodrug Compounds 1-9, the parent non-phosphorylated SMDC parent compounds, and the effector (gemcitabine) across eight primary early-passage human head and neck squamous cell carcinoma cell lines including UT-SCC-5, UT-SCC-8, UT-SCC-9, UT-SCC-10, UT-SCC-14, UT-SCC-16A, UT-SCC-16B, and UT-SCC-24A.

Methods

UTSCC cells were seeded at 4000 cells/100 I/well on 96-well black clear-bottom tissue culture plate. Cells were incubated at 37° C. and 5% CO$_2$ overnight to allow them to recover and re-attach. The next day cells were treated with the test compound (0-100 µM) for 72 hours. After treatment, cell proliferation was measured by Fluorescent quantitation of alamarBlue reagent. The alamarBlue assay incorporates a fluorometric/colorimetric growth indicator based on detection of metabolic activity. Specifically, resazurin, the active ingredient of alamarBlue reagent, is blue in color and virtually non-fluorescent. Upon entering cells, resazurin is reduced to resorufin, a compound that is red in color and highly fluorescent.

Continued cell growth maintains a reduced environment, therefore increasing the overall fluorescence and color of the media surrounding cells. The fluorescence intensity of alamarBlue reagent was directly proportional to cell number. To perform the alamarBlue assay, 10 I of alamarBlue reagent was added to each well and the plate was incubated at 37° C. for an additional 2 hour. Fluorescence intensity was measured at an excitation of 530 nm and an emission of 590 nm using a BioTek Synergy™ 2 microplate reader.

Cell proliferation assays in triplicate were performed at each concentration. The fluorescent intensity data were analyzed using the computer software, Graphpad Prism. In the absence of the compound, the fluorescent intensity ($F_t$) in each data set was defined as 100%. In the absence of cells, the fluorescent intensity ($F_b$) in each data set was defined as 0%. The percent cell in the presence of each compound was calculated according to the following equation: % cell=(F−$F_b$)/($F_t$−$F_b$), where F=the fluorescent intensity in the presence of the compound, $F_b$=the fluorescent intensity in the absence of cells, and $F_t$=the fluorescent intensity in the absence of the compound. The values of % cell versus a series of compound concentrations were then plotted using non-linear regression analysis of Sigmoidal dose-response curve generated with the equation Y=B+(T−B)/1+10$^{((Log\ EC50-X) \times Hill\ Slope)}$ where Y=percent cell, B=minimum percent cell, T=maximum percent cell, X=logarithm of compound and Hill Slope=slope factor or Hill coefficient. The IC$_{50}$ value was determined by the concentration causing a half-maximal percent activity.

The cytotoxicity IC$_{50}$ values for Compound 1, the non-phosphorylated parent SMDC (Int 1-4) and gemcitabine are displayed in Table 1. The average ratio of cytotoxicity IC$_{50}$ values for Compound 1/Int 1-4~1 is consistent with Compound 1 acting as a prodrug of Int 1-4. The average ratio of cytotoxicity IC$_{50}$ values for Compound 1/gemcitabine~1.6 indicates that

TABLE 1

Cytotoxicity of Compound 1 (phospate prodrug) compared to Intermediate 1-4 (parent SMDC) and gemcitabine (effector) in a series of primary head and neck squamous cell carcinoma cell lines.

| Tumor cell lines* | Cytotoxicity IC$_{50}$/uM | | | | |
|---|---|---|---|---|---|
| | Cmpd 1 | Int 1-4 | gemcitabine | Compound 1/ Int 1-4 | Compound 1/ gemcitabine |
| UT-SCC-5 | 0.024 | 0.016 | 0.009 | 1.5 | 2.7 |
| UT-SCC-8 | 0.023 | 0.032 | 0.022 | 0.7 | 1.0 |
| UT-SCC-9 | 0.053 | 0.039 | 0.035 | 1.4 | 1.5 |
| UT-SCC-10 | 0.014 | 0.009 | 0.009 | 1.6 | 1.6 |
| UT-SCC-14 | 0.013 | 0.013 | 0.006 | 1.0 | 2.2 |
| UT-SCC-16A | 0.073 | 0.138 | 0.061 | 0.5 | 1.2 |
| UT-SCC-16B | 0.130 | 0.162 | 0.099 | 0.8 | 1.3 |
| UT-SCC-24A | 0.018 | 0.020 | 0.014 | 0.9 | 1.3 |

Compound 1 exhibits a comparable cytotoxicity in primary head and neck squamous cell carcinoma cell lines.
*Source: Turku University Hospital and University of Turku, Turku, Finland

Example 6

Pharmacokinetic Studies

The non-phosphorylated SMDC corresponding to compound 1 (Int 1-4) exhibits low to moderate solubility but was formulated to 50 mg/mL. Int 1-4 was advanced into stability and plasma/normal tissue PK studies.

Compound 1 was found to be soluble in water (>300 mg/mL) and was conveniently formulated for iv/sq administration.

a) Comparative Pharmacokinetic (PK) Studies of Non-Phosphorylated SMDC of Compound 1 (Int 1-4) Versus Gemcitabine in Mouse Plasma Background: Gemcitabine is known to deaminate into the inactive dFdU. Without wishing to be bound by theory, Int 1-4 is designed to be stable systemically and activated intra-tumorally to release 'free' gemcitabine.

Objectives: To compare the plasma pharmacokinetics and stability of Int 1-4 versus 'free' gemcitabine in plasma following single intravenous infusion administration of Int 1-4 at 10 mg/kg and gemcitabine at 5 mg/kg in CD-1 mice PK Measurements: compare PK parameters C0, CL, Vdss, Cmax, tmax, t½, AUC(0-t), AUC(0-inf), MRT(0-t), MRT(0-inf) for Int 1-4 and gemcitabine

| Compound | Species | # Animals | Dose | Formulation | Route | Time Points | Analytes |
|---|---|---|---|---|---|---|---|
| Int 1-4 | Mouse CD-1 | 3 | 9.4 mg/kg | 50% PEG400 (super-refined), 50% D5W | iv | 1.5, 3, 5, 10, 20, 30, 45 min, 1 hr, 4 hr, 8 hr | Int 1-4 Gemcitabine dFdU |
| Gemcitabine | Mouse CD-1 | 3 | 5.29 mg/kg | PBS | iv | 1.5, 3, 5, 10, 20, 30, 45 min, 1 hr, 4 hr, 8 hr | Gemcitabine dFdU |

Gemcitabine Pharmacokinetics in CD-1 Mice

| PK parameters | Gemcitabine (5.29 mg/kg) | dFdU |
|---|---|---|
| $C_0$ (ng/mL) | 6433 | — |
| $C_{max}$ (ng/mL) | — | 1600 |
| $T_{max}$ (h) | — | 0.667 |
| $T_{1/2}$ (h) | 0.868 | 2.23 |
| $Vd_{ss}$ (L/kg) | 1.84 | — |
| Cl (mL/min/kg) | 59.0 | — |
| $AUC_{0-last}$ (ng · h/mL) | 1383 | 6827 |
| $AUC_{0-inf}$ (ng · h/mL) | 1393 | 8187 |
| $MRT_{0-last}$ (h) | 0.503 | 2.56 |
| $MRT_{0-inf}$ (h) | 0.541 | 3.49 |
| $AUC_{0-inf}/AUC_{0-last}$ (%) | 101 | 111 |

Note:
— = no sample

Figure 2A:
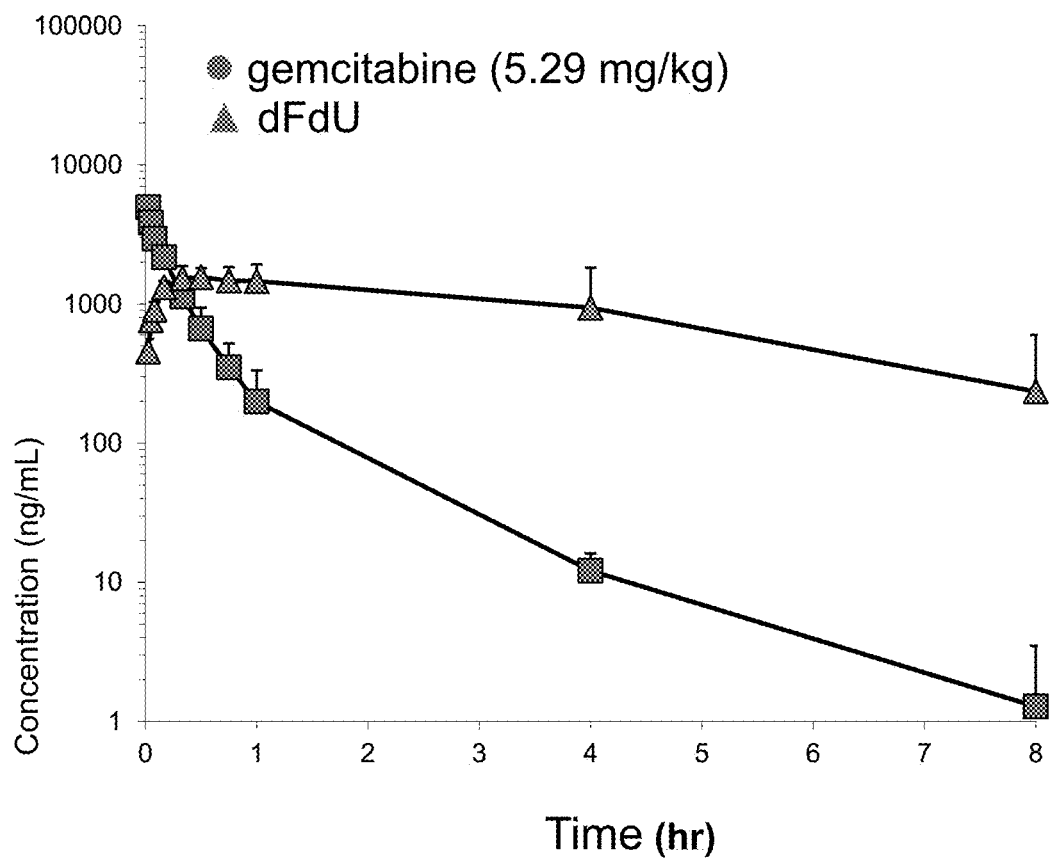
FIG. 2a shows the mean plasma concentration of gemcitabine and dFdU after iv dosing of gemcitabine to CD-1 mice.

The tabular above and FIG. 2a show that Gemcitabine is converted to inactive dFdU which has a long circulating half life and AUC and long exposure time. Based on the ratios of $AUC_{0-last}$ (ng·h/mL) plasma levels of dFdU are ~500% higher than gemcitabine. The data are consistent with the published literature.

Int 1-4 Pharmacokinetics in CD-1 Mice

| PK parameters | Int 1-4 (9.4 mg/kg) | Gemcitabine | dFdU |
|---|---|---|---|
| $C_0$ (ng/mL) | 78000 | — | — |
| $C_{max}$ (ng/mL) | — | 81.9 | 253 |
| $T_{max}$ (h) | — | 0.139 | 1.00 |
| $T_{1/2}$ (h) | 1.06 | 0.968 | 3.08 |
| $Vd_{ss}$ (L/kg) | 0.566 | — | — |
| Cl (mL/min/kg) | 27.1 | — | — |
| $AUC_{0-last}$ (ng · h/mL) | 4983 | 64.9 | 1039 |
| $AUC_{0-inf}$ (ng · h/mL) | 5000 | 74.1 | 1440 |
| $MRT_{0-last}$ (h) | 0.328 | 0.875 | 2.73 |
| $MRT_{0-inf}$ (h) | 0.346 | 1.27 | 4.65 |
| $AUC_{0-inf}/AUC_{0-last}$ (%) | 100 | 116 | 120 |

Note:
— = no sample

Figure 2B:
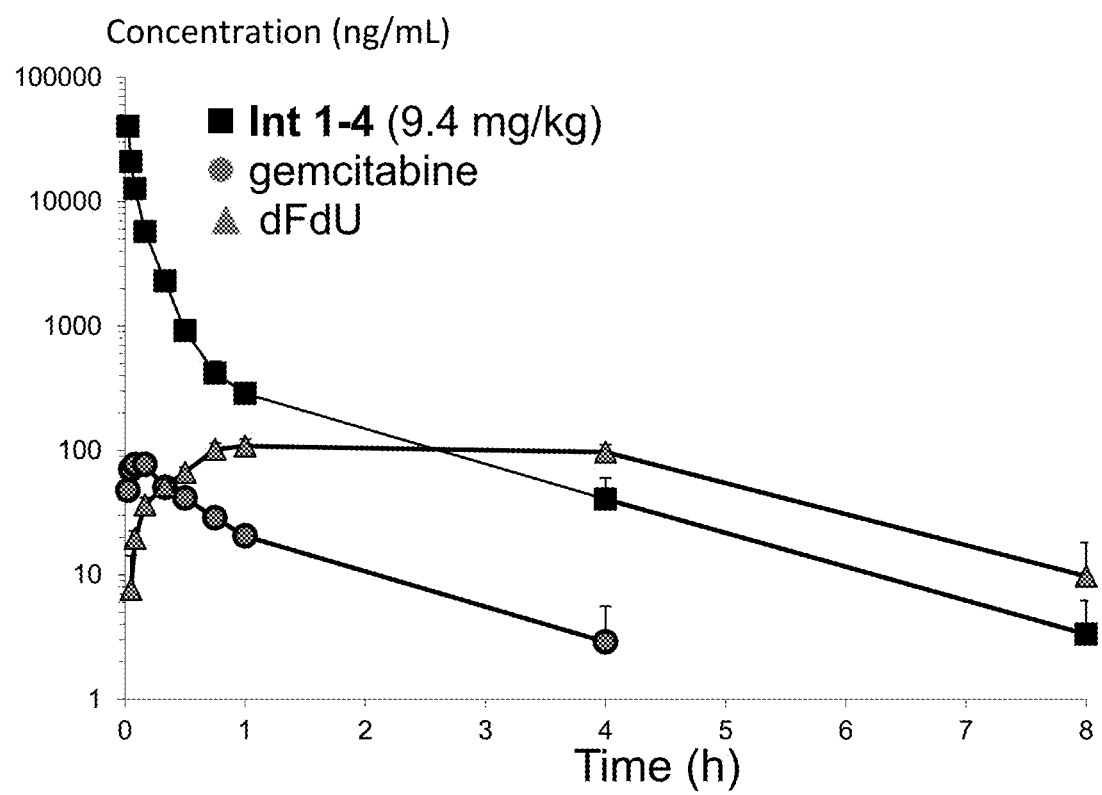
FIG. 2b shows the mean plasma concentration of Int 1-4, gemcitabine, and dFdU after iv dosing of Int 1-4 to CD-1 mice.
Figure 3A:
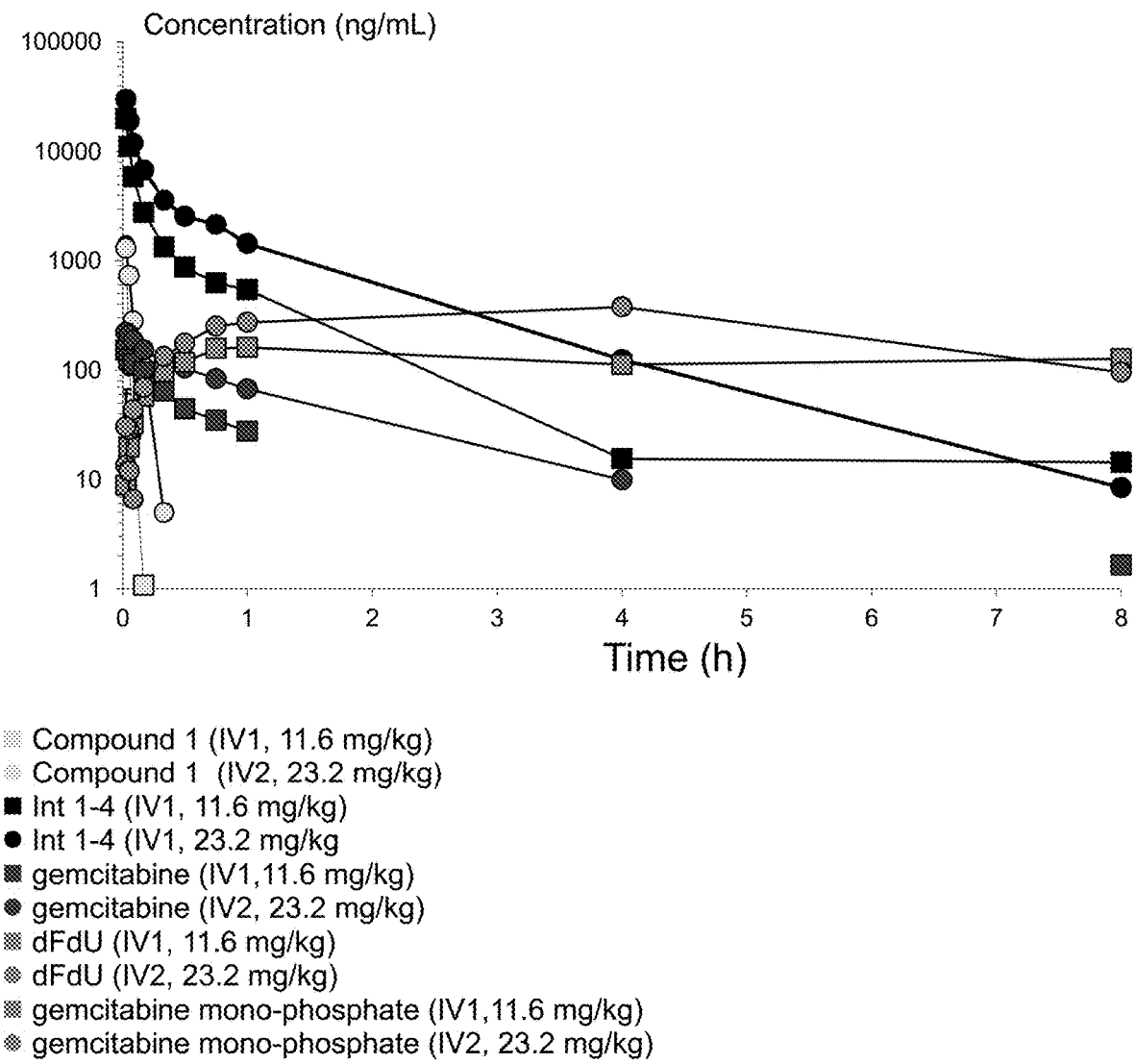
FIG. 3a shows the plasma concentrations of Compound 1, Int 1-4, gemcitabine, dFdU, and gemcitabine monophosphate after iv dosings of Compound 1 (11.6 mg/Kg and 23.2 mg/Kg) to male CD-1 mice.
Figure 3B:
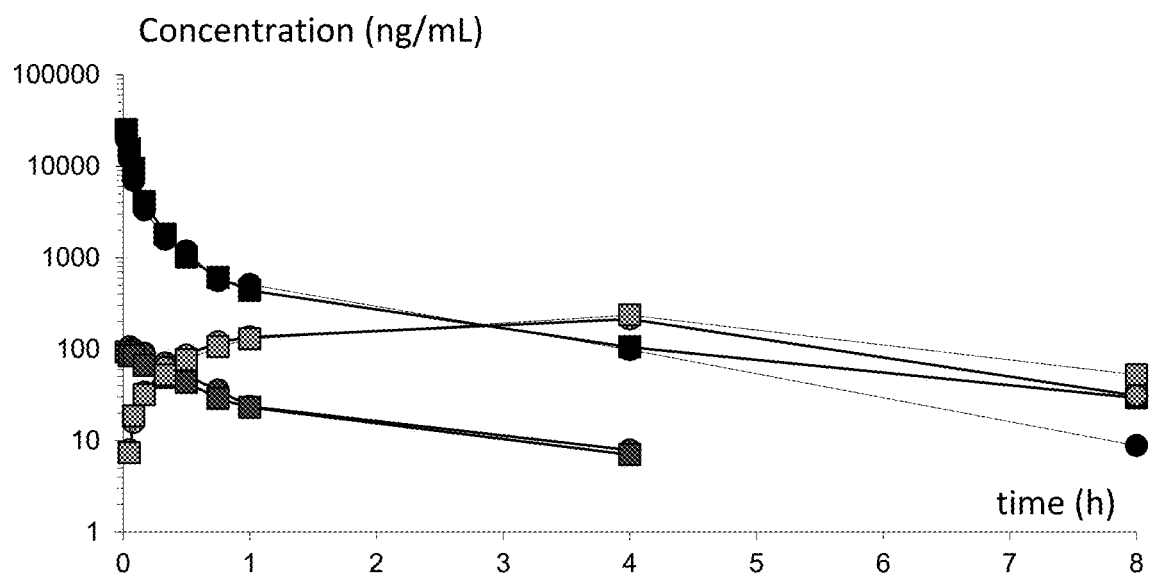
FIG. 3b shows the plasma concentrations of Compound 1, Int 1-4, gemcitabine, dFdU, and gemcitabine monophosphate after iv dosings of Int 1-4 (10.0 mg/Kg, Formulations 1 and 2) to male CD-1 mice.
Figure 4:
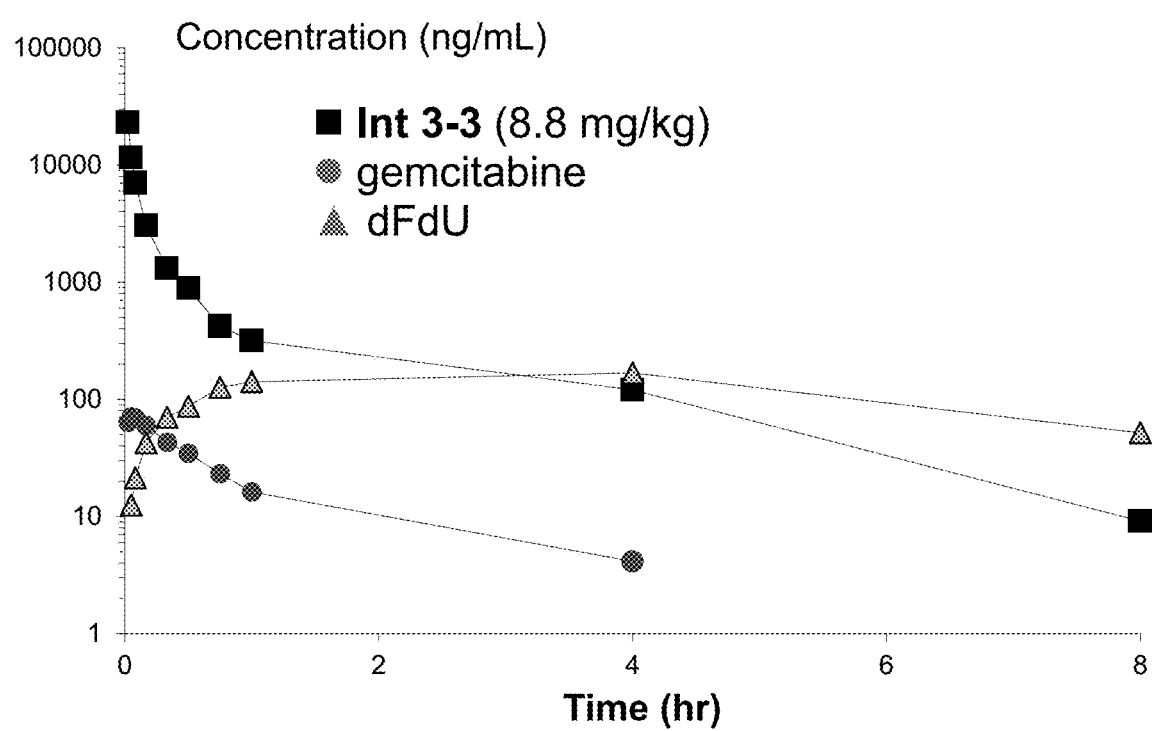
FIG. 4 shows the concentration of Int 3-3, gemcitabine, and dFdU after iv dosing of Int 3-3 after iv dosing to CD-1 mice.

Based on the ratios of $AUC_{0-last}$ (ng·h/mL) plasma levels of gemcitabine constitute ~1.3% of Int 1-4 administered (see tabular data above and FIG. 2b). Based on the ratios of $C_0$ and $C_{max}$ (ng/mL) the plasma levels of gemcitabine constitute 0.01% of Int 1-4 administered. Int 1-4 quickly clears the plasma and is taken up into tissue as demonstrated by normal tissue PK studies.

b) Comparative Pharmacokinetic (PK) Studies of Non-Phosphorylated SMDC of Compound 1 (Int 1-4) Versus Compound 1 in Male CD-1 Mice Objectives: to compare the plasma pharmacokinetics and stability of Compound 1 with its non-phosphorylated SMDC analog (Int 1-4) and in plasma following a single intravenous infusion administration of Compound 1 at 11.6 mg/kg and 23.2 mg/kg with Int 1-4 (formulation F1 & F2) at 10.0 mg/kg in male CD-1 mice PK measurements: compare PK parameters $C_0$, CL, Vdss, $C_{max}$, $t_{max}$, $t_{1/2}$, $AUC_{(0-t)}$, $AUC_{(0-inf)}$, $MRT_{(0-t)}$, $MRT_{(0-inf)}$ for Compound 1 and Int 1-4

| Compound | Species | # Animals | Dose | Formulation | Route | Time Points | Analytes |
|---|---|---|---|---|---|---|---|
| Compound 1 | Mouse CD-1 Male | 2 | 11.6 mg/kg & 23.2 mg/kg | PBS | iv | 1.5, 3, 5, 10, 20, 30, 45 min, 1 hr, 4 hr, 8 hr | Compound 1 Int 1-4 Gemcitabine, dFdU, Gemcitabine monophosphate |
| Int 1-4 | Mouse CD-1 Male | 2 | 10.0 mg/kg | (F1) 50% PEG400 (super-refined), 50% D5W & (F2) 5% NMP, 30% PEG 400, 15% Solutol HS15, 50% Lutrol F68 (5%) in Water | iv | 1.5, 3, 5, 10, 20, 30, 45 min, 1 hr, 4 hr, 8 hr | As above |

Comparison of Compound 1 Versus Int 1-4 in Mouse Plasma (IV1)

| PK parameters | Compound 1 | Int 1-4 (from Compound 1) | Gemcitabine (from Compound 1) | dFdU (from Compound 1) | Gemcitabine monophosphate (from Compound 1) |
|---|---|---|---|---|---|
| $C_0$ (ng/mL) | 11.6 mg/kg 21943 | — | — | — | — |
| $C_{max}$ (ng/mL) | — | 20000 | 152 | 220 | 33.6 |
| $T_{max}$ (h) | — | 0.0250 | 0.0250 | 3.25 | 0.0250 |
| $t_{1/2}$ (h) | 0.0147 | 0.974 | 1.04 | 2.38 | ND |
| Vdss (L/kg) | 1.41 | — | — | — | — |
| Cl (mL/min/kg) | 1972 | — | — | — | — |
| $AUC_{0-last}$ (ng · h/mL) | 202 | 2570 | 97.9 | 967 | 0.840 |
| $AUC_{0-inf}$ (ng · h/mL) | 202 | 2610 | 112 | 786 | ND |
| $MRT_{0-last}$ (h) | 0.0108 | 0.553 | 1.01 | 3.70 | 0.0298 |
| $MRT_{0-inf}$ (h) | 0.0109 | 0.673 | 1.41 | 3.81 | ND |

Comparison of Compound 1 Versus Int 1-4 in Mouse Plasma (IV2)

| PK parameters | Compound 1 | Int 1-4 (from Compound 1) | Gemcitabine (from Compound 1) | dFdU (from Compound 1) | Gemcitabine monophosphate (from Compound 1) |
|---|---|---|---|---|---|
| $C_0$ (ng/mL) | 23.2 mg/kg 2334 | — | — | — | — |
| $C_{max}$ (ng/mL) | — | 29933 | 222 | 378 | 30.4 |
| $T_{max}$ (h) | — | 0.0250 | 0.0333 | 4.00 | 0.0250 |
| $t_{1/2}$ (h) | 0.0363 | 0.930 | 1.03 | 2.86 | 0.0273 |
| Vdss (L/kg) | 12.0 | — | — | — | — |
| Cl (mL/min/kg) | 5193 | — | — | — | — |
| $AUC_{0-last}$ (ng · h/mL) | 103 | 6370 | 202 | 1960 | 1.18 |
| $AUC_{0-inf}$ (ng · h/mL) | 105 | 6383 | 218 | 1830 | 1.44 |
| $MRT_{0-last}$ (h) | 0.0426 | 0.778 | 1.11 | 3.65 | 0.0397 |
| $MRT_{0-inf}$ (h) | 0.0455 | 0.793 | 1.40 | 4.48 | 0.0550 |

Comparison of Compound 1 Versus Int 1-4 in Mouse Plasma (IV3)

| PK parameters | Compound 1 (from Int 1-4) | Int 1-4 Formulation 1 | Gemcitabine (from Int 1-4) | dFdU (from Int 1-4) | Gemcitabine monophosphate (from Int 1-4) |
|---|---|---|---|---|---|
| $C_0$ (ng/mL) | — | 10.0 mg/kg 33800 | — | — | — |
| $C_{max}$ (ng/mL) | ND | — | 107 | 213 | ND |
| $T_{max}$ (h) | ND | — | 0.0611 | 4.00 | ND |
| $t_{1/2}$ (h) | ND | 1.18 | 1.62 | 3.06 | ND |
| Vdss (L/kg) | — | 2.01 | — | — | — |
| Cl (mL/min/kg) | — | 48.3 | — | — | — |
| $AUC_{0-last}$ (ng · h/mL) | ND | 3623 | 98.6 | 983 | ND |
| $AUC_{0-inf}$ (ng · h/mL) | ND | 3633 | 120 | 1124 | ND |
| $MRT_{0-last}$ (h) | ND | 0.723 | 1.15 | 3.59 | ND |
| $MRT_{0-inf}$ (h) | ND | 0.756 | 1.98 | 4.67 | ND |

| PK parameters | Compound 1 (from Int 1-4) | Int 1-4 Formulation 2 | Gemcitabine (from Int 1-4) | dFdU (from Int 1-4) | Gemcitabine monophosphate (from Int 1-4) |
|---|---|---|---|---|---|
| $C_0$ (ng/mL) | — | 10.0 mg/kg 43000 | — | — | — |
| $C_{max}$ (ng/mL) | ND | — | 93.6 | 236 | ND |
| $T_{max}$ (h) | ND | — | 0.0333 | 4.00 | ND |
| $t_{1/2}$ (h) | ND | 1.82 | 1.66 | 4.15 | ND |
| Vdss (L/kg) | — | 2.30 | — | — | — |
| Cl (mL/min/kg) | — | 38.9 | — | — | — |
| $AUC_{0-last}$ (ng · h/mL) | ND | 4213 | 85.1 | 1106 | ND |
| $AUC_{0-inf}$ (ng · h/mL) | ND | 4293 | 102 | 1625 | ND |
| $MRT_{0-last}$ (h) | ND | 0.797 | 1.25 | 3.95 | ND |
| $MRT_{0-inf}$ (h) | ND | 0.984 | 2.10 | 5.89 | ND |

ND = not detected c) Pharmacokinetics of Int 3-3 (a Deuterated Analog of Int 1-4), the Non-Phosphorylated SMDC of Compound 3 (a Deuterated Analog of Compound 1).

Objectives: to determine the plasma pharmacokinetics of Int 3-3 following a single intravenous infusion of Int 3-3 at 8.83 mg/kg in CD-1 mice PK measurements: compare PK parameters $C_0$, CL, Vdss, $C_{max}$, $t_{max}$, $t_{1/2}$, $AUC_{(0-t)}$, $AUC_{(0-inf)}$, $MRT_{(0-t)}$, $MRT_{(0-inf)}$ for Int 3-3.

| Compound | Species | # Animals | Dose | Formulation | Route | Time Points | Analytes |
|---|---|---|---|---|---|---|---|
| Int 3-3 | Mouse CD-1 | 3 | 8.83 mg/kg | 50% PEG400 (super-refined), 50% D5W | iv | 1.5, 3, 5, 10, 20, 30, 45 min, 1 hr, 4 hr, 8 hr | Int 3-3, Gemcitabine, dFdU |

Int 3-3 Pharmacokinetics in CD-1 Mice

| PK parameters | Int 3-3 (8.8 mg/kg) | Gemcitabine | dFdU |
|---|---|---|---|
| $C_0$ (ng/mL) | 45933 | — | — |
| $C_{max}$ (ng/mL) | — | 73.4 | 168 |
| $T_{max}$ (h) | — | 0.0611 | 4.00 |
| $T_{1/2}$ (h) | 1.24 | 1.38 | 5.22 |
| $Vd_{ss}$ (L/kg) | 1.83 | — | — |
| Cl (mL/min/kg) | 43.3 | — | — |
| $AUC_{0-last}$ (ng · h/mL) | 3483 | 63.5 | 942 |
| $AUC_{0-inf}$ (ng · h/mL) | 3510 | 71.9 | 1403 |
| $MRT_{0-last}$ (h) | 0.704 | 1.13 | 3.67 |
| $MRT_{0-inf}$ (h) | 0.766 | 1.69 | 7.48 |
| $AUC_{0-inf}/AUC_{0-last}$ (%) | 101 | 113 | 146 | d) Int 1-4 Normal Tissue and Plasma PK in CD-1 Mice

Objectives: to compare the normal tissue pharmacokinetics, distribution, and stability of Int 1-4 in excretory organs following a single intravenous infusion administration of Int 1-4 at 20 mg/kg in male CD-1 mice.

PK measurements: compare PK parameters $C_0$, CL, Vdss, $C_{max}$, $t_{max}$, $t_{1/2}$, $AUC_{(0-t)}$, $AUC_{(0-inf)}$, $MRT_{(0-t)}$, $MRT_{(0-inf)}$ for Int 1-4

| Compound | Species | # Animals | Dose | Formulation | Route | Time Points | Analytes |
|---|---|---|---|---|---|---|---|
| Int 1-4 | Male CD-1 Mice | 3 | 18.4 mg/kg | 50% PEG400 (super-refined), 50% D5W | iv | 1.5, 3, 5, 10, 20, 30, 45 min, 1 hr, 4 hr, 8 hr | Int 1-4 Gemcitabine dFdU |
| Organs liver Kidney Spleen Plasma | | | | | | | |

Figure 5:
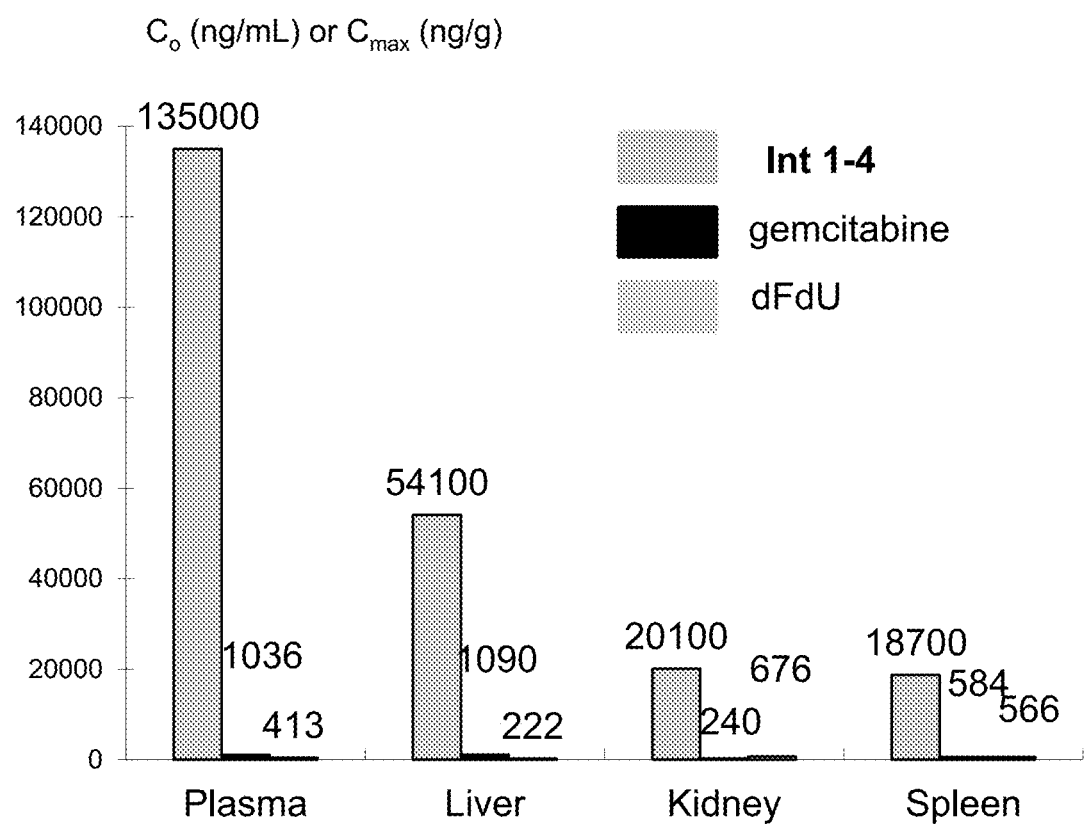
FIG. 5 shows the $C_0$ or Cmax of Int 1-4, gemcitabine, and dFdU in normal tissue and plasma after iv dosing of Int 1-4 to CD-1 mice.

As shown in FIG. 5, Int 1-4 is stable in the plasma and major excretory organs such as the liver and the kidney. Gemcitabine appears to deaminate into dFdU. 90% of gemcitabine is detoxified by cytidine deaminase which is prevented in the SMDC form.

e) Gemcitabine Normal Tissue and Plasma PK in CD-1 Mice

Objectives: to determine the normal tissue pharmacokinetics, distribution, and stability of gemcitabine in select excretory organs and plasma following a single intravenous infusion administration of gemcitabine at 10.5 mg/kg in male CD-1 mice.

PK measurements: determine PK parameters $C_0$, CL, Vdss, $C_{max}$, $t_{max}$, $t_{1/2}$, $AUC_{(0-t)}$, $AUC_{(0-inf)}$, $MRT_{(0-t)}$, $MRT_{(0-inf)}$ for gemcitabine

| Compound | Species | # Animals | Dose | Formulation | Route | Time Points | Analytes |
|---|---|---|---|---|---|---|---|
| Gemcitabine | Male CD-1 Mice | 3 | 10.5 mg/kg | 10 mM PBS | iv | 1.5, 3, 5, 10, 20, 30, 45 min, 1 hr, 4 hr, 8 hr | Gemcitabine dFdU |
| Organs liver Kidney Spleen Plasma | | | | | | | |

Figure 6:
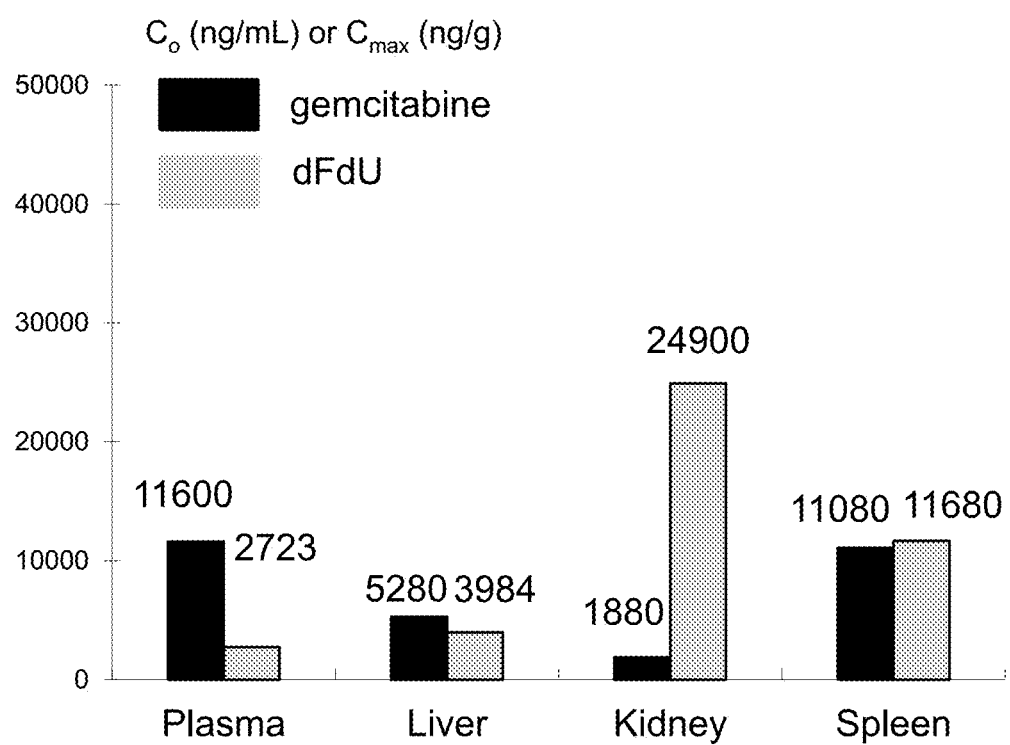
FIG. 6 shows the $C_0$ or Cmax of gemcitabine and dFdU in normal tissue and plasma 30 after iv dosing of gemcitabine to CD-1 mice.
Figure 7:
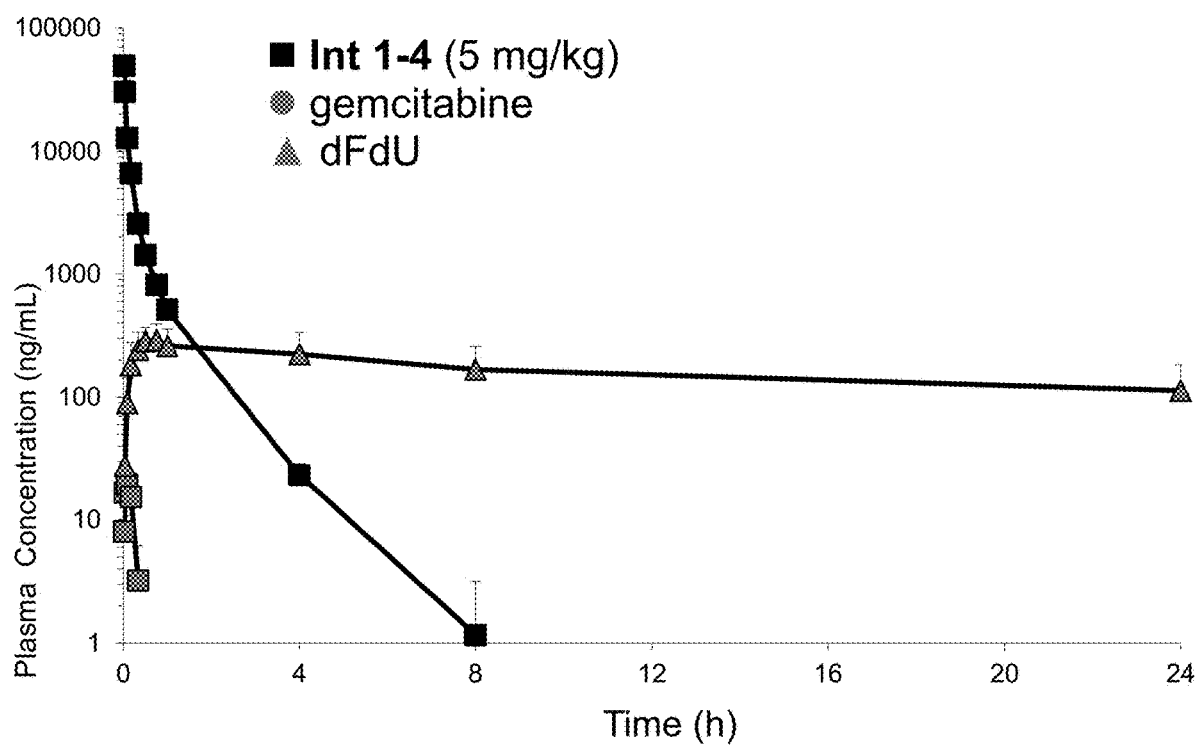
FIG. 7 shows the mean plasma concentrations of Int 1-4, gemcitabine, and dFdU after iv dosing of Int 1-4 in a male cynomolgus monkey.
Figure 8A:
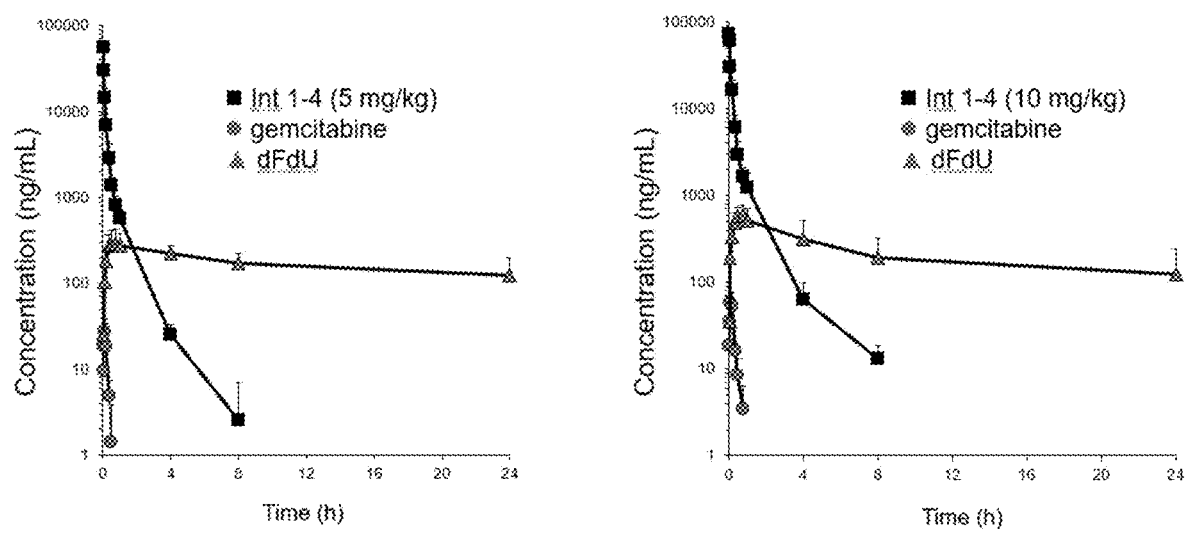
FIG. 8a shows the mean plasma concentrations of Int 1-4, gemcitabine, and dFdU after iv dosings of Int 1-4 in a male cynomolgus monkey.
Figure 8B:
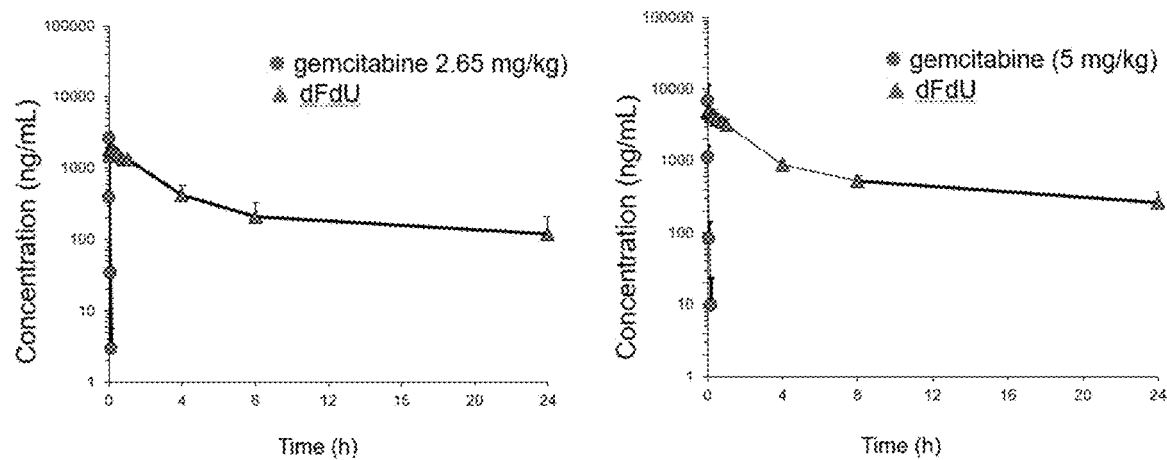
FIG. 8b shows the mean plasma concentrations of gemcitabine and dFdU after iv dosings of gemcitabine (at 2.65 and 5 mg/Kg) in a male cynomolgus monkey.
Figure 9A:
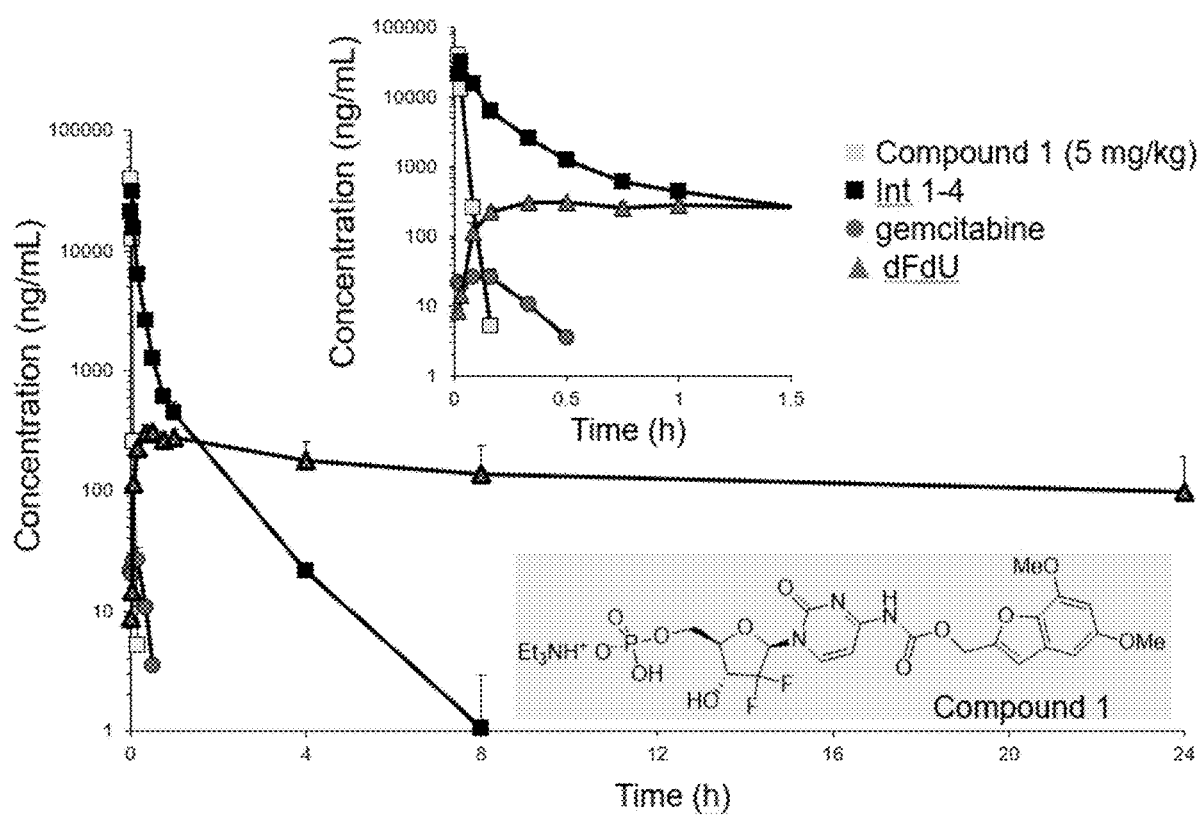
FIG. 9a shows the plasma concentrations of compound 1, Int 1-4, gemcitabine, and dFdU after iv dosing of compound 1 (5 mg/Kg) in a male cynomolgus monkey.
Figure 9B:
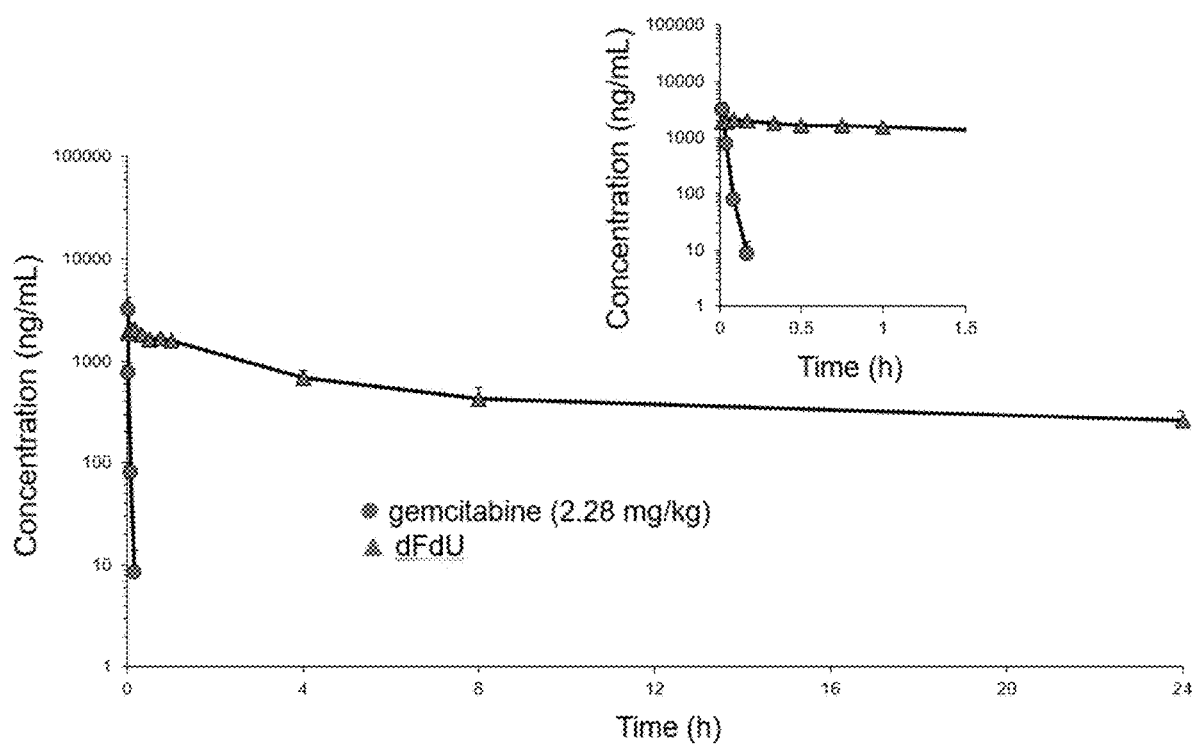
FIG. 9b shows the plasma concentration of gemcitabine and dFdU after iv dosing of gemcitabine in a male cynomolgus monkey.

As shown in FIG. 6, Gemcitabine is deaminated to dFdU in plasma and normal tissue. In the clinic 90% of injected dose is recovered in the urine, either as parent gemcitabine (1%) or dFdU (99%).

f) Int 1-4 Plasma PK in the Male Cynomolgus Monkey

Objectives: to compare the plasma pharmacokinetics and stability of Int 1-4 in plasma following single intravenous infusion administration of Int 1-4 at 5 mg/kg and 10 mg/kg in the male cynomolgus monkey PK measurements: compare PK parameters $C_0$, CL, Vdss, $C_{max}$, $t_{max}$, t, $AUC_{(0-t)}$, $AUC_{(0-inf)}$, $MRT_{(0-t)}$, $MRT_{(0-inf)}$ for Int 1-4

| Compound | Species | # Animals | Dose | Formulation | Route | Time Points | Analytes |
|---|---|---|---|---|---|---|---|
| Int 1-4 | Monkey Cynomolgus Male | 1 | 5 mg/kg | 50% PEG400 (super-refined), 50% D5W | iv | 1.5, 3, 5, 10, 20, 30, 45 min, 1 hr, 4 hr, 8 hr | Int 1-4 Gemcitabine dFdU |
| Int 1-4 | Monkey Cynomolgus Male | 1 | 10 mg/kg | 50% PEG400 (super-refined), 50% D5W | iv | 1.5, 3, 5, 10, 20, 30, 45 min, 1 hr, 4 hr, 8 hr | Int 1-4 Gemcitabine dFdU |

Int 1-4 Parameters in Male Cynomolgus Monkey

| | Int 1-4 | | Gemcitabine | | dFdU | |
|---|---|---|---|---|---|---|
| PK parameters | 5 mg/kg | 10 mg/kg | 5 mg/kg | 10 mg/kg | 5 mg/kg | 10 mg/kg |
| $C_0$ (ng/mL) | 81000 | 166000 | 20.5 | 53.4 | 296 | 747 |
| $t_{1/2}$ (h) | 0.73 | 0.93 | 0.047 | 0.08 | 0.67 | 0.75 |
| $Vd_{ss}$ (L/kg) | 0.301 | 0.253 | 0.11 | 0.19 | 21.11 | 44.16 |
| Cl (mL/min/kg) | 15.4 | 9.65 | 3.71 | 15.5 | 3947 | 8710 |
| $AUC_{0-last}$ (ng · h/mL) | 5460 | 17367 | 6.41 | 16.7 | 7630 | 28100 |
| $AUC_{0-inf}$ (ng · h/mL) | 5473 | 17400 | 0.13 | 0.24 | 10.18 | 10.40 |
| $MRT_{0-last}$ (h) | 0.31 | 0.43 | 0.19 | 0.30 | 30.60 | 63.00 |
| $MRT_{0-inf}$ (h) | 0.33 | 0.44 | 20.5 | 53.4 | 296 | 747 | g) Int 1-4 and Gemcitabine Comparative PK in Male Cynomolgus Monkey

Objectives: to compare the plasma pharmacokinetics and stability of Int 1-4 versus gemcitabine in plasma following single intravenous infusion administration of Int 1-4 at 5 mg/kg and 10 mg/kg with equimolar gemcitabine at 2.65 mg/kg and 5.29 mg/kg in male cynomolgous monkeys PK measurements: compare PK parameters $C_0$, CL, Vdss, $C_{max}$, $t_{max}$, $t_{1/2}$, $AUC_{(0-t)}$, $AUC_{(0-inf)}$, $MRT_{(0-t)}$, $MRT_{(0-inf)}$ for Int 1-4 with gemcitabine

| Compound | Species | # Animals | Dose | Formulation | Route | Time Points | Analytes |
|---|---|---|---|---|---|---|---|
| Int 1-4 | Monkey Cynomolgus Male | 1 | 5 mg/kg & 10 mg/kg | 50% PEG400 (super-refined), 50% D5W | iv | 1.5, 3, 5, 10, 20, 30, 45 min, 1 hr, 4 hr, 8 hr | Int 1-4 Gemcitabine dFdU |
| Gemcitabine | Monkey Cynomolgus Male | 1 | 2.65 mg/kg & 5.29 mg/kg | PBS | iv | 1.5, 3, 5, 10, 20, 30, 45 min, 1 hr, 4 hr, 8 hr | Gemcitabine dFdU |

Int 1-4 PK Parameters in Male Cynomolgus Monkey

| | Int 1-4 | | Gemcitabine | | dFdU | |
|---|---|---|---|---|---|---|
| PK parameters | 5 mg/kg | 10 mg/kg | 5 mg/kg | 10 mg/kg | 5 mg/kg | 10 mg/kg |
| $C_0$(ng/mL) | 99700 | 145733 | | | | |
| $C_{max}$ (ng/mL) | | | 27.3 | 60.3 | 302 | 595 |
| $t_{max}$(h) | | | 0.08 | 0.08 | 1.69 | 0.67 |
| $t_{1/2}$(h) | 0.75 | 0.99 | 0.15 | 0.18 | 16.86 | 12.87 |
| $Vd_{ss}$ (L/kg) | 0.287 | 0.349 | 0.349 | | | |
| Cl (mL/min/kg) | 14.6 | 15.0 | | | | |
| $AUC_{0-last}$ (ng·h/mL) | 5947 | 11897 | 5.37 | 16.2 | 4117 | 5120 |
| $AUC_{0-inf}$ (ng·h/mL) | 5963 | 11900 | 8.13 | 17.5 | 5555 | 7903 |
| $MRT_{0-last}$ (h) | 0.32 | 0.38 | 0.15 | 0.21 | 10.31 | 8.30 |
| $MRT_{0-inf}$ (h) | 0.33 | 0.39 | 0.24 | 0.26 | 24.01 | 18.02 |

Gemcitabine PK in Male Cynomolgus Monkey

| PK parameters | Gemcitabine (2.65 mg/kg) | dFdU |
|---|---|---|
| $C_0$ (ng/mL) | 16950 | |
| Cmax (ng/mL) | | 1973 |
| Tmax (h) | | 0.09 |
| $t_{1/2}$ (h) | 0.02 | 5.89 |
| $Vd_{ss}$ (L/kg) | 0.221 | |
| Cl (mL/min/kg) | 323 | |
| $AUC_{0-last}$ (ng·h/mL) | 154 | 7703 |
| $AUC_{0-inf}$ (ng·h/mL) | 154 | 8837 |
| $MRT_{0-last}$ (h) | 0.01 | 6.41 |
| $MRT_{0-inf}$ (h) | 0.01 | 9.35 |

Based on the ratio of gemcitabine/Int 1-4 $C_{max}$ values 0.09% free gemcitabine in the plasma indicating low systemic exposure Gemcitabine has a half-life of 0.02 h in the monkey and is inactivated to dFdU whereas Int 1-4 has a ~50-fold longer half-life and greater stability. The volume of distribution of gemcitabine VDss=0.221 L/kg is comparable to Int 1-4. VDss=0.287 L/kg at equimolar 2.65 mg/kg and 5 mg/kg dosing in the monkey meaning the plasma versus whole body water distribution of Int 1-4 and drug are similar. Int 1-4 PK parameters in monkey plasma PK studies compare favorably to free drug gemcitabine but Int 1-4 exhibits improved metabolic stability.

h) Compound and Gemcitabine Plasma PK in the Male Cynomolgus Monkey

Objectives: to compare the plasma pharmacokinetics and stability of the Compound 1 with Int 1-4 and in plasma following a single intravenous infusion administration of Compound 1 at 5 mg/kg and 10 mg/kg with equimolar gemcitabine at 2.28 mg/kg in male cynomolgous monkeys.

PK measurements: compare PK parameters $C_0$, CL, Vdss, $C_{max}$, $t_{max}$, $t_{1/2}$, $AUC_{(0-t)}$, $AUC_{(0-inf)}$, $MRT_{(0-t)}$, $MRT_{(0-inf)}$ for Compound 1 and Int 1-4 with gemcitabine.

| Compound | Species | # Animals | Dose | Formulation | Route | Time Points | Analytes |
|---|---|---|---|---|---|---|---|
| Compound 1 | Monkey Cynomolgus Male | 1 | 5 mg/kg & 10 mg/kg | 50% PEG400 (super-refined), 50% D5W | iv | 1.5, 3, 5, 10, 20, 30, 45 min, 1 hr, 4 hr, 8 hr | Int 1-4, Gemcitabine, dFdU |
| Gemcitabine | Monkey Cynomolgus Male | 1 | 2.28 mg/kg | PBS | iv | 1.5, 3, 5, 10, 20, 30, 45 min, 1 hr, 4 hr, 8 hr | Gemcitabine, dFdU |

Comparison of Compound 1 Versus Int 1-4 in Monkey Plasma

| PK parameters | Compound 1 5 mg/kg | Int 1-4 (from Compound 1) 5 mg/kg | Gemcitabine (from Compound 1) 5 mg/kg | dFdU (from Compound 1) 5 mg/kg | Gemcitabine 2.28 mg/kg | dFdU (from gemcitabine) 2.28 mg/kg |
|---|---|---|---|---|---|---|
| $C_0$ (ng/mL) | 138667 | | | | 13380 | |
| $C_{max}$ (ng/mL) | | 31500 | 28.6 | 321 | | 2153 |
| $T_{max}$ (h) | | | 0.14 | 0.39 | | 0.04 |
| $t_{1/2}$ (h) | 0.01 | 0.76 | 0.13 | 24.00 | 0.02 | 12.90 |
| Vdss (L/kg) | 0.0357 | | | | 0.231 | |
| Cl (mL/min/kg) | 46.5 | | | | 247 | |
| $AUC_{0\text{-}last}$ (ng·h/mL) | 1833 | 4383 | 7.85 | 3397 | 164 | 12467 |
| $AUC_{0\text{-}inf}$ (ng·h/mL) | 0.01 | 4397 | 7.00 | 8767 | 165 | 17600 |
| $MRT_{0\text{-}last}$ (h) | 0.01 | 0.36 | 0.19 | 8.98 | 0.02 | 8.21 |
| $MRT_{0\text{-}inf}$ (h) | 0.01 | 0.37 | 0.23 | 34.42 | 0.02 | 18.06 |

Compound 1 has plasma half-life of 0.01 h and is converted to Int 1-4 likely by phosphatase enzymes. Compound 1 is therefore a soluble prodrug of Int 1-4 and will be useful for iv administration in the clinic in PBS similarly to the HCl salt of gemcitabine. Based on the ratio of gemcitabine/Int 1-4 $C_{max}$ values, 0.09% free gemcitabine is in the plasma with low systemic exposure. Gemcitabine has a short half-life of 0.02 h in the monkey and is inactivated to dFdU. The high volume of distribution for compound 1 of VDss=0.0357 L/kg is 10-fold lower than Int 1-4. Without wishing to be bound by theory, this observation is consistent with a charged hydrophilic prodrug remaining in the plasma while Int 1-4 distributes more into the body water. The PK parameters for compound 1 and metabolite Int 1-4 are consistent with prodrug/drug conversion.

i) Comparative Pharmacokinetics of Int 1-4 Versus Gemcitabine in Rat Plasma

Objectives: to compare the plasma pharmacokinetics and stability of Int 1-4 versus 'free' gemcitabine in plasma following single intravenous infusion administration of Int 1-4 at 10 mg/kg and gemcitabine at 4.71 mg/kg in Sprague-Dawley rats.

PK measurements: compare PK parameters $C_0$, CL, Vdss, $C_{max}$, $t_{max}$, $t_{1/2}$, $AUC_{(0\text{-}t)}$, $AUC_{(0\text{-}inf)}$, $MRT_{(0\text{-}t)}$, $MRT_{(0\text{-}inf)}$ for Int 1-4 and gemcitabine.

| Compound | Species | # Animals | Dose | Formulation | Route | Time Points | Analytes |
|---|---|---|---|---|---|---|---|
| Int 1-4 | Sprague-Dawley Rats | 3 | 10.0 mg/kg | 50% PEG400 (super-refined), 50% D5W | iv | 1.5, 3, 5, 10, 20, 30, 45 min, 1 hr, 4 hr, 8 hr | Int 1-4, Gemcitabine, dFdU |

| Compound | Species | # Animals | Dose | Formulation | Route | Time Points | Analytes |
|---|---|---|---|---|---|---|---|
| Gemcitabine | Sprague-Dawley Rats | 3 | 4.71 mg/kg | PBS | iv | 1.5, 3, 5, 10, 20, 30, 45 min, 1 hr, 4 hr, 8 hr | Gemcitabine dFdU |

Figure 10A:
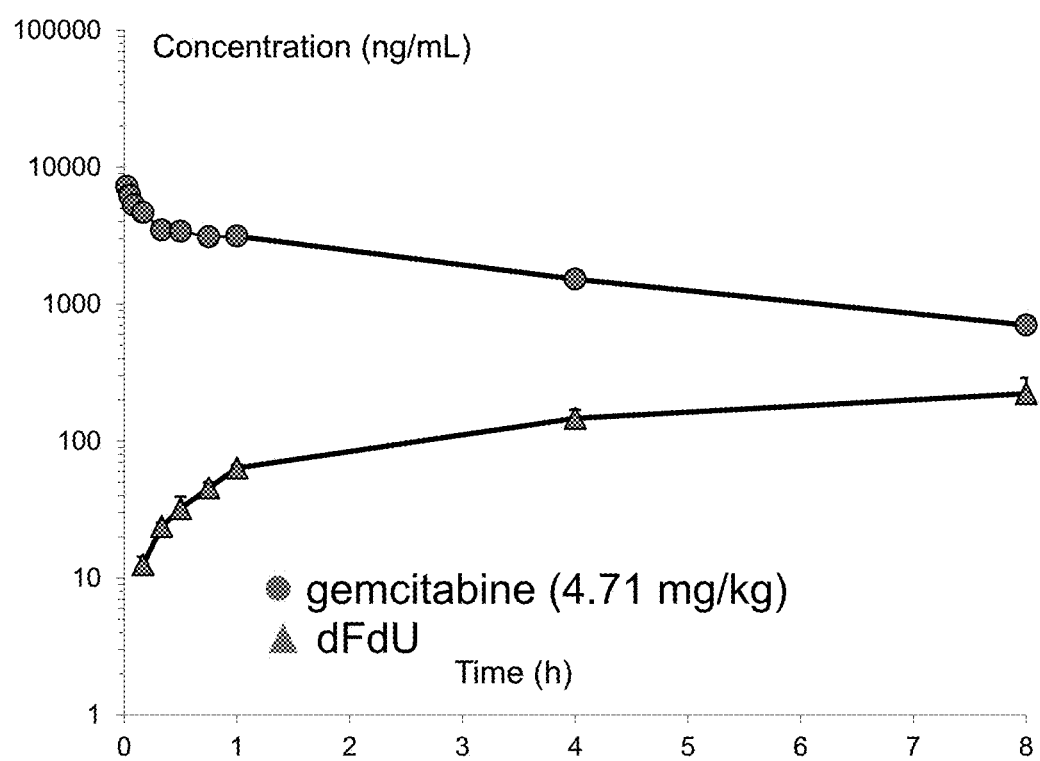
FIG. 10a shows the mean plasma concentration of gemcitabine and dFdU after iv dosing of gemcitabine to male Sprague-Dawley rats.
Figure 10B:
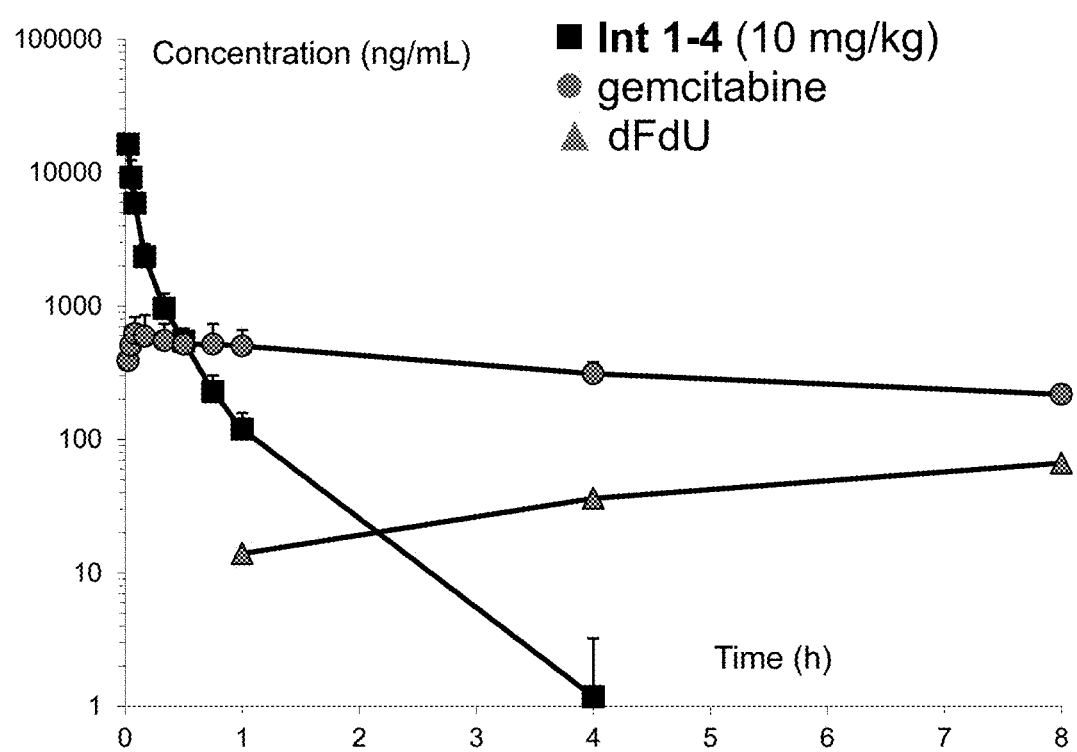
FIG. 10b shows the mean plasma concentration of Int 1-4, gemcitabine, and dFdU after iv dosing of Int 1-4 to male Sprague-Dawley rats.
Figure 11:
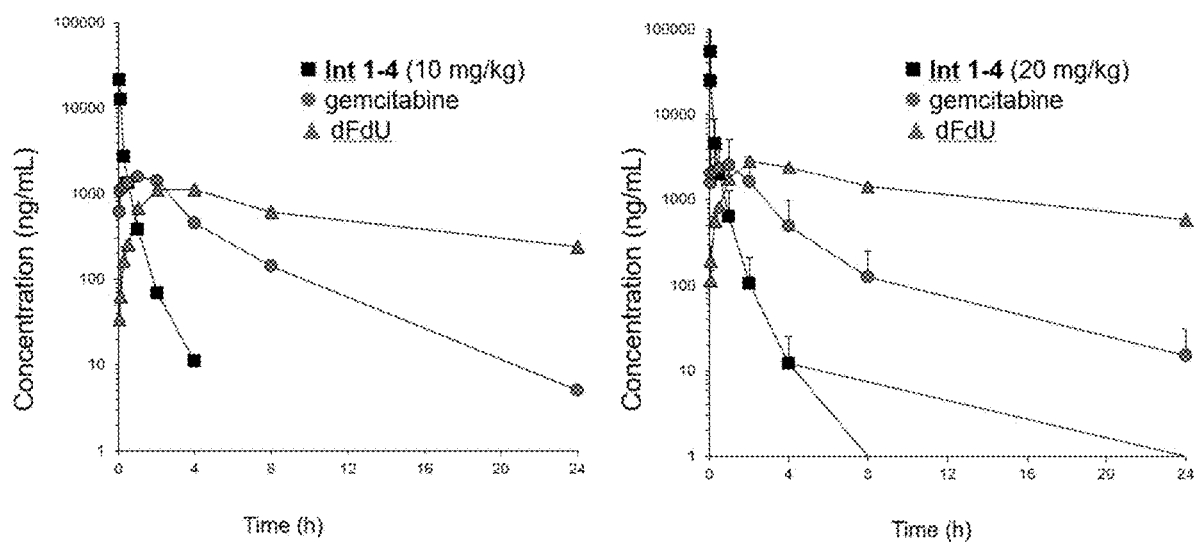
FIG. 11 shows the mean plasma concentration of Int 1-4, gemcitabine, and dFdu after iv dosings of Int 1-4 to male beagle dog.
Figure 12A:
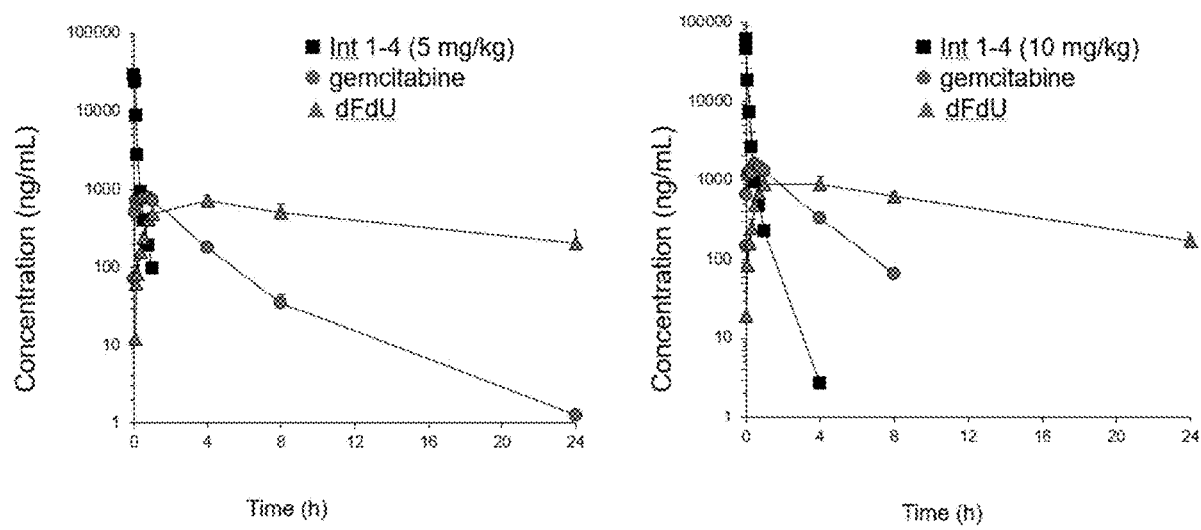
FIG. 12a shows the mean plasma concentration of Int 1-4, gemcitabine, and dFdu after iv dosings of Int 1-4 to male beagle dog.
Figure 12B:
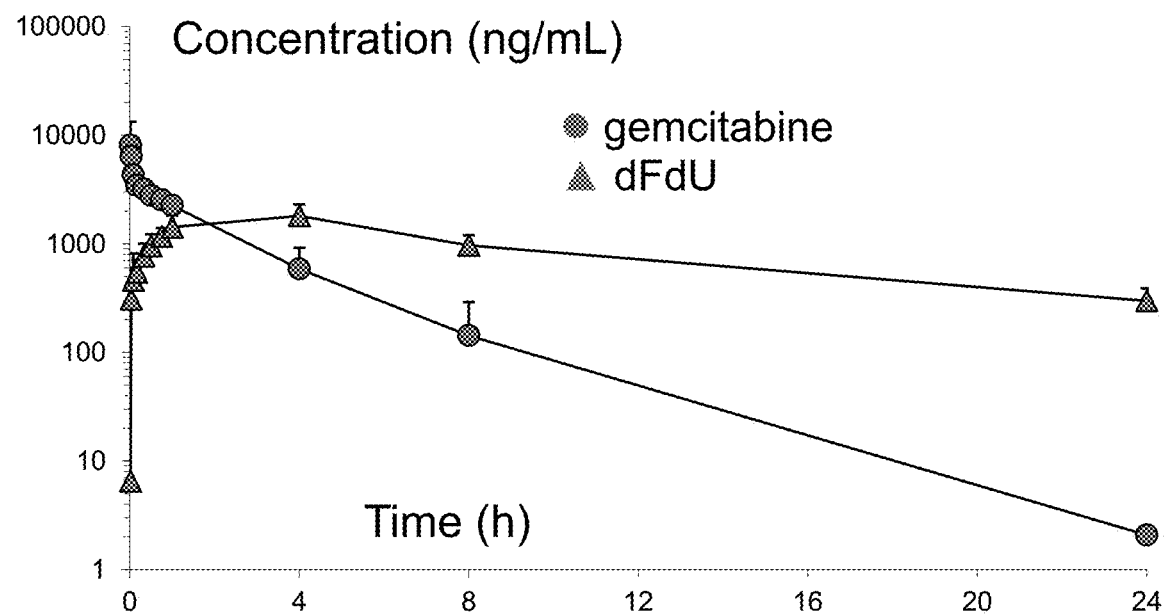
FIG. 12b shows the mean plasma concentration of gemcitabine and dFdu after iv dosing of gemcitabine to male beagle dog.

Gemcitabine has a much longer plasma half-life ($t\frac{1}{2}$) in rats, 3× than in mice (FIG. 10a):
- rat plasma $t_{1/2}$~3.3 h
- mouse plasma $t_{1/2}$~0.9 h Gemcitabine Pharmacokinetics in the Sprague-Dawley Rat

| PK parameters | Gemcitabine (4.47 mg/kg) | dFdU |
|---|---|---|
| $C_0$ (ng/mL) | 8410 | — |
| $C_{max}$ (ng/mL) | — | 222 |
| $T_{max}$ (h) | — | 8.00 |
| $T_{1/2}$ (h) | 3.26 | ND |
| $Vd_{ss}$ (L/kg) | 1.21 | — |
| Cl (mL/min/kg) | 4.36 | — |
| $AUC_{0\text{-}last}$ (ng · h/mL) | 14733 | 1085 |
| $AUC_{0\text{-}inf}$ (ng · h/mL) | 18033 | ND |
| $MRT_{0\text{-}last}$ (h) | 2.82 | 5.25 |
| $MRT_{0\text{-}inf}$ (h) | 4.63 | ND |
| $AUC_{0\text{-}inf}/AUC_{0\text{-}last}$ (%) | 122 | ND |

— = No sample;
ND = not determined

Int 1-4 Pharmacokinetics in the Sprague-Dawley Rat

| PK parameters | Int 1-4 (10.0 mg/kg) | Gemcitabine | dFdU |
|---|---|---|---|
| $C_0$ (ng/mL) | 29400 | — | — |
| $C_{max}$ (ng/mL) | — | 636 | 66.5 |
| $T_{max}$ (h) | — | 0.111 | 8.00 |
| $T_{1/2}$ (h) | 0.319 | 9.43 | ND |
| $Vd_{ss}$ (L/kg) | 0.905 | — | — |
| Cl (mL/min/kg) | 82.3 | — | — |
| $AUC_{0\text{-}last}$ (ng · h/mL) | 1990 | 2763 | 288 |
| $AUC_{0\text{-}inf}$ (ng · h/mL) | 2010 | 6000 | ND |
| $MRT_{0\text{-}last}$ (h) | 0.171 | 3.38 | 5.55 |
| $MRT_{0\text{-}inf}$ (h) | 0.185 | 13.8 | ND |
| $AUC_{0\text{-}inf}/AUC_{0\text{-}last}$ (%) | 101 | 235 | ND |

Int 1-4 is unstable in the rat based on higher $C_{max}$ and AUC values for free gemcitabine in the plasma.
- rat plasma gemcitabine $t_{1/2}$~9.43 h j) Int 1-4 Dog Plasma Pharmacokinetics Objectives: to compare the plasma pharmacokinetics and stability of Int 1-4 in plasma following single intravenous infusion administration of t 1-4 at 10 mg/kg and 20 mg/kg in the male Beagle dog.

PK measurements: compare PK parameters C, CL, Vdss, % max, $t_{max}$, $t_{1/2}$, $AUC_{(0\text{-}t)}$, $AUC_{(0\text{-}inf)}$, $MRT_{(0\text{-}t)}$, $MRT_{(0\text{-}inf)}$ for Int 1-4 at 10 and 20 mg/kg.

| Compound | Species | # Animals | Dose | Formulation | Route | Time Points | Analytes |
|---|---|---|---|---|---|---|---|
| Int 1-4 | Dog Beagle | 3 | 9.7 mg/kg | 50% PEG400 (super-refined), 50% D5W | iv | 3.3, 8.3, 25, 50 min, 1 hr, 2 hr, 4 hr, 8 hr, 24 hr | Int 1-4 Gemcitabine dFdU |
| Int 1-4 | Dog Beagle | 3 | 18.3 mg/kg | 50% PEG400 (super-refined), 50% D5W | iv | 3.3, 8.3, 25, 50 min, 1 hr, 2 hr, 4 hr, 8 hr, 24 hr | Int 1-4 Gemcitabine dFdU |

Int 1-4 PK Parameters in Male Beagle Dog

| PK parameters | Int 1-4 | | Gemcitabine | | dFdU | |
|---|---|---|---|---|---|---|
| | 10 mg/kg | 20 mg/kg | 10 mg/kg | 20 mg/kg | 10 mg/kg | 20 mg/kg |
| $C_0$ (ng/mL) | 60533 | 90933 | | | | |
| $C_{max}$ (ng/mL) | | | 1660 | 2707 | 1173 | 2873 |
| $t_{max}$ (h) | | | 0.75 | 0.67 | 3.33 | 2.00 |
| $t_{1/2}$ (h) | 0.54 | 0.52 | 3.10 | 3.55 | 10.0 | 10.53 |
| $Vd_{ss}$ (L/kg) | 0.504 | 0.58 | | | | |
| Cl (mL/min/kg) | 35.2 | 43.3 | | | | |
| $AUC_{0-last}$ (ng · h/mL) | 4733 | 7933 | 6160 | 7687 | 13167 | 31267 |
| $AUC_{0-inf}$ (ng · h/mL) | 4743 | 7940 | 6183 | 7880 | 14300 | 40233 |
| $MRT_{0-last}$ (h) | 0.23 | 0.22 | 3.47 | 2.69 | 9.20 | 9.27 |
| $MRT_{0-inf}$ (h) | 0.24 | 0.23 | 3.56 | 3.28 | 15.33 | 15.97 | k) Comparative Dog Plasma PK of Int 1-4 Versus Gemcibatine

Objectives: to compare the plasma pharmacokinetics and stability of Int-4 in plasma following single intravenous infusion administration of Int 1-4 at 5 mg/kg and 10 mg/kg versus gemcitabine at 5 mg/kg in the male Beagle dog PK measurements: compare PK parameters $C_0$, CL, Vdss, $C_{max}$, $t_{max}$, $t_{1/2}$, $AUC_{(0-t)}$, $AUC_{(0-inf)}$, $MRT_{(0-t)}$, $MRT_{(0-inf)}$ for Int 1-4 at 5 and 10 mg/kg versus gemcitabine at 5 mg/kg

| Compound | Species | # Animals | Dose | Formulation | Route | Time Points | Analytes |
|---|---|---|---|---|---|---|---|
| Int 1-4 | Dog Beagle | 3 | 4.88 mg/kg | 50% PEG400 (super-refined), 50% D5W | iv | 1.7, 3.3, 8.3, 16.7, 33.3, 50 min, 0.75 hr, 1 hr, 2 hr, 4 hr, 8 hr, 24 hr | Int 1-4 Gemcitabine dFdU |
| Int 1-4 | Dog Beagle | 3 | 9.50 mg/kg | 50% PEG400 (super-refined), 50% D5W | iv | As above | Int 1-4 Gemcitabine dFdU |
| Gemcitabine | Dog Beagle | 3 | 4.88 mg/kg | PBS | iv | As above | Gemcitabine dFdU |

Int 1-4 PK Parameters in Male Beagle Dog

| PK parameters | Int 1-4 | | Gemcitabine | | dFdU | |
|---|---|---|---|---|---|---|
| | 5 mg/kg | 10 mg/kg | 5 mg/kg | 10 mg/kg | 5 mg/kg | 10 mg/kg |
| $C_0$ (ng/mL) | 40033 | 90933 | | | | |
| $C_{max}$ (ng/mL) | 30533 | | 872 | 1690 | 715 | 936 |
| $t_{max}$ (h) | | | 0.39 | 0.39 | 4.00 | 2.00 |
| $t_{1/2}$ (h) | 0.25 | 0.52 | 2.01 | 1.60 | 11.79 | 8.40 |
| $Vd_{ss}$ (L/kg) | 0.23 | 0.58 | | | | |
| Cl (mL/min/kg) | 30.8 | 43.3 | | | | |
| $AUC_{0-last}$ (ng · h/mL) | 2697 | 7933 | 2333 | 4140 | 9863 | 11700 |
| $AUC_{0-inf}$ (ng · h/mL) | 2733 | 7940 | 2387 | 4290 | 13743 | 13800 |
| $MRT_{0-last}$ (h) | 0.11 | 0.22 | 2.48 | 2.16 | 9.89 | 8.94 |
| $MRT_{0-inf}$ (h) | 0.12 | 0.23 | 2.70 | 2.45 | 18.22 | 12.99 |

Gemcitabine Pharmacokinetics in Male Beagle Dog

| PK parameters | Gemcitabine (5.29 mg/kg) | dFdU |
|---|---|---|
| $C_0$ (ng/mL) | 11480 | |
| Cmax (ng/mL) | 8620 | 1813 |
| Tmax (h) | | 3.00 |
| $t_{1/2}$ (h) | 2.04 | 8.55 |
| $Vd_{ss}$ (L/kg) | 1.61 | |
| Cl (mL/min/kg) | 11.0 | |
| $AUC_{0-last}$ (ng · h/mL) | 8230 | 20133 |
| $AUC_{0-inf}$ (ng · h/mL) | 8600 | 23967 |
| $MRT_{0-last}$ (h) | 2.19 | 8.71 |
| $MRT_{0-inf}$ (h) | 2.50 | 13.31 |

Example 7 a) Metabolic Stability of Int 1-4 and Compound 1 in Human, Rat, and Mouse Plasma Half Life Values of Test Compounds in Human Plasma Stability Experiment Method: Assay was carried out in 96-well microtiter plates. Compounds were incubated in replicates (n=2) for 0, 5, 15, 30, and 45 minutes at 37° C. Reaction mixtures (20 µL) contained a final concentration of 3 µM test compound in human plasma. Eucatropine included as positive control to verify assay performance. Linear regression of semi-log plot of % remaining of compounds versus time used to determine the half-life t½ values. Int 1-4 was found to be stable in human plasma based on repeat measurements

| Compound | Slope Mean ± SE | $t_{1/2}$ (min) Mean ± SE |
|---|---|---|
| Eucatropine | −0.045910 ± 0.003277 | 15.1 ± 1.1 |
| Int 1-4 | 0.001033 ± 0.001249 | −670.9* ± 811.1 |

*Negative value indicates compound is stable

Half Life Values of Test Compounds in CD-1 Mouse Plasma Stability Experiment

Method: Assay was carried out in 96-well microtiter plates. Compounds were incubated in replicates (n=2) for 0, 5, 15, 30, and 45 minutes at 37° C. Reaction mixtures (20 µL) contained a final concentration of 3 µM test compound in fresh CD-1 mouse plasma. Eucatropine included as positive control to verify assay performance. Linear regression of semi-log plot of % remaining of compounds versus time used to determine the half-life $t_{1/2}$ values. Int 1-4 was stable in CD-1 mouse plasma with $t_{1/2}$~13 h.

| Compound | Slope Mean ± SE | $t_{1/2}$ (min) Mean ± SE |
|---|---|---|
| Eucatropine | −0.030840 ± 0.003016 | 22.5 ± 2.2 |
| Int 1-4 | −0.000906 ± 0.000706 | 765.1 ± 596.5 |

Half Life Values of Test Compounds in Rat Plasma Stability Experiment

Method: Assay was carried out in 96-well microtiter plates. Compounds were incubated in replicates (n=2) for 0, 5, 15, 30, and 45 minutes at 37° C. Reaction mixtures (20 μL) contained a final concentration of 3 μM test compound in fresh Sprague Dawley rat plasma. Eucatropine is a positive control to verify assay performance. Linear regression of semi-log plot of % remaining of compounds versus time used to determine the half-life $t_{1/2}$ values. Int 1-4 was found to be less stable in Sprague Dawley rat plasma with $t_{1/2}$~1.2 h.

| Compound | Slope Mean ± SE | $t_{1/2}$ (min) Mean ± SE |
|---|---|---|
| Eucatropine | −0.007881 ± 0.001120 | 87.9 ± 12.5 |
| Int 1-4 | −0.009305 ± 0.001423 | 74.5 ± 11.4 |

Half Life Values of Test Compounds in Mouse Plasma Stability Experiment

Method: Assay was carried out in 96-well microtiter plates. Compounds were incubated in replicates (n=2) for 0, 5, 15, 30, and 45 minutes at 37° C. Reaction mixtures (20 μL) contained a final concentration of 3 μM test compound in fresh Sprague Dawley rat plasma. Eucatropine is a positive control to verify assay performance. Linear regression of semi-log plot of % remaining of compounds versus time used to determine the half-life $t_{1/2}$ values. Compound 1 the phosphate ester TEA salt of Int 1-4 was found to be stable in mouse plasma.

| Compound | Slope Mean ± SE | $t_{1/2}$ (min) Mean ± SE |
|---|---|---|
| Eucatropine | −0.030840 ± 0.003016 | 22.5 ± 2.2 |
| Compound 1 | 0.004130 ± 0.000752 | −167.8* ± 30.6 |

* Negative value indicates compound is stable

Example 8

Half Lives and Intrinsic Clearance Values of Int 1-4 in Human Liver S9 Stability Experiment Method: Liver S9 tissue fractions were used for in vitro assessment of metabolic stability of test compounds by cytochrome P450 (CYP450) mediated phase I oxidation, UDP-glucuronosyltransferase (UGT) mediated phase II glucuronidation, and metabolism through other pathways such as aldehyde oxidase (AO). The intrinsic clearance value for Int 1-4 was 2.22 uL/min/mg protein in human liver S9, anything less than ~4 uL/min/mg protein was considered a low clearance rate.

| Compound | Slope Mean ± SE | $t_{1/2}$ (min) Mean ± SE | CLint (mL/min/mg protein) Mean ± SE |
|---|---|---|---|
| Scopoletin | −0.84480 ± 0.002301 | 8.2 ± 0.2 | 0.033792 ± 0.000920 |
| Verapamil | −0.040700 ± 0.001737 | 17.0 ± 0.7 | 0.016280 ± 0.000695 |
| Int 1-4 | −0.005545 ± 0.000717 | 125.0 ± 16.2 | 0.002218 ± 0.000287 |

Half Lives and Intrinsic Clearance Values of Int 1-4 in Mouse Liver S9 Stability Experiment Method: Liver S9 tissue fractions were used for in vitro assessment of metabolic stability of test compounds by cytochrome P450 (CYP450) mediated phase I oxidation, UDP-glucuronosyltransferase (UGT) mediated phase II glucuronidation, and metabolism through other pathways such as aldehyde oxidase (AO). The intrinsic clearance value for Int 1-4 was 1.27 L/min/mg protein in mouse liver S9, anything less than ~4 μL/min/mg protein is considered a low clearance rate. The $CL_{int}$ for Int 1-4 in mouse liver S9 is consistent with in vivo mouse liver PK studies.

| Compound | Slope Mean ± SE | $t_{1/2}$ (min) Mean ± SE | CLint (mL/min/mg protein) Mean ± SE |
|---|---|---|---|
| Scopoletin | −0.061270 ± 0.006525 | 11.3 ± 1.2 | 0.024508 ± 0.002610 |
| Verapamil | −0.020520 ± 0.002403 | 33.8 ± 4.0 | 0.008208 ± 0.000961 |
| Int 1-4 | −0.003170 ± 0.000413 | 218.6 ± 28.5 | 0.001268 ± 0.000165 |

Half Lives and Intrinsic Clearance Values of Int 1-4 in Monkey Liver S9 Stability Experiment Method: Liver S9 tissue fractions were used for in vitro assessment of metabolic stability of test compounds by cytochrome P450 (CYP450) mediated phase I oxidation, UDP-glucuronosyltransferase (UGT) mediated phase II glucuronidation, and metabolism through other pathways such as aldehyde oxidase (AO). The intrinsic clearance value for Int 1-4 was 1.55 L/min/mg protein in mouse liver S9, anything less than ~4 μL/min/mg protein is considered a low clearance rate. Low $CL_{int}$ for Int 1-4 in monkey liver S9 is consistent with in vivo monkey plasma PK data

| Compound | Slope Mean ± SE | $t_{1/2}$ (min) Mean ± SE | CLint (mL/min/mg protein) Mean ± SE |
|---|---|---|---|
| Scopoletin | −0.139100 ± 0.014060 | 5.0 ± 0.5 | 0.055640 ± 0.005624 |
| Verapamil | −0.175200 ± 0.014150 | 4.0 ± 0.3 | 0.070080 ± 0.005660 |
| Int 1-4 | −0.038810 ± 0.002089 | 17.9 ± 1.0 | 0.015524 ± 0.000836 |

Half Lives and Intrinsic Clearance Values of in Dog Liver S9 Stability Experiment Method: Liver S9 tissue fractions were used for in vitro assessment of metabolic stability of test compounds by cytochrome P450 (CYP450) mediated phase I oxidation, UDP-glucuronosyltransferase (UGT) mediated phase 11 glucuronidation, and metabolism through other pathways such as aldehyde oxidase (AO). The intrinsic clearance value for Int 1-4 was 2.2 μL/min/mg protein in mouse liver S9, anything less than ~4 μL/min/mg protein is considered a low clearance rate. $CL_{int}$ for Int 1-4 in dog liver S9 is similar that for human liver S9.

| Compound | Slope Mean ± SE | $t_{1/2}$ (min) Mean ± SE | CLint (mL/min/mg protein) Mean ± SE |
|---|---|---|---|
| Scopoletin | −0.038920 ± 0.001665 | 17.8 ± 0.8 | 0.015568 ± 0.000666 |
| Verapamil | −0.024920 ± 0.000666 | 27.8 ± 0.7 | 0.009968 ± 0.000267 |
| Int 1-4 | −0.005558 ± 0.000749 | 124.7 ± 16.8 | 0.002223 ± 0.000299 |

Half Lives and Intrinsic Clearance Values of Int 1-4 in Rat Liver S9 Stability Experiment Liver S9 tissue fractions were used for in vitro assessment of metabolic stability of test compounds by cytochrome P450 (CYP450) mediated phase I oxidation, UDP-glucuronosyltransferase (UGT) mediated phase 11 glucuronidation, and metabolism through other pathways such as aldehyde oxidase (AO). The intrinsic clearance value for Int 1-4 was 14.3 μL/min/mg protein in rat liver S9 and is considered a moderately high rate of clearance.

| Compound | Slope Mean ± SE | $t_{1/2}$ (min) Mean ± SE | CLint (mL/min/mg protein) Mean ± SE |
|---|---|---|---|
| Scopoletin | −0.031340 ± 0.001980 | 22.1 ± 1.4 | 0.012536 ± 0.000792 |
| Verapamil | −0.020080 ± 0.001749 | 34.5 ± 3.0 | 0.008032 ± 0.000700 |
| Int 1-4 | −0.035790 ± 0.001471 | 19.4 ± 0.8 | 0.014316 ± 0.000588 |

Classification bands which can be used for categorizing compounds into low or high clearance from human S9 stability data:

| Clearance Catagory | S9 Intrinsic Clearance (μL/min/mg protein) Human |
|---|---|
| Low | <4.5 |
| High | >24.6 |

Int 1-4 exhibits low S9 intrinsic clearance values $Cl_{int}$<2.5 μL/min/mg protein in human, mouse, dog, and monkey but a moderately high value in the rat $Cl_{int}$~14 μL/min/mg protein. The S9 intrinsic clearance values across species are consistent with in vivo plasma/normal tissue PK stability studies for Int 1-4.

Example 9

Int 1-4 Metabolic Stability in Human, Dog, Monkey, Rat, and Mouse Liver Microsomes

| | Int 1-4 Liver Microsomal Stability | | | | | | | | | |
|---|---|---|---|---|---|---|---|---|---|---|
| | Compound Remaining (% of 0 min) | | | | | | $CL_{int}$ (μL/ min/mg protein) | SE $CL_{int}$ | $t_{1/2}$ (min) | n |
| Species | 0 min | 5 min | 15 min | 30 min | 45 min | control | | | | |
| Rat | 100 | 64.7 | 20.0 | 1.81 | 0.13 | 95.6 | 297 | 16.1 | 4.66 | 5 |
| Mouse | 100 | 102 | 78.4 | 73.6 | 70.7 | 93.2 | 17.1 | 4.43 | 81.2 | 5 |
| Dog | 100 | 97.1 | 90.8 | 85.7 | 80.4 | 94.5 | 9.63 | 0.597 | 144 | 5 |
| Monkey | 100 | 99.5 | 79.8 | 61.0 | 40.5 | 97.2 | 40.8 | 3.23 | 34.0 | 5 |
| Human | 100 | 111 | 94.0 | 107 | 99.9 | 102 | 0.747 | 3.98 | 1850 | 5 |
| Gemcitabine Liver Microsomal Stability | | | | | | | | | | |
| Human | 100 | 113 | 69.1 | 48.6 | 22.4 | 98.1 | 68.8 | 8.79 | 20.1 | 5 |

Classification bands typically used for categorizing compounds into low, medium or high clearance in liver microsomes:

| Clearance Catagory | Liver Microsome Intrinsic Clearance (μL/min/mg protein) | | | | |
|---|---|---|---|---|---|
| | Human | Monkey | Dog | Rat | Mouse |
| Low | <8.6 | <12.5 | <5.3 | <13.2 | <8.8 |
| High | >47.0 | >67.8 | >28.9 | >71.9 | >48.0 |

Int 1-4 appears to be stable in human liver microsomes CLint=0.75 mL/min/mg protein.

Int 1-4 has a high clearance rate in rat liver microsomes CLint=297 mL/min/mg protein

Example 10

Int 1-4 Metabolic Stability in Human, Rat, Mouse, Dog, Monkey Liver Hepatocytes

| Species | Compound | Slope mean ± SE | $t_{1/2}$ (min) mean ± SE | CLint (µL/min/mg protein) mean ± SE |
|---|---|---|---|---|
| Mouse | Naxalone | −0.018280 ± 0.000731 | 37.9 ± 1.5 | 18.28 ± 0.73 |
| | Int 1-4 | −0.006655 ± 0.000810 | 104.1 ± 12.7 | 6.66 ± 0.81 |
| | gemcitabine | −0.000512 ± 0.001111 | 1352.5 ± 2932.4 | 0.51 ± 1.11 |
| Rat | Naxalone | −0.019910 ± 0.001256 | 34.8 ± 2.2 | 19.91 ± 1.26 |
| | Int 1-4 | −0.007701 ± 0.001794 | 90.0 ± 21.0 | 7.70 ± 1.79 |
| | gemcitabine | 0.000550 ± 0.001504 | −1260.9* ± 3450.5 | −0.55 ± 1.50 |
| Dog | Naxalone | −0.01302 ± 0.001119 | 53.2 ± 4.6 | 13.02 ± 1.12 |
| | Int 1-4 | −0.004330 ± 0.001287 | 160.0 ± 47.6 | 4.33 ± 1.29 |
| | gemcitabine | 0.000126 ± 0.001156 | −5486.9* ± 50220.9 | −0.13 ± 1.16 |
| Monkey | Naxalone | −0.029480 ± 0.001002 | 23.5 ± 0.8 | 29.48 ± 1.00 |
| | Int 1-4 | −0.005018 ± 0.001425 | 138.1 ± 39.2 | 5.02 ± 1.43 |
| | gemcitabine | 0.001817 ± 0.001897 | −381.4* ± 398.2 | −1.82 ± 1.90 |
| Human | Naxalone | −0.013350 ± 0.000878 | 51.9 ± 3.4 | 13.35 ± 0.88 |
| | Int 1-4 | −0.003031 ± 0.001361 | 228.6 ± 102.7 | 3.03 ± 1.36 |
| | gemcitabine | −0.006840 ± 0.001905 | 101.3 ± 28.2 | 6.84 ± 1.91 |

*Negative value indicates compound is stable

Classification bands typically used for categorizing compounds into low or high clearance in liver hepatocytes:

| Clearance Catagory | Hepatocyte Intrinsic Clearance (µL/min/mg protein) | | | | |
|---|---|---|---|---|---|
| | Human | Monkey | Dog | Rat | Mouse |
| Low | <3.5 | <5.2 | <1.9 | <5.1 | <3.3 |
| High | >19.0 | >28.3 | >10.5 | >27.5 | >17.8 |

Int 1-4 exhibits relatively low intrinsic clearance values $C_{int}$~3 to 8 µL/min/mg across species hepatocytes with rat being the highest rate of clearance and human the lowest. Gemcitabine is metabolic stability in rat hepatocytes is consistent with the long half-life and high exposure in rat plasma PK studies.

The foregoing disclosure has been described in some detail by way of illustration and example, for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

What is claimed is:

1. A compound having one of the following structures:

| Compound # | Structure |
|---|---|
| 1 | 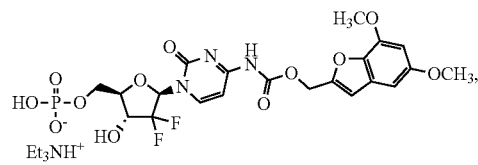 |
| 2 | 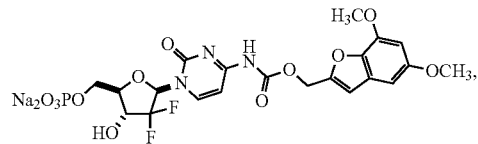 |
| 3 | 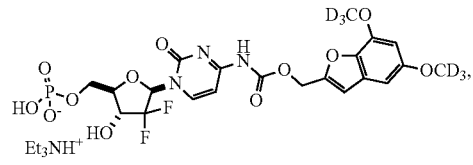 |
| 4 | 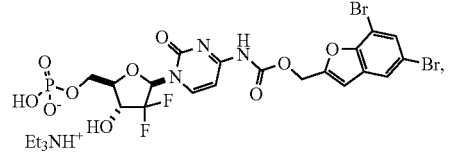 [SMILES: "Et3NH+" ; O=C(Nc1ccn([C@@H]2O[C@H](COP(=O)([O-])O)[C@@H](O)C2(F)F)c(=O)n1)OCc1cc2cc(Br)cc(Br)c2o1] |
| 5 | 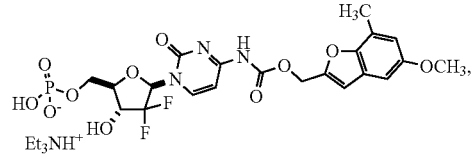 |

| Compound # | Structure |
|---|---|
| 6 | 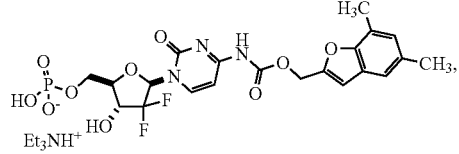 |
| 7 | 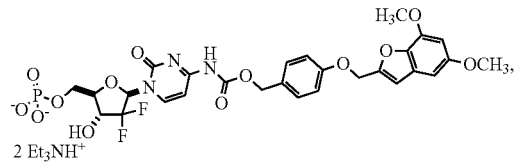 |
| 8 | 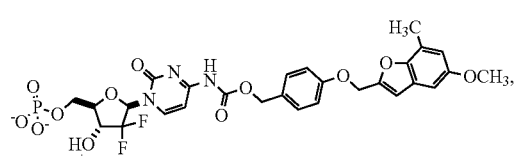 |
| 9 | 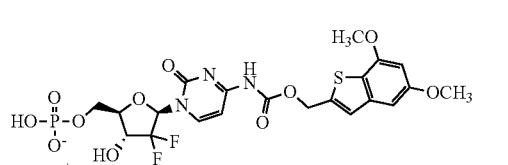 | or a pharmaceutically acceptable salt, ester, amide, solvate, or stereoisomer of any one of compounds 1-9.

2. A compound, having formula (Id-ii-1)

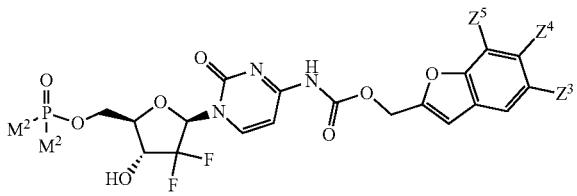

or a pharmaceutically acceptable salt, ester, amide, solvate, or stereoisomer thereof
wherein:
$Z^3$, $Z^4$, and $Z^5$ are each independently hydrogen, methyl optionally substituted with 1-3 halo, halo, methoxy optionally substituted with 1-3 halo or deuterated methoxy; and
each $M^2$ is independently selected from the group consisting of OH and $O^-$ (M'), wherein (M') in each occurrence is independently a metal cation, ammonium, an alkyl ammonium cation, or an amino acid cation.

3. The compound of 2, wherein each of $Z^5$ and $Z^3$ is independently methoxy.

4. The compound of 2, wherein $Z^4$ is hydrogen.

5. The compound of 2, wherein the compound is:

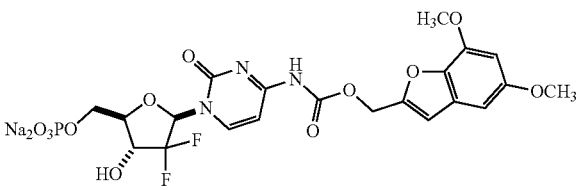

or a pharmaceutically acceptable salt, ester, amide, solvate, or stereoisomer thereof.

* * * * *